(12) United States Patent
Bordeaux et al.

(10) Patent No.: US 10,470,800 B2
(45) Date of Patent: Nov. 12, 2019

(54) EXTERNAL BONE FIXATION DEVICE

(71) Applicant: DePuy Synthes Products, Inc., Raynham, MA (US)

(72) Inventors: Jean-Noel Bordeaux, West Chester, PA (US); Michael Wahl, Wilmington, DE (US); Thomas Maughan, Downingtown, PA (US); Nicole Murray, West Milford, NJ (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/590,687

(22) Filed: May 9, 2017

(65) Prior Publication Data

US 2017/0238967 A1    Aug. 24, 2017

Related U.S. Application Data

(63) Continuation of application No. 14/774,374, filed as application No. PCT/US2014/025263 on Mar. 13, (Continued)

(51) Int. Cl.
| | |
|---|---|
| *A61B 17/00* | (2006.01) |
| *A61B 17/60* | (2006.01) |
| *A61B 17/62* | (2006.01) |
| *A61B 17/64* | (2006.01) |
| *A61B 17/66* | (2006.01) |

(52) U.S. Cl.
CPC ............ *A61B 17/60* (2013.01); *A61B 17/62* (2013.01); *A61B 17/6416* (2013.01); *A61B 17/6466* (2013.01); *A61B 17/66* (2013.01); *A61B 17/64* (2013.01); *A61B 17/6441* (2013.01); *A61B 2017/606* (2013.01)

(58) Field of Classification Search
CPC ............................................. A61B 17/60–666
See application file for complete search history.

(56) References Cited

U.S. PATENT DOCUMENTS 2,055,024 A    9/1936 Bittner, Jr.
2,391,537 A    12/1945 Anderson
(Continued)

FOREIGN PATENT DOCUMENTS

CN    1494397    5/2004
EP    1100048 A1    5/2001
(Continued)

OTHER PUBLICATIONS

Viceconti et al., "A software simulation of tibial fracture reduction with external fixator", Computer Methods and Programs in Biomedicine, 1993, 40, 89-94.
(Continued)

*Primary Examiner* — Nicholas J Plionis
*Assistant Examiner* — Steven J Cotroneo
(74) *Attorney, Agent, or Firm* — BakerHostetler

(57) ABSTRACT

The present application discloses embodiments related to an external bone fixation device configured to correct bone deformities or repair bone injuries. The device can include a plurality of bases configured to be attached to portions of a bone and a plurality of struts configured to be adjustable in length to change the position and orientation of the plurality of bases and the attached bone portions.

14 Claims, 37 Drawing Sheets

Related U.S. Application Data 2014, now Pat. No. 9,675,382, which is a continuation-in-part of application No. 13/800,545, filed on Mar. 13, 2013, now Pat. No. 8,864,763, which is a continuation-in-part of application No. 13/800,319, filed on Mar. 13, 2013, now Pat. No. 9,039,706.

(56) References Cited

U.S. PATENT DOCUMENTS

| | | |
|---|---|---|
| 3,977,397 A | 8/1976 | Sinitsyn |
| 4,081,686 A | 3/1978 | Nieuweboer |
| 4,450,834 A | 5/1984 | Fischer |
| 4,489,111 A | 12/1984 | Woodrum |
| 4,615,338 A | 10/1986 | Ilizarov et al. |
| 4,620,533 A | 11/1986 | Mears |
| 4,630,203 A | 12/1986 | Szirtes |
| 4,768,524 A | 9/1988 | Hardy |
| 4,784,125 A | 11/1988 | Monticelli et al. |
| 4,875,165 A | 10/1989 | Fencil et al. |
| 4,889,111 A | 12/1989 | Ben-Dov |
| 4,890,631 A | 1/1990 | Hardy |
| 4,930,961 A | 6/1990 | Weis |
| 4,964,320 A | 10/1990 | Lee, Jr. |
| 4,973,331 A | 11/1990 | Pursley et al. |
| 5,062,844 A | 11/1991 | Jamison et al. |
| 5,074,866 A | 12/1991 | Sherman et al. |
| 5,087,258 A | 2/1992 | Schewior |
| 5,095,919 A | 3/1992 | Monticelli et al. |
| 5,108,393 A | 4/1992 | Ruffa |
| 5,156,605 A | 10/1992 | Pursley et al. |
| 5,179,525 A | 1/1993 | Griffis et al. |
| 5,180,380 A | 1/1993 | Pursley et al. |
| 5,209,750 A | 5/1993 | Stef |
| 5,275,598 A | 1/1994 | Cook |
| 5,358,504 A | 10/1994 | Paley et al. |
| 5,437,668 A | 8/1995 | Aronson et al. |
| 5,443,464 A | 8/1995 | Russell et al. |
| 5,451,225 A | 9/1995 | Ross, Jr. et al. |
| 5,458,599 A | 10/1995 | Adobbati |
| 5,540,686 A | 7/1996 | Zippel et al. |
| 5,601,551 A | 2/1997 | Taylor et al. |
| 5,630,814 A | 5/1997 | Ross, Jr. et al. |
| 5,653,707 A | 8/1997 | Taylor et al. |
| 5,681,309 A | 10/1997 | Ross, Jr. et al. |
| 5,702,389 A * | 12/1997 | Taylor ............... A61B 17/62 |
| | | 606/56 |
| 5,728,095 A | 3/1998 | Taylor et al. |
| 5,746,741 A | 5/1998 | Kraus et al. |
| 5,766,173 A | 6/1998 | Ross, Jr. et al. |
| 5,776,132 A | 7/1998 | Blyakher |
| 5,871,018 A | 2/1999 | Delp et al. |
| 5,885,282 A | 3/1999 | Szabo |
| 5,891,143 A | 4/1999 | Taylor et al. |
| 5,919,192 A | 7/1999 | Shouts |
| 5,951,556 A | 9/1999 | Faccioli et al. |
| 5,961,515 A | 10/1999 | Taylor et al. |
| 5,963,612 A | 10/1999 | Navab |
| 5,968,043 A | 10/1999 | Ross, Jr. et al. |
| 5,971,984 A | 10/1999 | Taylor et al. |
| 5,976,142 A | 11/1999 | Chin |
| 6,017,341 A | 1/2000 | Windhagen et al. |
| 6,021,579 A | 2/2000 | Schimmels |
| 6,030,386 A * | 2/2000 | Taylor ............... A61B 17/62 |
| | | 606/54 |
| 6,047,080 A | 4/2000 | Chen et al. |
| 6,129,727 A | 10/2000 | Austin et al. |
| 6,206,566 B1 | 3/2001 | Schuetz |
| 6,293,947 B1 | 9/2001 | Buchbinder |
| 6,320,928 B1 | 11/2001 | Vaillant et al. |
| 6,363,169 B1 | 3/2002 | Ritter et al. |
| 6,434,278 B1 | 8/2002 | Hashimoto |
| 6,501,848 B1 | 12/2002 | Carroll et al. |
| 6,510,241 B1 | 1/2003 | Vaillant et al. |
| 6,537,275 B2 | 3/2003 | Venturini et al. |
| 6,701,174 B1 | 3/2004 | Krause et al. |
| 6,912,293 B1 | 6/2005 | Korobkin |
| 7,113,623 B2 | 9/2006 | Chen et al. |
| 7,187,792 B2 | 3/2007 | Fu et al. |
| 7,226,449 B2 | 6/2007 | Venturini et al. |
| 7,280,687 B2 | 10/2007 | Ban et al. |
| 7,306,601 B2 * | 12/2007 | McGrath ............... A61B 17/62 |
| | | 606/53 |
| 7,388,972 B2 | 6/2008 | Kitson |
| 7,490,085 B2 | 2/2009 | Walker et al. |
| RE40,914 E * | 9/2009 | Taylor ............... A61B 17/62 |
| | | 606/53 |
| 7,645,279 B1 | 1/2010 | Haupt |
| 7,657,079 B2 | 2/2010 | Lake et al. |
| 7,677,078 B2 | 3/2010 | Sauer et al. |
| 7,758,582 B2 | 7/2010 | Ferrante et al. |
| 7,828,801 B2 | 11/2010 | Mirza et al. |
| 7,837,621 B2 | 11/2010 | Krause et al. |
| 7,887,537 B2 | 2/2011 | Ferrante et al. |
| 7,955,334 B2 | 6/2011 | Steiner et al. |
| 8,029,505 B2 | 10/2011 | Hearn et al. |
| 8,057,474 B2 | 11/2011 | Knuchel et al. |
| 8,062,293 B2 | 11/2011 | Steiner et al. |
| 8,147,491 B2 | 4/2012 | Lavi |
| 8,157,800 B2 | 4/2012 | Mikheev |
| 8,202,273 B2 | 6/2012 | Karidis |
| 8,257,353 B2 | 9/2012 | Wong |
| 8,282,652 B2 | 10/2012 | Mackenzi et al. |
| 8,296,094 B2 | 10/2012 | Harrison et al. |
| 8,323,282 B2 | 12/2012 | Taylor |
| 8,333,766 B2 | 12/2012 | Edelhauser et al. |
| 8,377,060 B2 | 2/2013 | Thomas |
| 8,419,732 B2 | 4/2013 | Mullaney |
| 8,425,512 B2 | 4/2013 | Vasta et al. |
| 8,430,878 B2 | 4/2013 | Vasta et al. |
| 8,439,914 B2 | 5/2013 | Ross et al. |
| 8,444,644 B2 | 5/2013 | Ross et al. |
| 8,454,604 B2 | 6/2013 | Wong |
| 8,469,958 B2 | 6/2013 | Stevens |
| 8,574,232 B1 | 11/2013 | Ross et al. |
| 8,654,150 B2 | 2/2014 | Haskell |
| 8,777,946 B2 | 7/2014 | Lindahl et al. |
| 8,834,467 B2 | 9/2014 | Singh et al. |
| 8,858,555 B2 * | 10/2014 | Crozet ............... A61B 17/62 |
| | | 606/54 |
| 8,864,763 B2 | 10/2014 | Murray et al. |
| 8,906,021 B1 | 12/2014 | Lehmann et al. |
| 8,945,128 B2 | 2/2015 | Singh et al. |
| 8,951,252 B2 | 2/2015 | Steiner et al. |
| 8,952,986 B2 | 2/2015 | Haskell |
| 9,011,438 B2 | 4/2015 | Steiner et al. |
| 9,017,339 B2 | 4/2015 | Edelhauser et al. |
| 9,039,706 B2 | 5/2015 | Murray et al. |
| 9,044,271 B2 | 6/2015 | Edelhauser et al. |
| 9,066,756 B2 | 6/2015 | Wong |
| 9,078,700 B2 | 7/2015 | Ross et al. |
| 9,101,398 B2 | 8/2015 | Singh et al. |
| 9,155,559 B2 | 10/2015 | Ross et al. |
| 9,204,937 B2 | 12/2015 | Edelhauser et al. |
| 9,220,533 B2 | 12/2015 | Singh et al. |
| 9,642,649 B2 | 5/2017 | Nikonovas |
| 9,895,167 B2 | 2/2018 | Edelhauser et al. |
| 2002/0010465 A1 | 1/2002 | Koo |
| 2003/0106230 A1 * | 6/2003 | Hennessey ............... B25J 7/00 |
| | | 33/645 |
| 2003/0191466 A1 * | 10/2003 | Austin ............... A61B 17/62 |
| | | 606/54 |
| 2004/0039259 A1 | 2/2004 | Krause et al. |
| 2004/0068187 A1 | 4/2004 | Krause et al. |
| 2004/0073211 A1 | 4/2004 | Austin et al. |
| 2004/0073212 A1 | 4/2004 | Kim |
| 2004/0097922 A1 | 5/2004 | Mullaney |
| 2004/0111024 A1 | 6/2004 | Zheng et al. |
| 2004/0133199 A1 | 7/2004 | Coati et al. |
| 2004/0167518 A1 | 8/2004 | Estrada |
| 2004/0208279 A1 | 10/2004 | Xiao et al. |
| 2005/0149018 A1 * | 7/2005 | Cooper ............... A61B 17/6425 |
| | | 606/54 |
| 2005/0215997 A1 | 9/2005 | Austin et al. |
| 2005/0256389 A1 | 11/2005 | Koga et al. |

(56) References Cited

U.S. PATENT DOCUMENTS

| | | |
|---|---|---|
| 2006/0276786 A1 | 12/2006 | Brinker |
| 2007/0043354 A1 | 2/2007 | Koo et al. |
| 2007/0049930 A1* | 3/2007 | Hearn .................... A61B 17/62 606/56 |
| 2007/0161983 A1 | 7/2007 | Cresina et al. |
| 2007/0161984 A1 | 7/2007 | Cresina et al. |
| 2007/0238069 A1 | 10/2007 | Lovald et al. |
| 2008/0012850 A1 | 1/2008 | Keating, III |
| 2008/0051779 A1 | 2/2008 | Mackenzie et al. |
| 2008/0114267 A1 | 5/2008 | Lloyd et al. |
| 2008/0234554 A1 | 9/2008 | Vvedensky et al. |
| 2008/0269741 A1 | 10/2008 | Karidis |
| 2009/0036890 A1 | 2/2009 | Karidis |
| 2009/0036892 A1 | 2/2009 | Karidis et al. |
| 2009/0105621 A1* | 4/2009 | Boyd .................... A61F 5/0195 602/3 |
| 2009/0143788 A1 | 6/2009 | Fang et al. |
| 2009/0161945 A1 | 6/2009 | Morgan-Mar et al. |
| 2009/0177198 A1* | 7/2009 | Theodoros ............. A61B 17/62 606/56 |
| 2009/0198234 A1 | 8/2009 | Knuchel et al. |
| 2009/0226055 A1 | 9/2009 | Dankowicz et al. |
| 2009/0275944 A1 | 11/2009 | Huebner et al. |
| 2009/0326532 A1 | 12/2009 | Schulze |
| 2010/0030219 A1 | 2/2010 | Lerner et al. |
| 2010/0039421 A1 | 2/2010 | Toyomura et al. |
| 2010/0087819 A1 | 4/2010 | Mullaney |
| 2010/0104150 A1 | 4/2010 | Saint Felix et al. |
| 2010/0172567 A1 | 7/2010 | Prokoski |
| 2010/0179548 A1* | 7/2010 | Marin .................... A61B 17/62 606/59 |
| 2010/0191239 A1 | 7/2010 | Sakkers et al. |
| 2010/0191500 A1 | 7/2010 | Harrison et al. |
| 2010/0234844 A1 | 9/2010 | Edelhauser et al. |
| 2010/0280516 A1 | 11/2010 | Taylor |
| 2010/0305568 A1 | 12/2010 | Ross et al. |
| 2010/0312243 A1 | 12/2010 | Ross et al. |
| 2011/0004199 A1 | 1/2011 | Ross et al. |
| 2011/0029093 A1 | 2/2011 | Bojarski et al. |
| 2011/0103676 A1 | 5/2011 | Mullaney |
| 2011/0118737 A1 | 5/2011 | Vasta et al. |
| 2011/0118738 A1 | 5/2011 | Vasta et al. |
| 2011/0131418 A1 | 6/2011 | Teng et al. |
| 2011/0208187 A1 | 8/2011 | Wong |
| 2011/0313418 A1 | 12/2011 | Nikonovas |
| 2011/0313419 A1* | 12/2011 | Mullaney .............. A61B 17/62 606/56 |
| 2012/0041439 A1 | 2/2012 | Singh et al. |
| 2012/0078251 A1* | 3/2012 | Benenati ............... A61B 17/62 606/56 |
| 2012/0232554 A1* | 9/2012 | Shaevitz ............... A61B 17/171 606/56 |
| 2012/0259343 A1 | 10/2012 | Clark et al. |
| 2012/0303028 A1 | 11/2012 | Wong |
| 2012/0330312 A1 | 12/2012 | Burgherr et al. |
| 2013/0041288 A1 | 2/2013 | Taylor et al. |
| 2013/0060146 A1 | 3/2013 | Yang et al. |
| 2013/0131675 A1 | 5/2013 | Vasta et al. |
| 2013/0138017 A1 | 5/2013 | Jundt et al. |
| 2013/0201212 A1 | 8/2013 | Haskell |
| 2013/0245625 A1 | 9/2013 | Vasta et al. |
| 2013/0289575 A1 | 10/2013 | Edelhauser et al. |
| 2013/0296857 A1 | 11/2013 | Lester |
| 2014/0135764 A1 | 5/2014 | Ross et al. |
| 2014/0236152 A1 | 8/2014 | Walberg et al. |
| 2014/0257286 A1 | 9/2014 | Lindahl et al. |
| 2014/0276817 A1 | 9/2014 | Murray et al. |
| 2014/0276821 A1 | 9/2014 | Murray et al. |
| 2014/0278325 A1 | 9/2014 | Burgherr et al. |
| 2014/0379038 A1 | 12/2014 | Dogramadzi et al. |
| 2015/0080892 A1 | 3/2015 | Lehmann et al. |
| 2015/0088135 A1 | 3/2015 | Singh |
| 2015/0112339 A1 | 4/2015 | Lindahl et al. |
| 2015/0223842 A1 | 8/2015 | Murray et al. |
| 2015/0238227 A1 | 8/2015 | Singh et al. |
| 2015/0257788 A1 | 9/2015 | Jay et al. |
| 2015/0265313 A1 | 9/2015 | Wong |
| 2015/0272624 A1 | 10/2015 | Singh |
| 2015/0305776 A1 | 10/2015 | Ross et al. |
| 2015/0305777 A1 | 10/2015 | Singh et al. |
| 2015/0313641 A1 | 11/2015 | Ross et al. |
| 2016/0022314 A1 | 1/2016 | Bordeaux et al. |
| 2016/0045225 A1 | 2/2016 | Edelhauser et al. |
| 2016/0092651 A1 | 3/2016 | Austin et al. |
| 2016/0113681 A1 | 4/2016 | Singh |
| 2017/0181800 A1 | 6/2017 | Nikonovas |
| 2017/0303966 A1 | 10/2017 | Edelhauser et al. |
| 2017/0348054 A1 | 12/2017 | Kumar et al. |
| 2017/0348057 A1 | 12/2017 | Kumar et al. |
| 2017/0354439 A1 | 12/2017 | Mannanal et al. |
| 2018/0055569 A1 | 3/2018 | Wahl et al. |

FOREIGN PATENT DOCUMENTS

| | | |
|---|---|---|
| EP | 1690506 A1 | 8/2006 |
| EP | 2767252 A1 | 8/2014 |
| FR | 2576774 A1 | 8/1986 |
| FR | 2756025 A1 | 5/1998 |
| JP | 2001-523985 A | 11/2001 |
| JP | 2003-144454 A | 5/2003 |
| JP | 2003-530177 A | 10/2003 |
| JP | 2006-507056 A | 3/2006 |
| JP | 2006-218298 A | 8/2006 |
| JP | 2009-505736 A | 2/2009 |
| JP | 2011-512883 A | 4/2011 |
| KR | 20-0443058 Y1 | 1/2009 |
| RU | 2159091 C2 | 11/2000 |
| RU | 2352283 C2 | 4/2009 |
| WO | 98/12975 A2 | 4/1998 |
| WO | 99/59100 A1 | 11/1999 |
| WO | 01/15611 A1 | 3/2001 |
| WO | 01/78015 A2 | 10/2001 |
| WO | 03/30759 A2 | 4/2003 |
| WO | 2007/024904 A2 | 3/2007 |
| WO | 2009/102904 A1 | 8/2009 |
| WO | 2010/002587 A1 | 1/2010 |
| WO | 2010/104567 A1 | 9/2010 |
| WO | 2011/026475 A1 | 3/2011 |
| WO | 2011/060264 A1 | 5/2011 |
| WO | 2011/060266 A1 | 5/2011 |
| WO | 2011/146703 A1 | 11/2011 |
| WO | 2014/186453 A2 | 11/2014 |

OTHER PUBLICATIONS

Tsai, A Versatile Camera Calibration Technique for High-Accuracy 3D Machine Vision Metrology Using off-the-shelf TV Cameras and Lenses, IEEE Journal of Robotics & Automation, RA-3, No. 4, 323-344, Aug. 1987.

Trucco, Introductory Techniques of 3-D Computer Vision, Prentice Hall, 178-194, 1998.

T.A. Larionova et al. "X-ray absorptiometry in the analysis of bone mineral density of a patient with an orthopaedic trauma", Genius of Orthopaedy No. 3, pp. 98-102 (w/English abstract) 2009.

Stoughton et al., "A Modified Stewart Platform Manipulator with Improved Dexterity", IEEE Transactions On Robotics And Automation, Apr. 1993, vol. 9, No. 2, 166-173.

Solomin, The Basic Principles of External Fixation Using The Ilizarov Device, 2005, 371 pages.

Solomin et al., Deformity Correction and Fracture Treatment by software-based Ortho-SUV Frame User Manual Draft, year and date of publication are unknown, 90 pages.

Solomin et al., Deformity Correction and Fracture Treatment by Software-Based Ortho-SUV Frame User Manual, 2013, 144 pages.

Simard et al., "The Ilizarov Procedure: Limb Lengthening and Its Implications", Physical Therapy, Jan. 1992, vol. 72, No. 1, 25-35.

Russakoff et al., "Intensity-Based 2D-3D Spine Image Registration Incorporating a Single Fiducial Marker", Academic Radiology, Jan. 2005, vol. 12, No. 1, 37-50.

(56) References Cited

OTHER PUBLICATIONS

Paley, "The principles of deformity correction by the Ilizarov technique: Technical aspects", Techniques in Orthopaedics, 1989, vol. 4, Issue 1, 15-29.
Paley et al., "Deformity Correction By The Ilizarov Technique", Operative Orthopaedics, 1993, 883-948.
Orthofix, TL-HEX Software User's Guide: Software version 1.4, Nov. 2015, 60 pages.
Maiocchi etl.; "Instruments and Their Use"; Operative Principles of Ilizarov; Chapter 2, 1991, 26 pages.
Kelly, "How to calculate 3D coordinates with two cameras, a calibration object, a java program, and a lot of MS Excel macros", Jun. 10, 2002, 9 pages.
Hartley, Euclidian Reconstruction from Uncalibrated Views, Applications of Invariance in Computer Vision, pp. 237-256, Springer Verlag, Berlin Heidelberg, 1994.
Garreau et al., "A Knowledge-Based Approach for 3-D Reconstruction and Labeling of Vascular Networks from Biplane Angiographic Projections", IEEE Transactions On Medical Imaging, Jun. 1991, vol. 10, No. 2, 122-131.
Decision to Grant (Translation) dated Mar. 2016 in Russian patent application 2012147835, 6 pages.
U.S. Appl. No. 15/461,969, filed Mar. 17, 2017, entitled Orthopedic Fixation with Imagery Analysis, Non-final Rejection dated Feb. 13, 2018.
U.S. Appl. No. 13/111,180, filed May 19, 2011, entitled Orthopedic Fixation with Imagery Analysis, Notice of Allowance dated Sep. 17, 2014.
U.S. Appl. No. 13/111,180, filed May 19, 2011, entitled Orthopedic Fixation with Imagery Analysis, Notice of Allowance dated Dec. 16, 2016.
U.S. Appl. No. 13/111,180, filed May 19, 2011, entitled Orthopedic Fixation with Imagery Analysis, Notice of Allowance dated Aug. 26, 2016.
U.S. Appl. No. 13/111,180, filed May 19, 2011, entitled Orthopedic Fixation with Imagery Analysis, Notice of Allowability dated Nov. 17, 2016.
U.S. Appl. No. 13/111,180, filed May 19, 2011, entitled Orthopedic Fixation with Imagery Analysis, Non-final Rejection dated Jun. 6, 2013.
U.S. Appl. No. 13/111,180, filed May 19, 2011, entitled Orthopedic Fixation with Imagery Analysis, Non-final Rejection dated Apr. 9, 2015.
U.S. Appl. No. 13/111,180, filed May 19, 2011, entitled Orthopedic Fixation with Imagery Analysis, Final Rejection dated Oct. 23, 2015.
U.S. Appl. No. 13/111,180, filed May 19, 2011, entitled Orthopedic Fixation with Imagery Analysis, Final Rejection dated Feb. 14, 2014.
Styker, Hoffmann LRF Hexapod, Operative technique, Jul. 2016, 44 pages.
Stryker, Hoffman LRF, Gradual Correction, Operative technique, 2016, 36 pages.
Solomin et al., Deformity Correction and Fracture Treatment by software-based Ortho-SUV Frame, User Manual, For SUV-Software vp 2.1, Vreden Russian Research Institute of Traumatology and Orthopedics, (Ortho-SUV) Ltd., Saint Petersburg, 2016, 158 pages.
Solomin et al., Deformity Correction and Fracture Treatment by software-based Ortho-SUV Frame, User Manual, For SUV-Software vp 1.0 and vr 1.0, Vreden Russian Research Institute of Traumatology and Orthopedics, (Ortho-SUV) Ltd., Saint Petersburg, 2013, 144 pages.
Ren L, Feng Z, Mills JK. A self-tuning iterative calculation approach for the forward kinematics of a Stewart-Gough platform. In Mechatronics and Automation, Proceedings of the 2006 IEEE International Conference on Jun. 25, 2006, 2018-2023.
Parikh PJ, Lam SS. A hybrid strategy to solve the forward kinematics problem in parallel manipulators. IEEE Transactions on Robotics. Feb. 2005; 21(1): 18-25.
Nikonovas, Arkadijus. Taylor Spatial Frame: Kinematics, Mechanical Properties and Automation. Diss. University of Bristol, May 2005, 230 pages.
Durali M, Shameli E. Full order neural velocity and acceleration observer for a general 6-6 Stewart platform. InNetworking, Sensing and Control, 2004 IEEE International Conference on Mar. 21, 2004 (vol. 1, pp. 333-338).
Charlton, an Investigation into the Effect of Lateral Hillslope inputs on Floorplain Hydraulic Model Predictions, Diss.University of Bristol, Sep. 1995, 289 pages.
Ortho-SUV Frame—Art of Deformity Correction, Ortho-SUV Ltd, captured by https://web.archive.org from http://www.miito.org/download/ortho-suv-frame-eng.pdfon Jun. 13, 2010; 11 pages.
Changjiang Yang et al: "Planar conic based camera calibration", Proceedings / 15th International Conference on Pattern Recognition Barcelona, Spain, Sep. 3-7, [Proceedings of the International Conference on Pattern Recognition. (ICPR)], IEEE Computer Society, Los Alamitos, Calif. [U.A.], vol. 1, Sep. 3, 2000 (Sep. 3, 2000) pp. 555-558.

\* cited by examiner

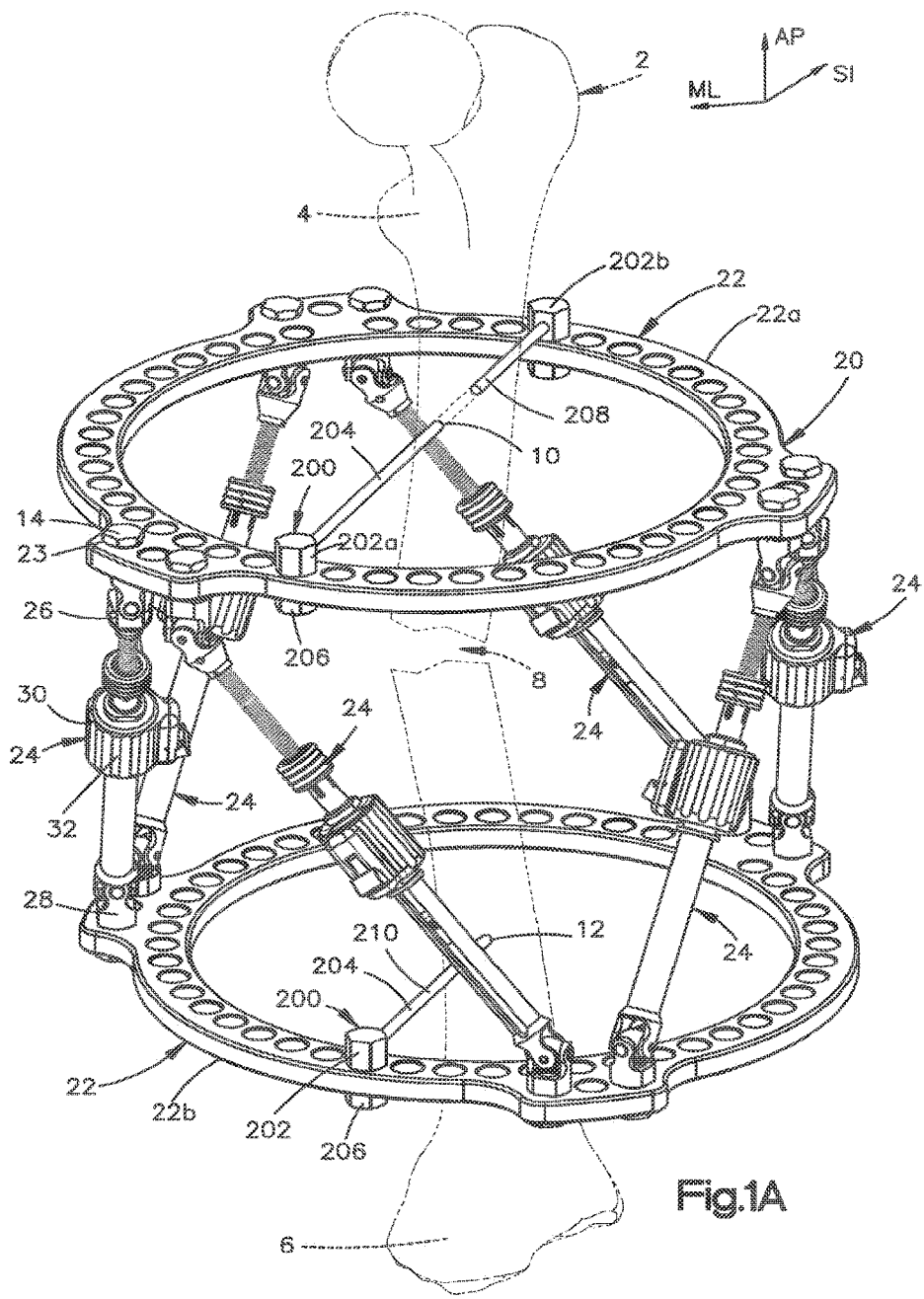

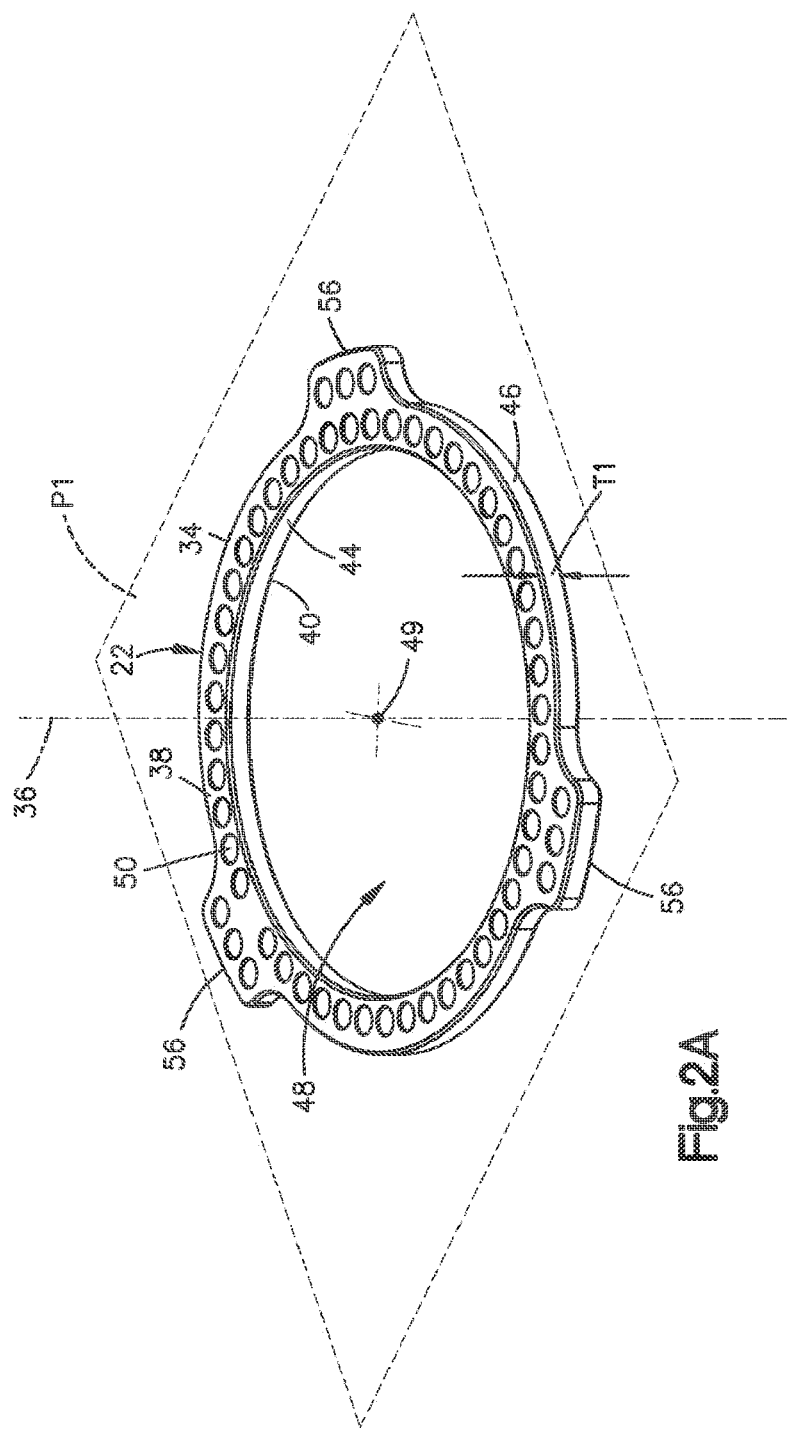

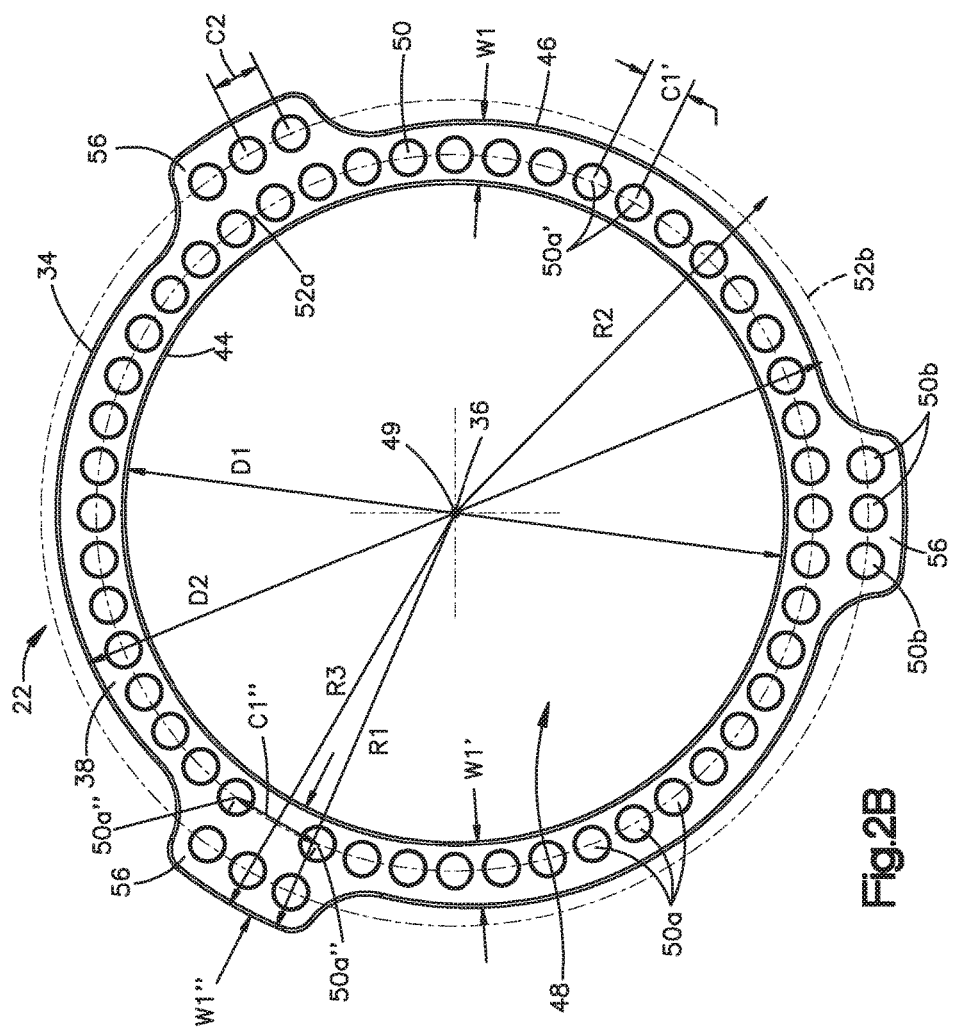

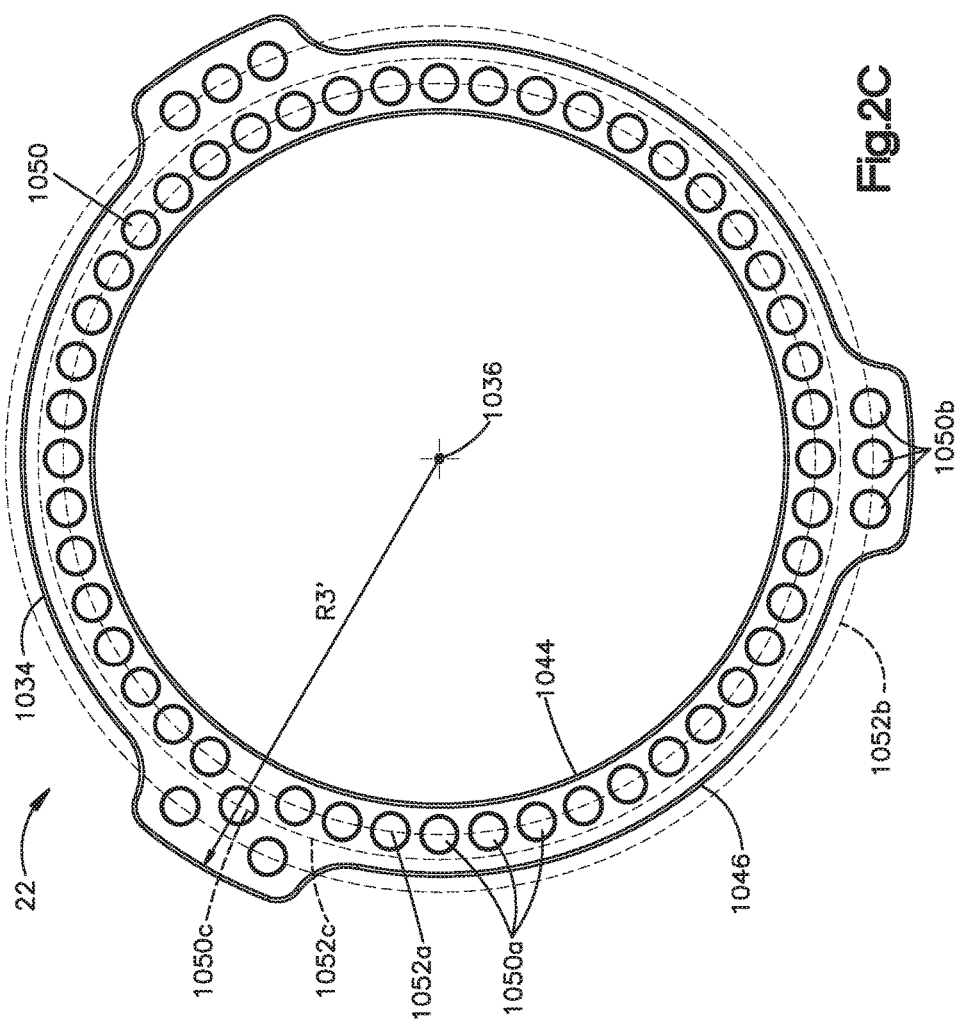

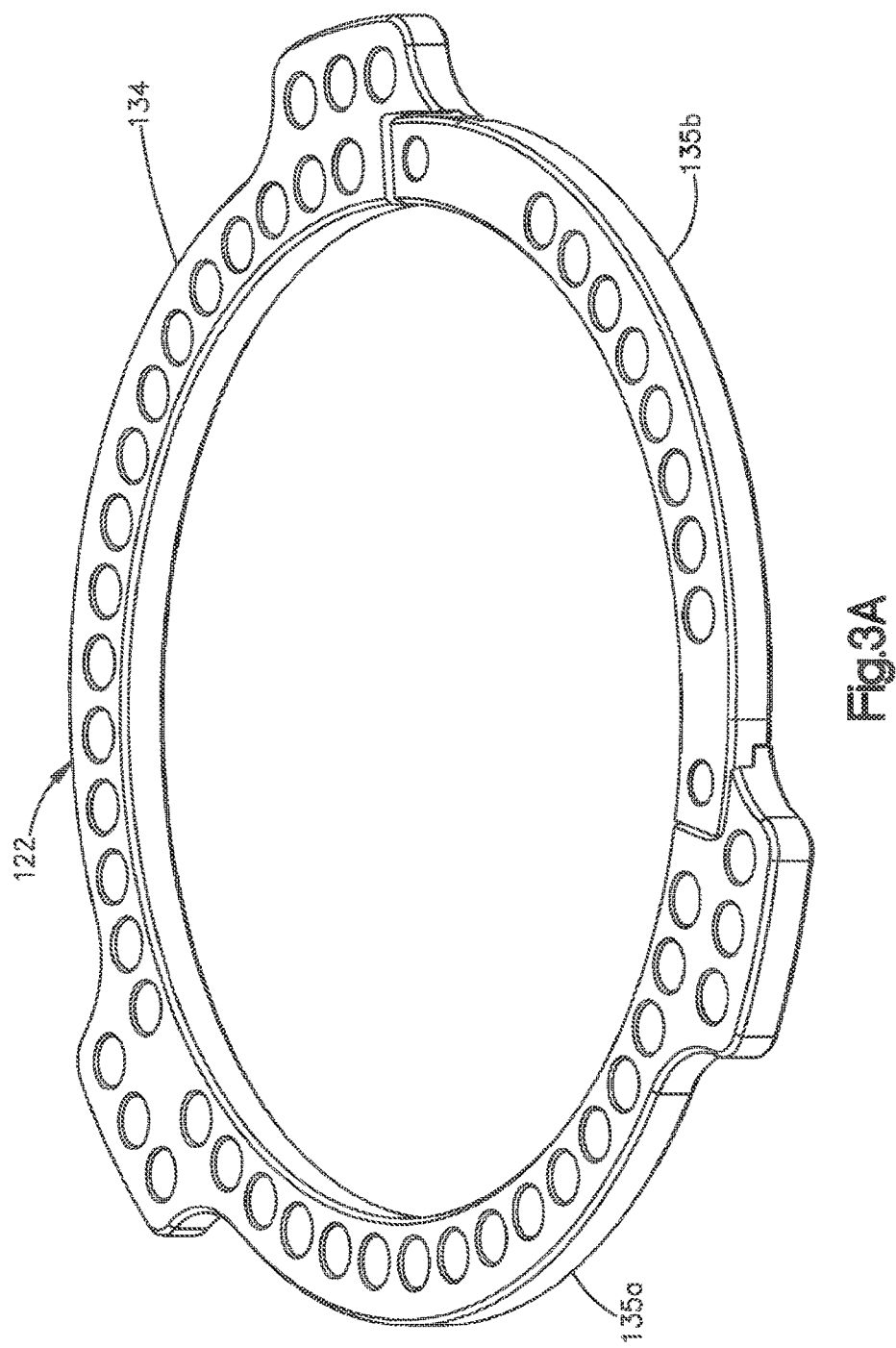

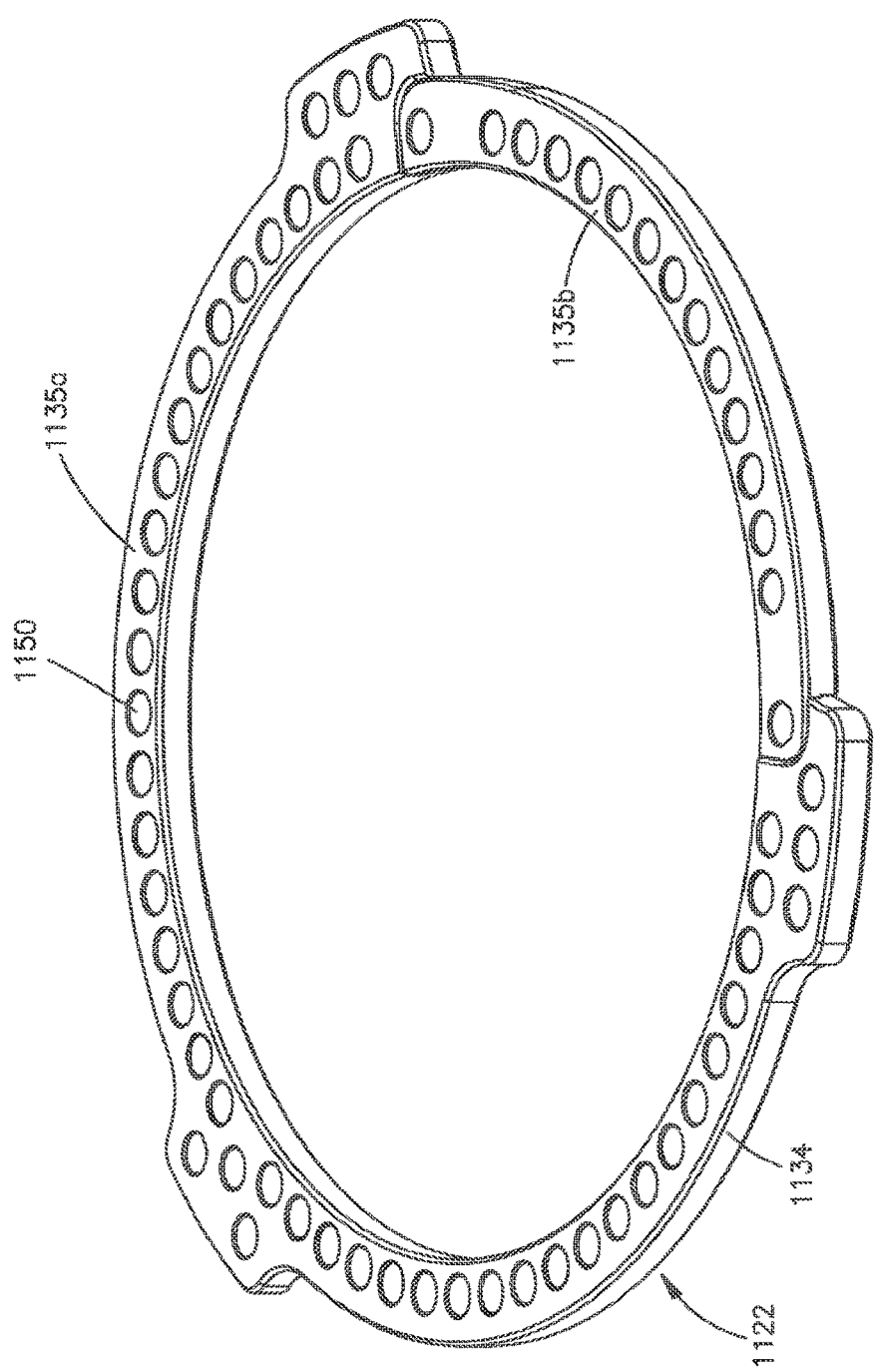

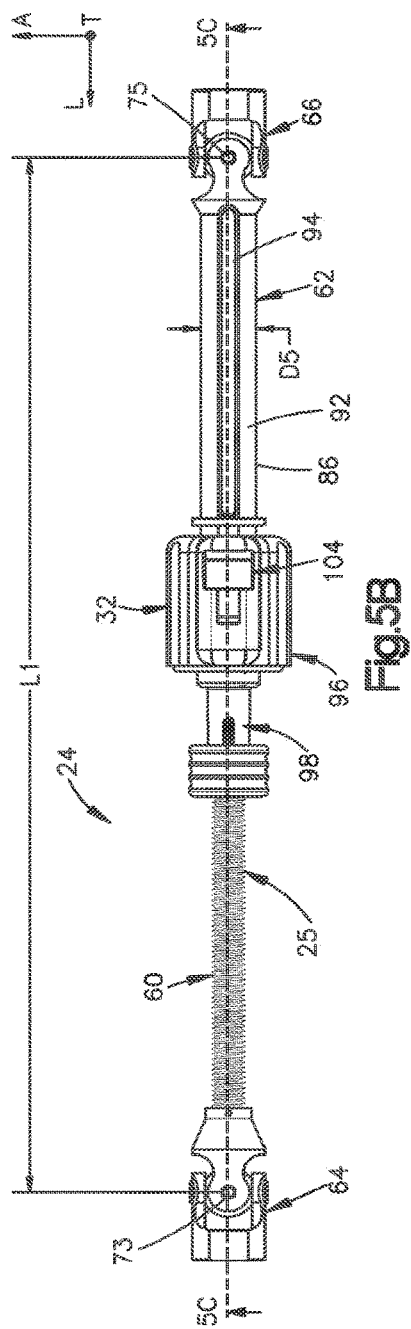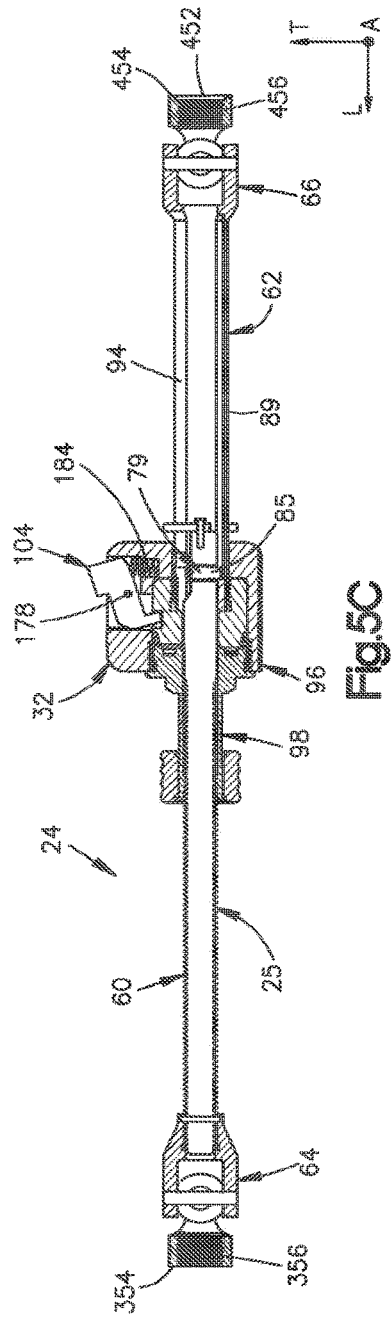

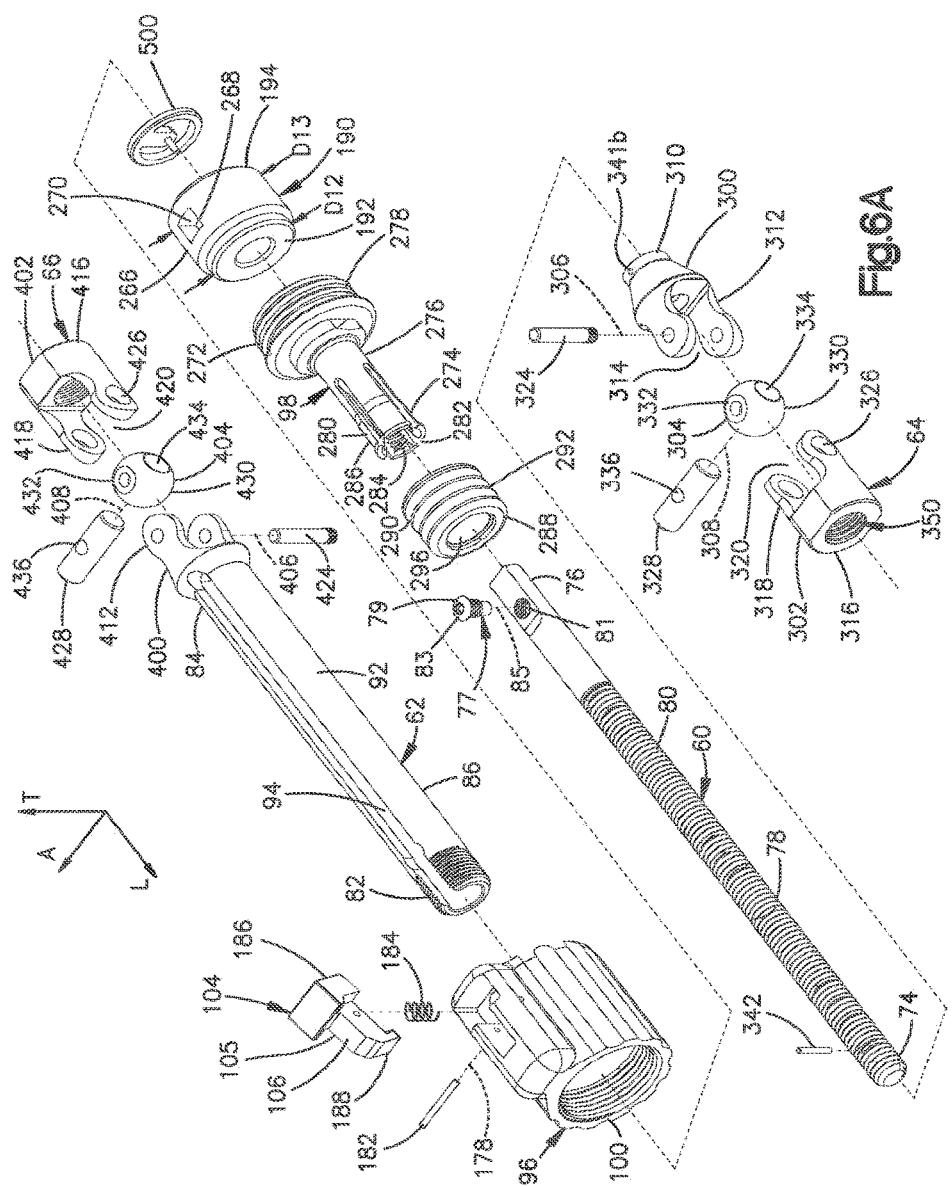

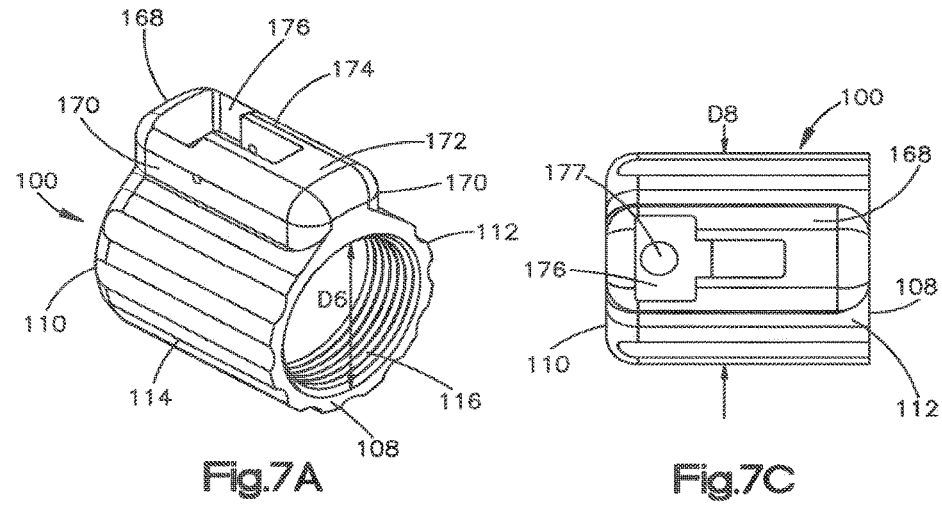
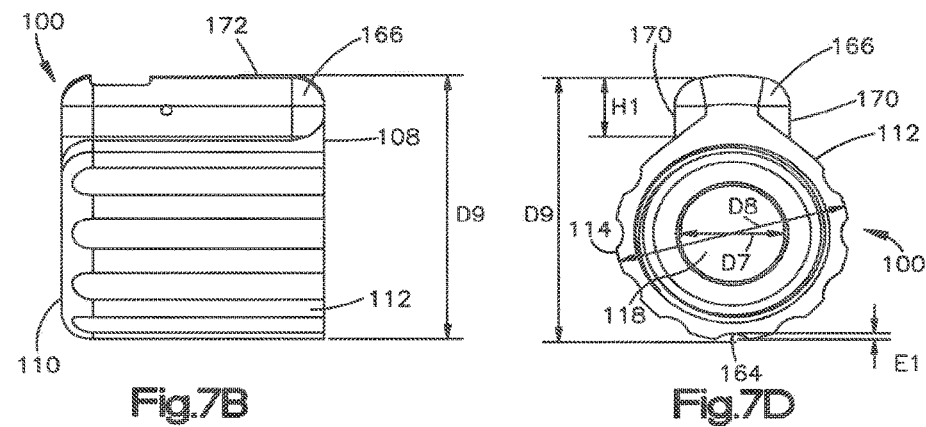

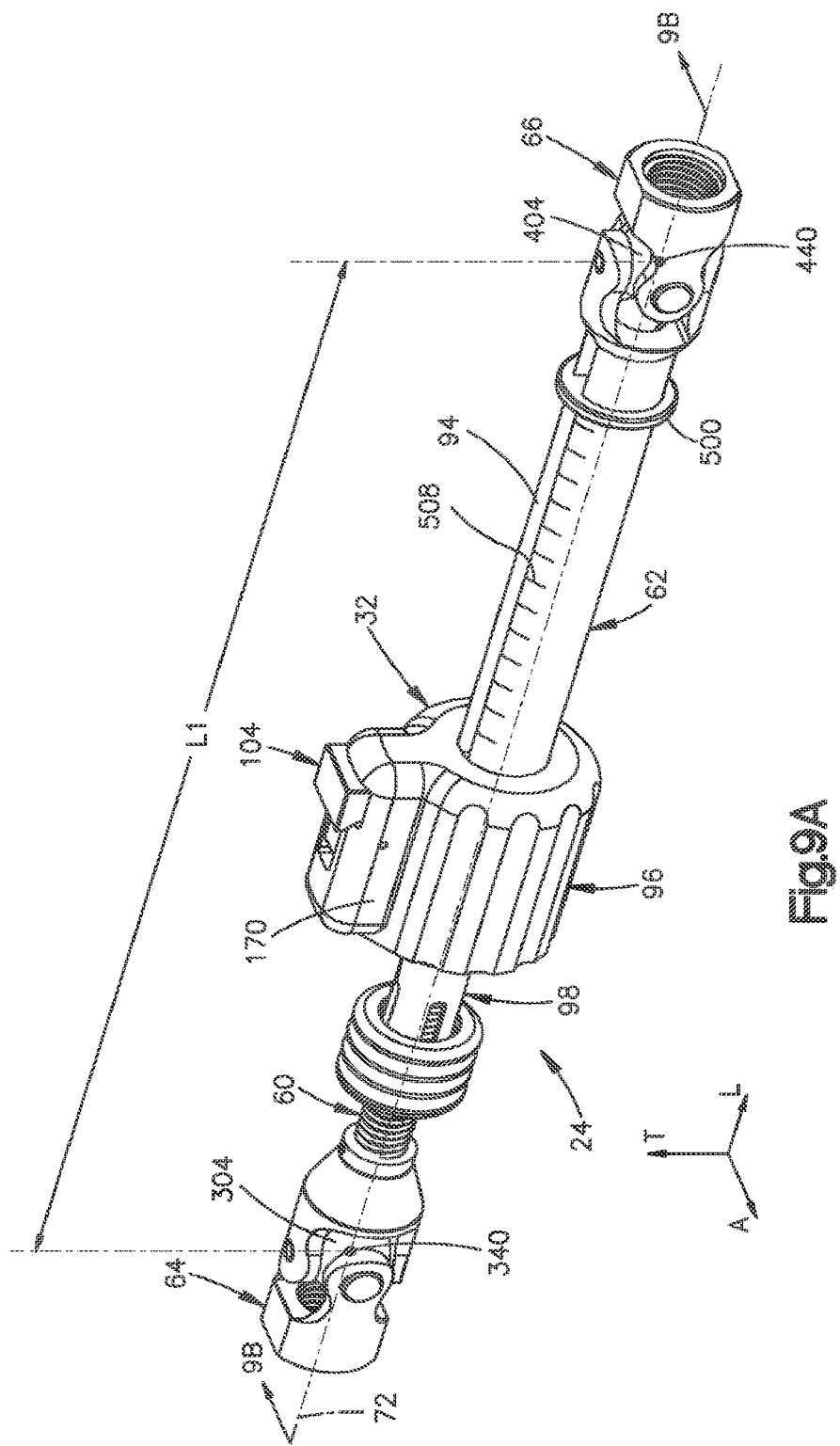

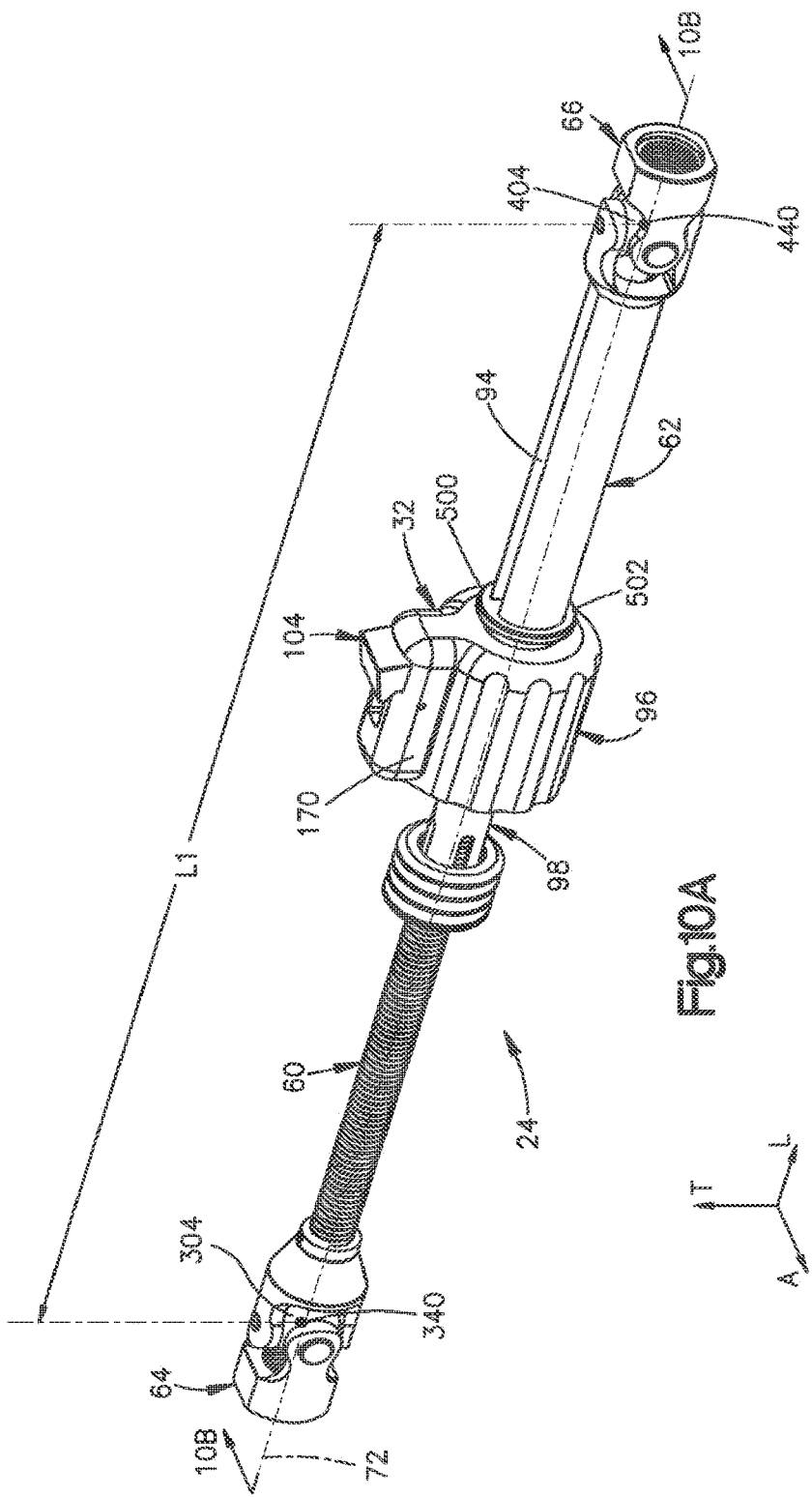

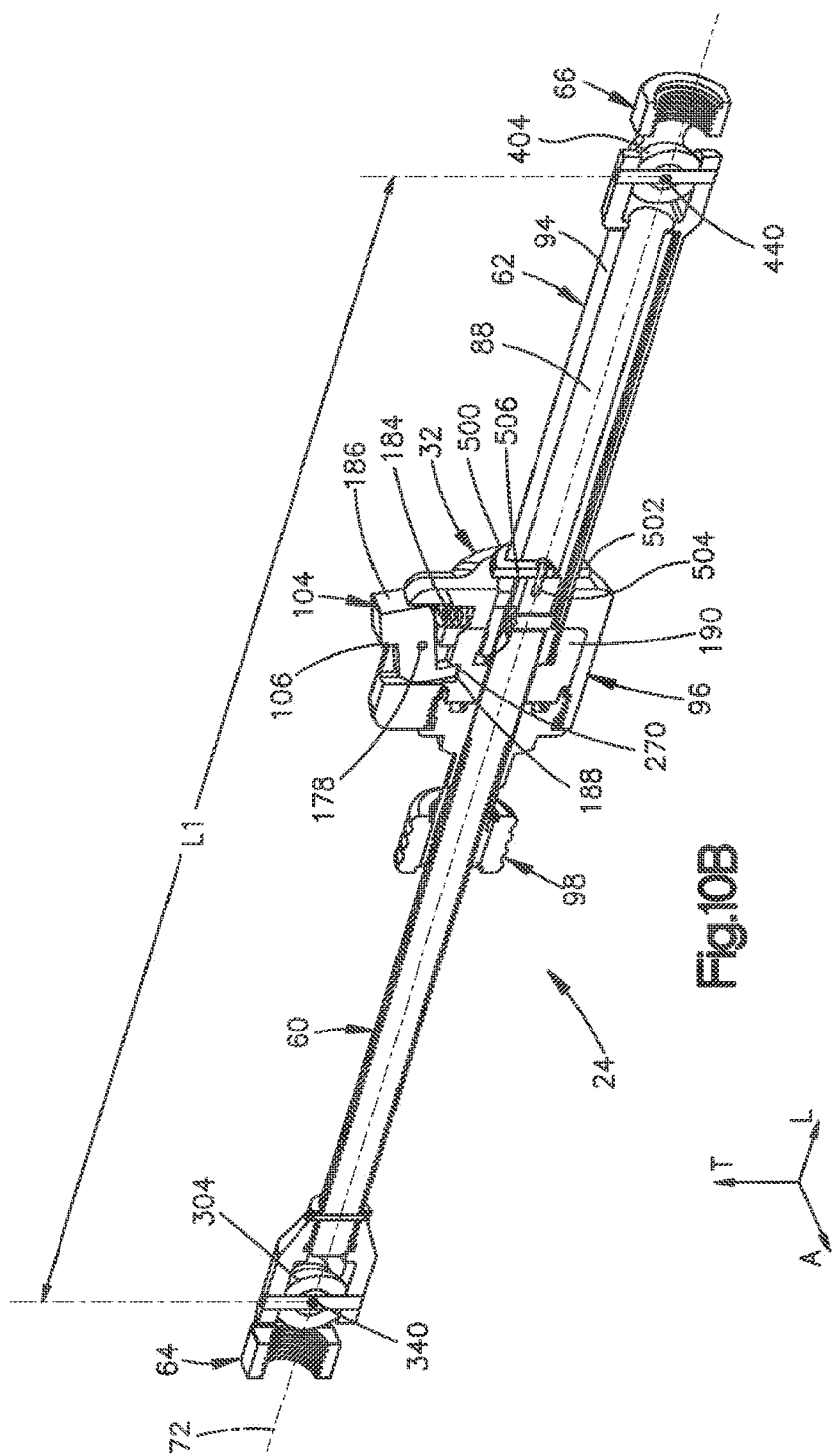

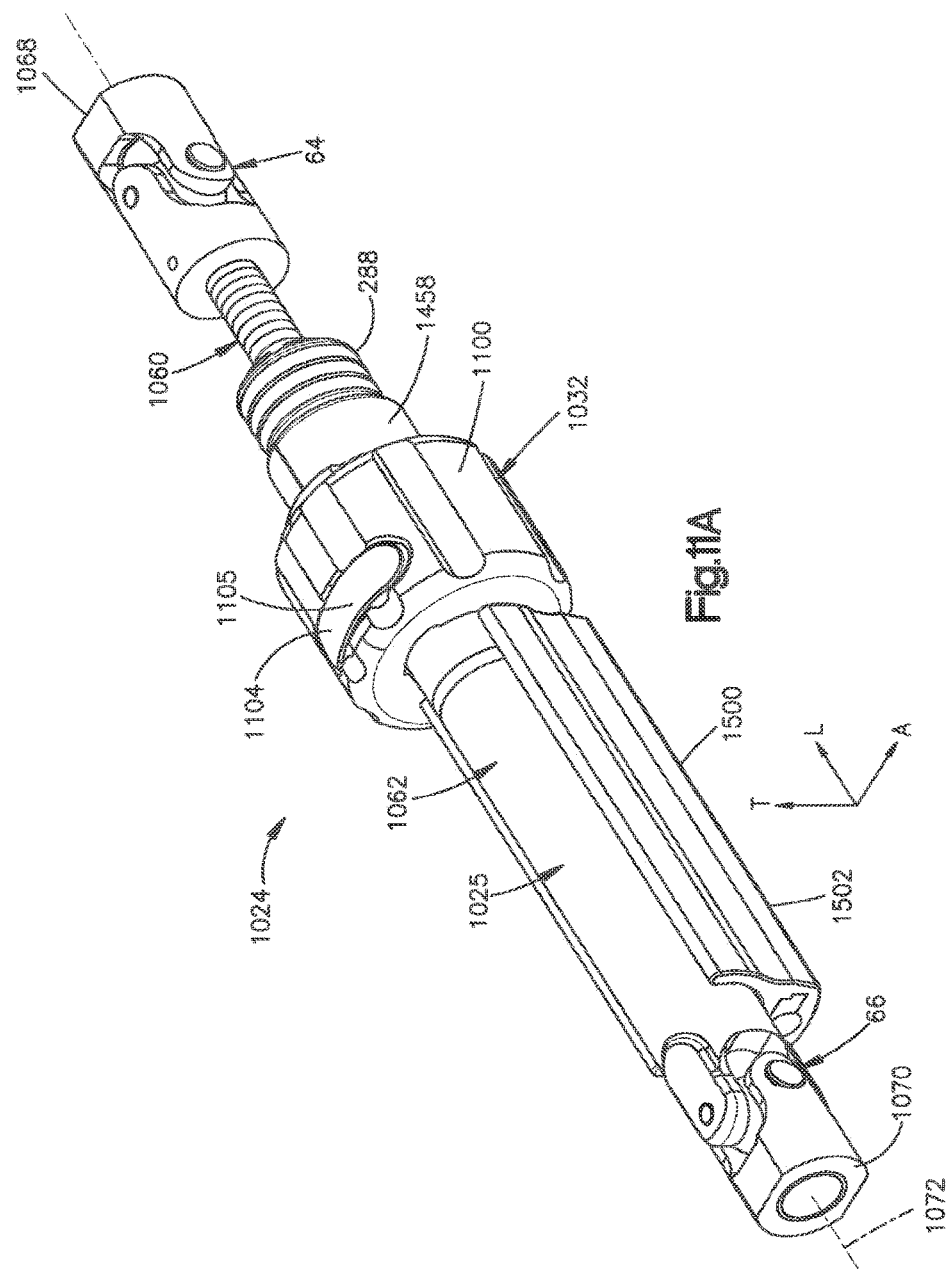

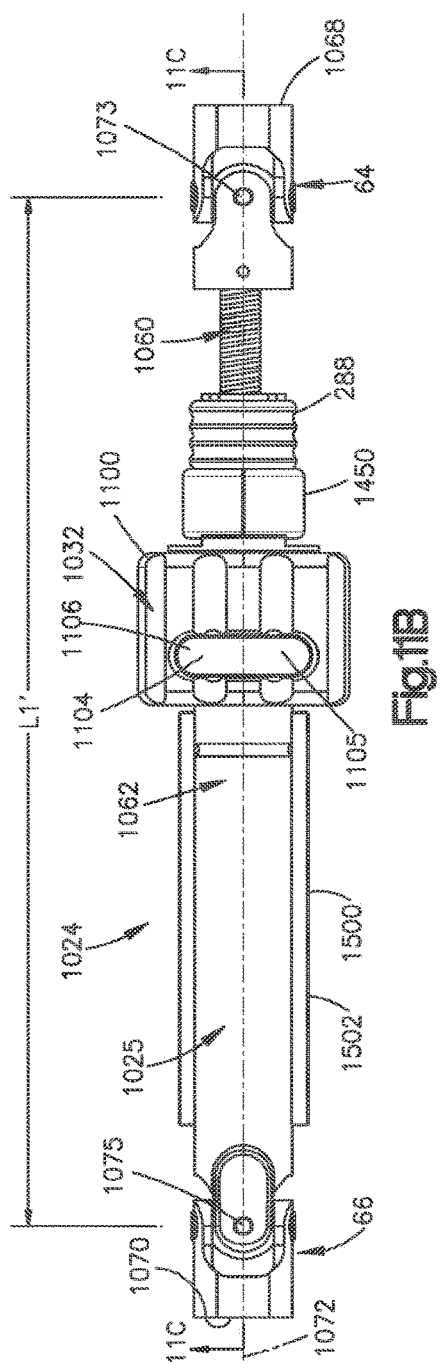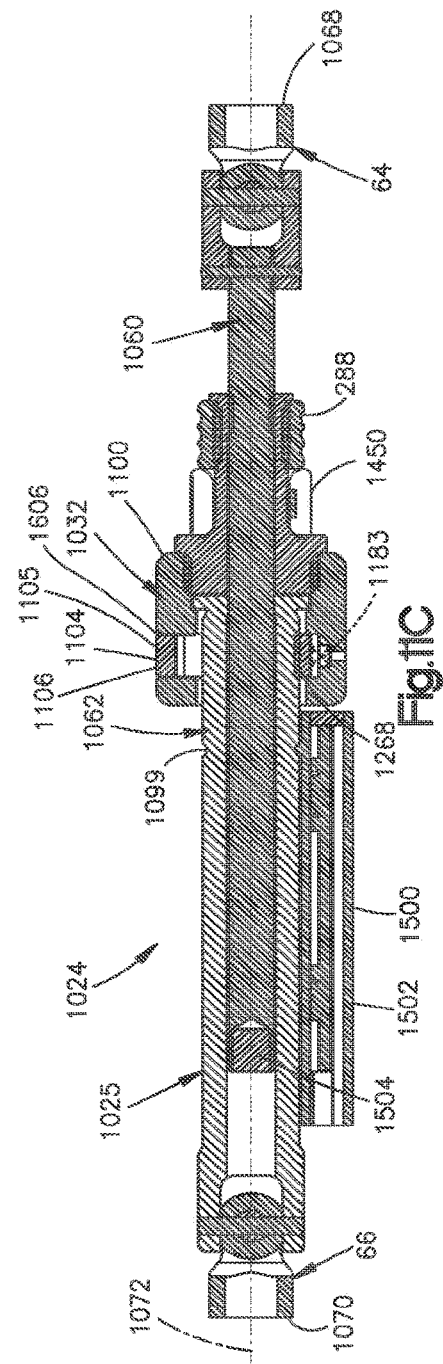

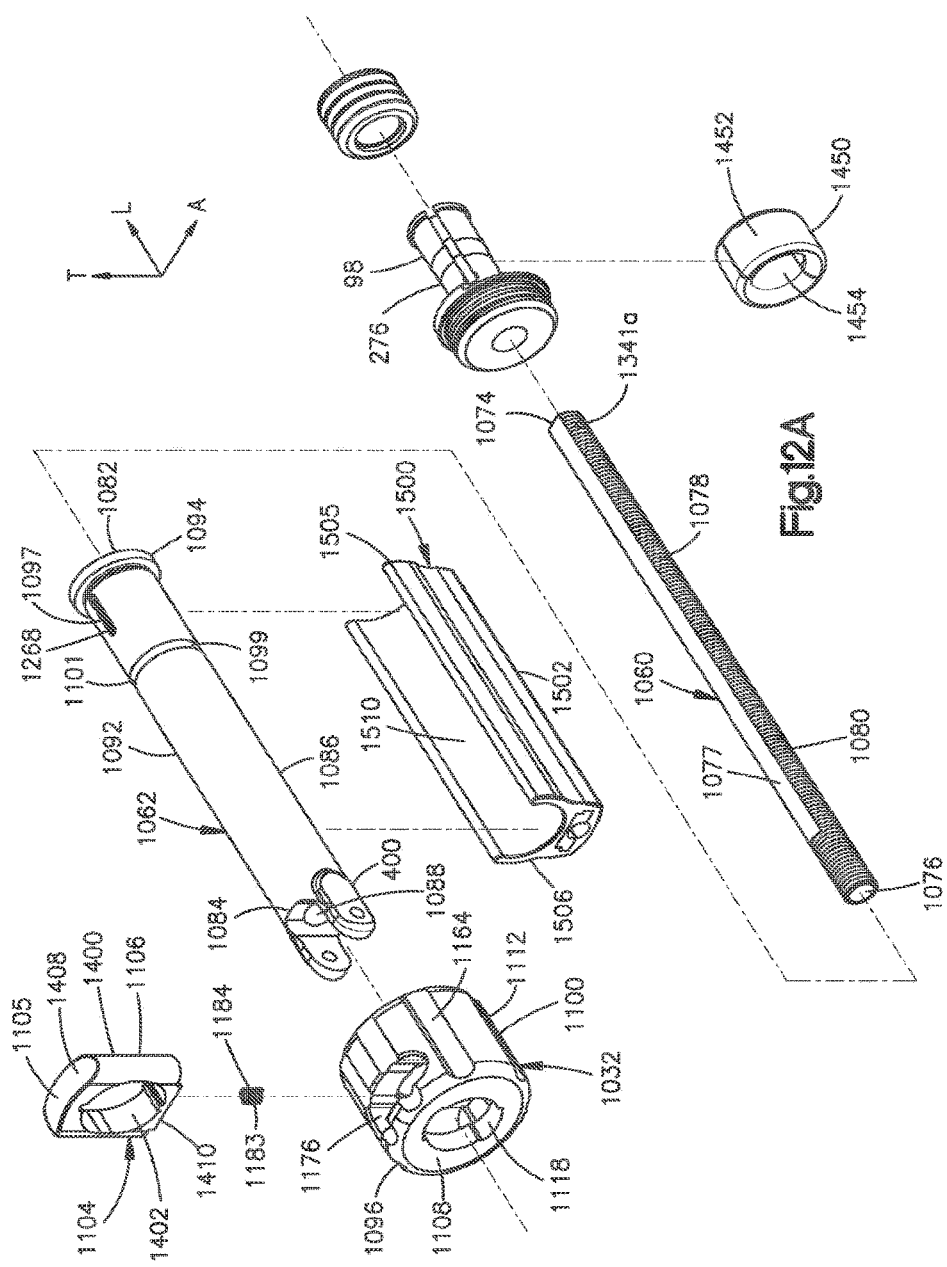

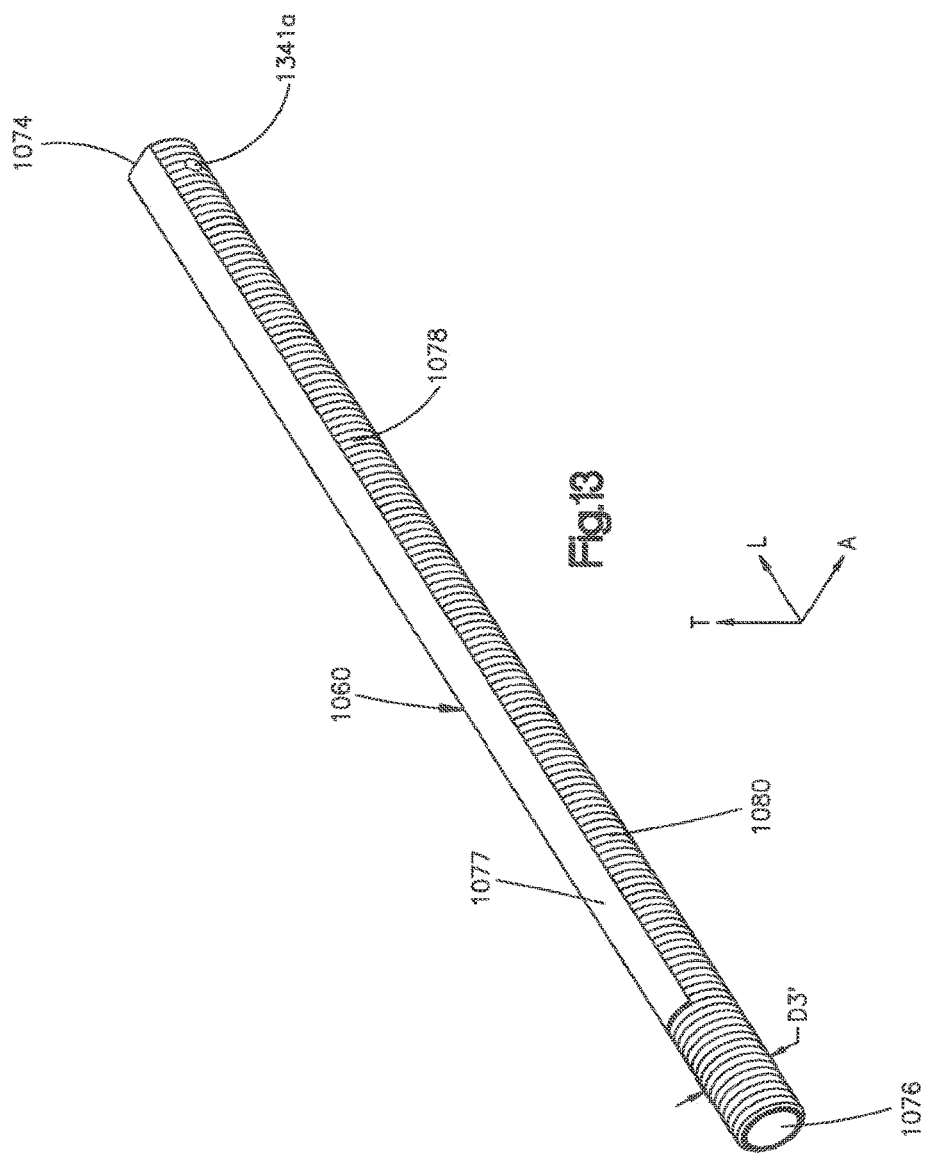

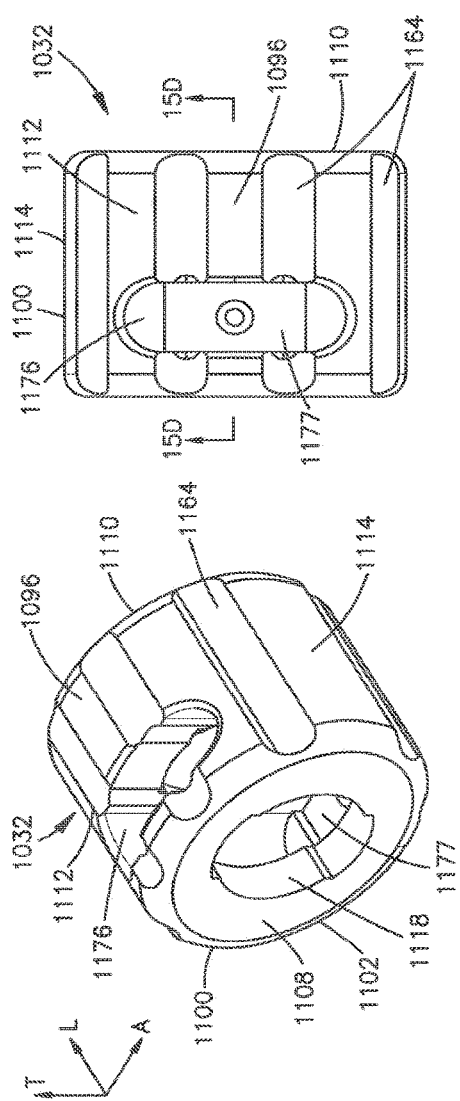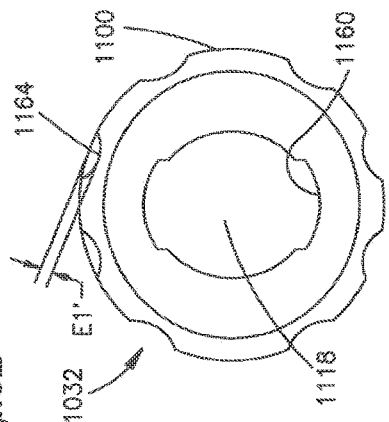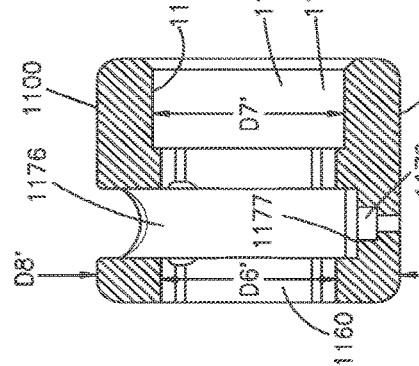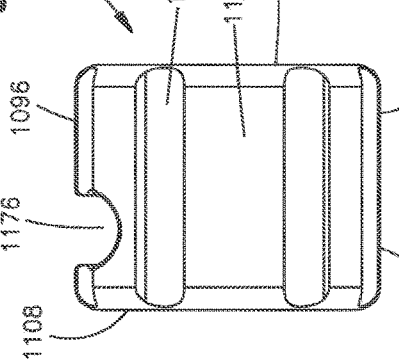

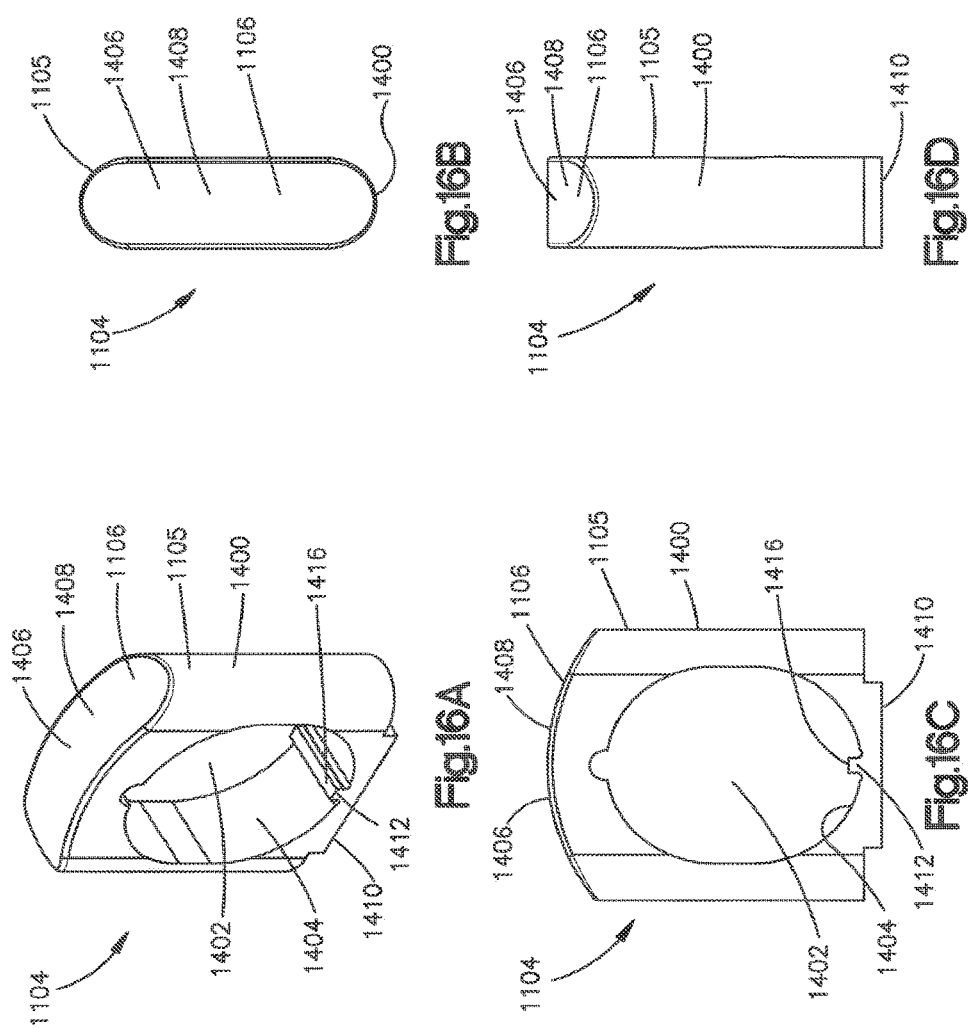

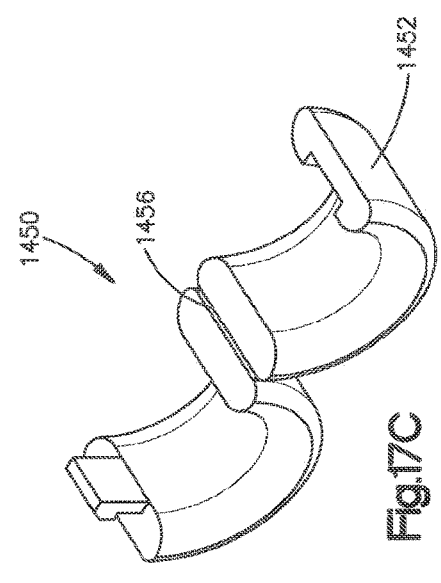
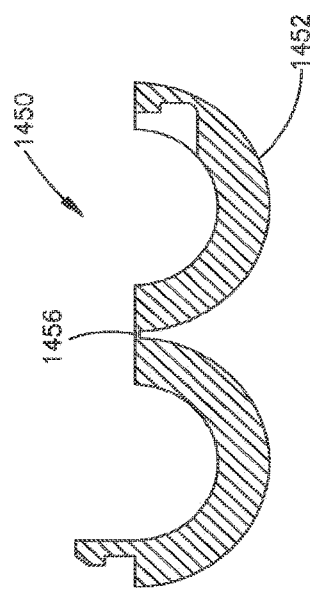
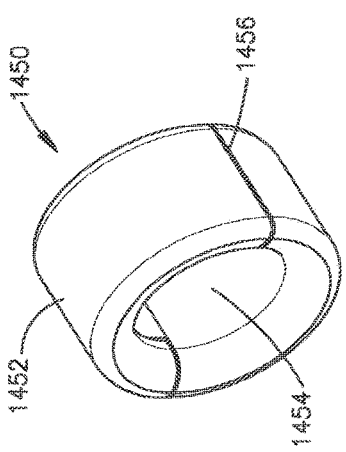
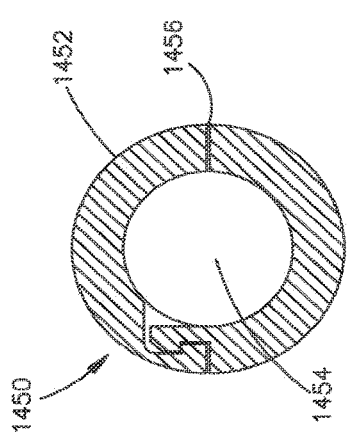

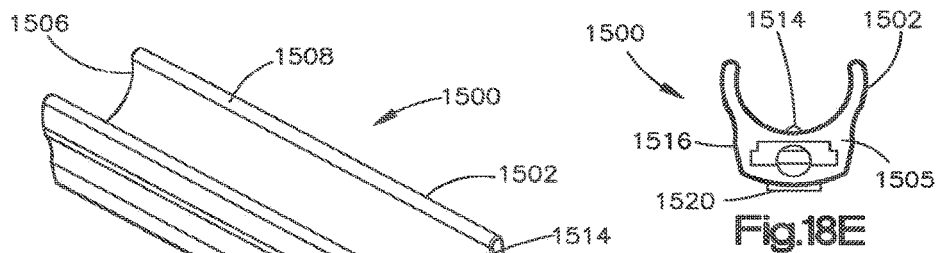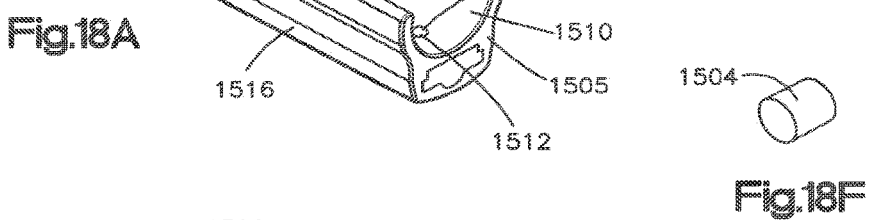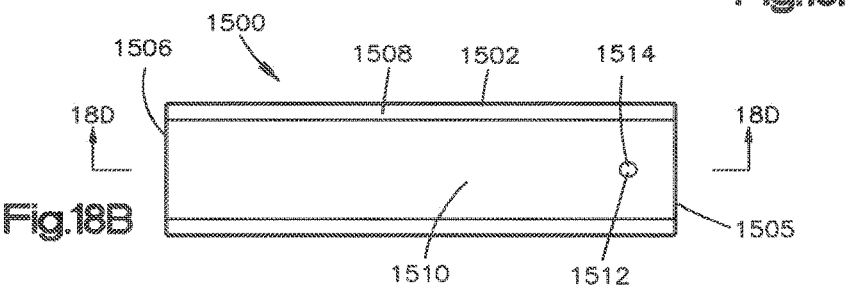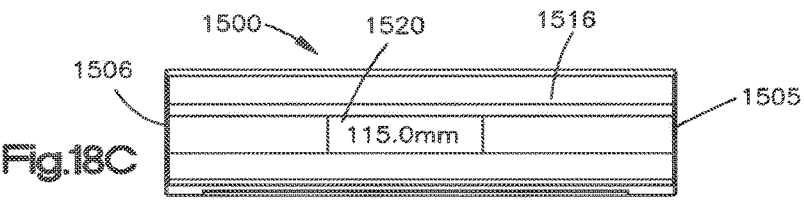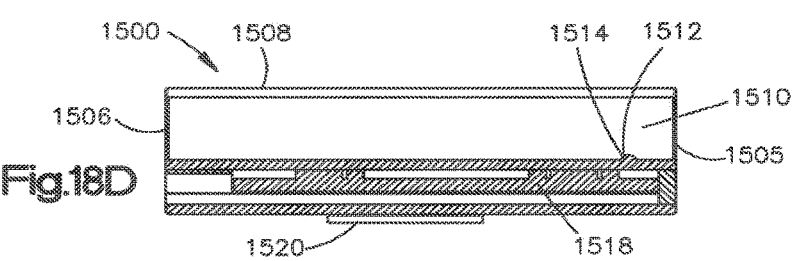

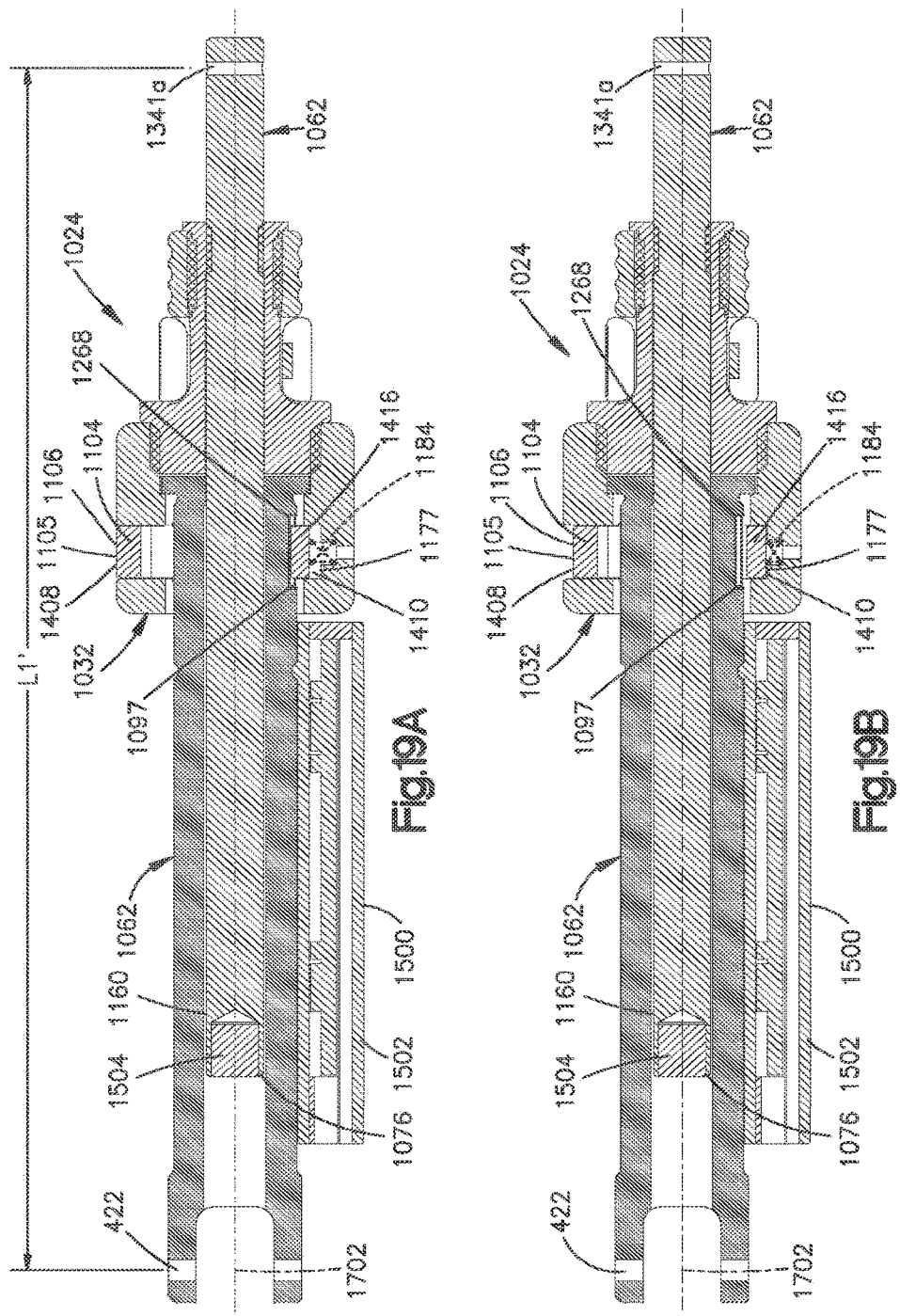

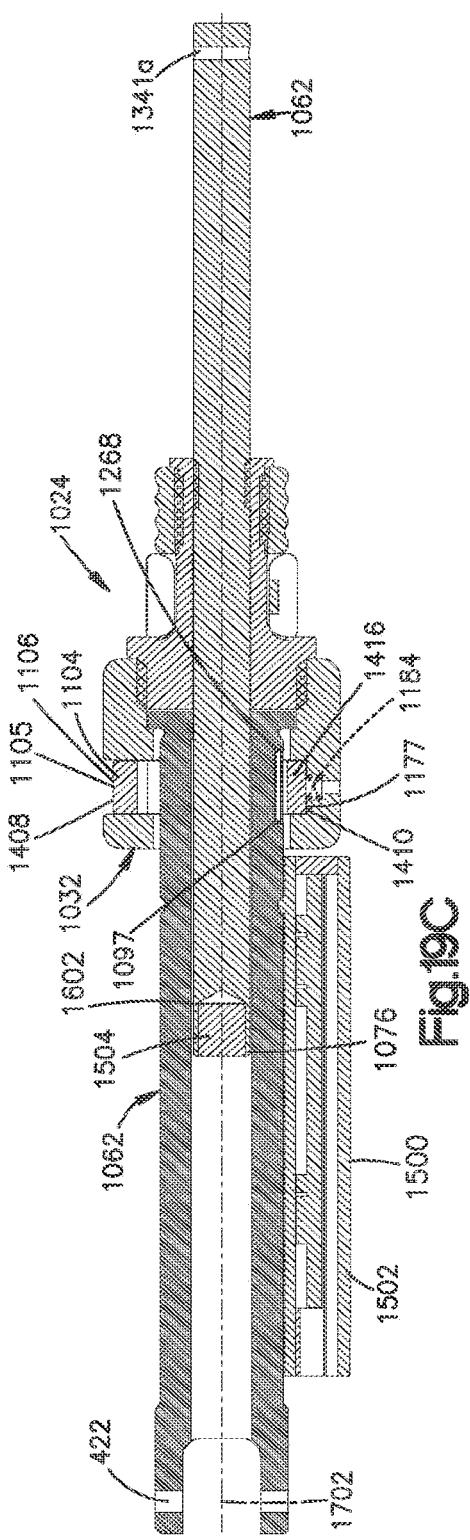

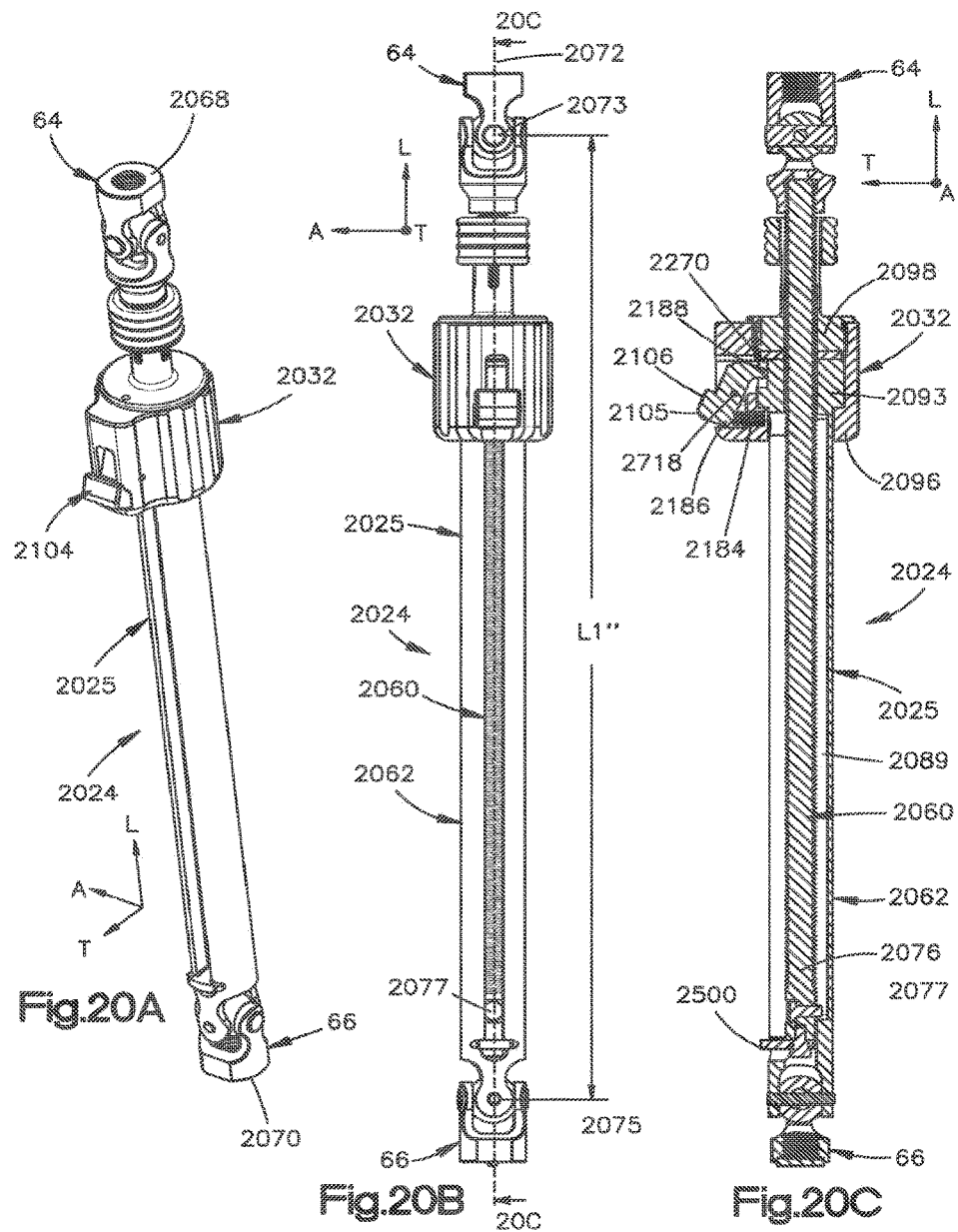

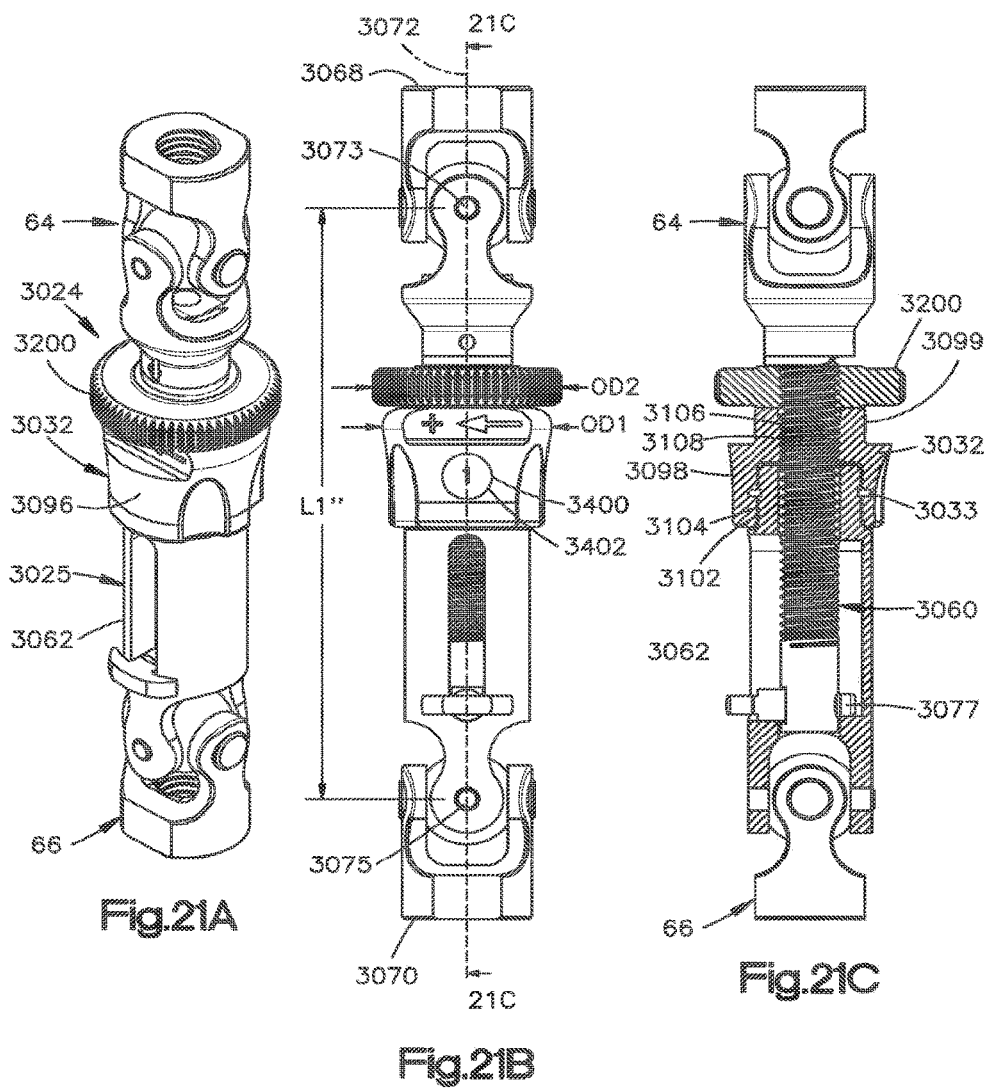

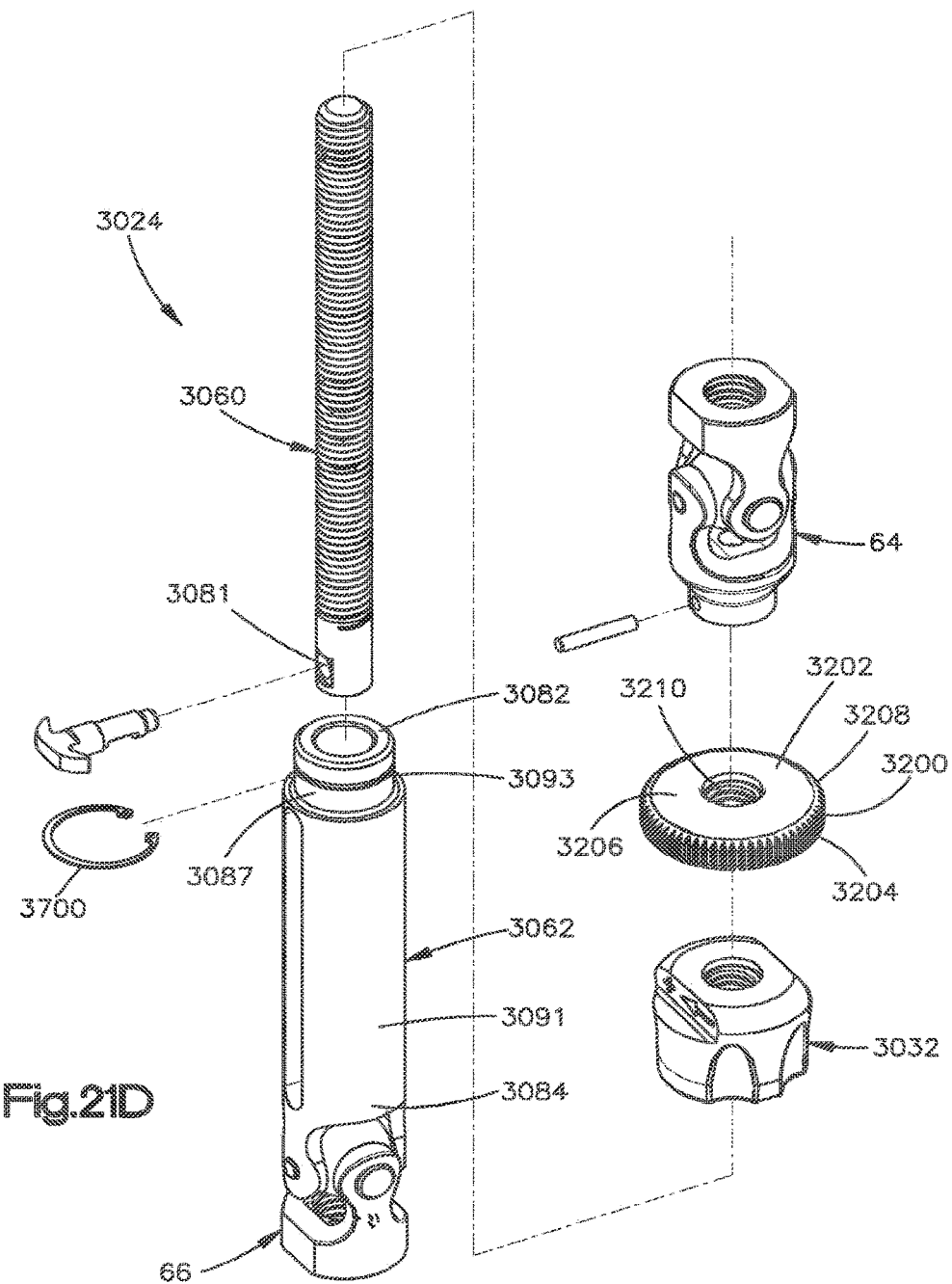

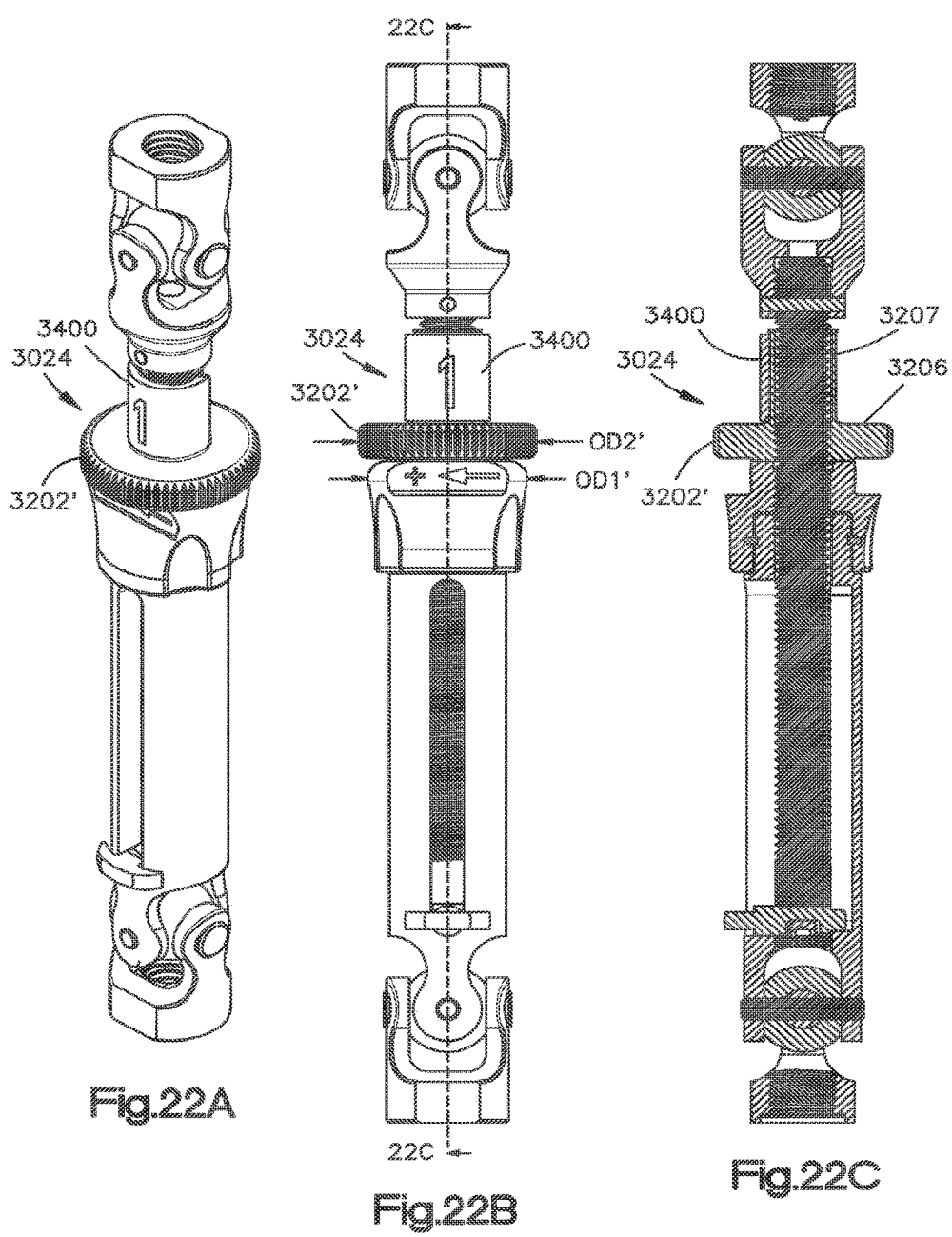

EXTERNAL BONE FIXATION DEVICE

CROSS-REFERENCE TO RELATED APPLICATIONS

This application is a continuation of U.S. patent application Ser. No. 14/774,374, filed Sep. 10, 2015, now U.S. Pat. No. 9,675,382 issued Jun. 13, 2017, which is a National Stage Application filed under 35 U.S.C. 371 of International Application No. PCT/US2014/025263, filed Mar. 13, 2014, which is a continuation-in-part of U.S. patent application Ser. No. 13/800,545, filed Mar. 13, 2013, now U.S. Pat. No. 8,864,763 issued Oct. 21, 2014, and a continuation-in-part of U.S. patent application Ser. No. 13/800,319, filed Mar. 13, 2013, now U.S. Pat. No. 9,039,706 issued May 26, 2015, the disclosures of which are hereby incorporated by reference as if set forth in their entireties herein.

TECHNICAL FIELD

The present application relates generally to orthopedics. More specifically, the present application relates to a device and method for the repair of fractures or deformities in long bones.

BACKGROUND

External bone fixation devices are used to stabilize bone segments and to facilitate the healing of bones at a bone repair site. A bone repair site can include a location of a deformity in a bone or an area of injury to a bone. Distraction and reduction/compression devices may be incorporated into an external bone fixation device and may be used to gradually adjust the relative orientation and spacing of portions of the bone on opposite sides of a bone repair site.

An external bone fixation device can include a number of support members configured to be connected to the portions of the bone on opposite sides of the bone repair site, as well as a number of distraction and reduction/compression devices configured to adjust the distance between the support members of the external bone fixation device that are attached to the bone portions on opposite sides of the bone repair site. The distraction devices are configured to move the support members gradually over a determined amount of time. The gradual separation allows new bone to form in the void of the bone repair site. In other cases, reduction or compression across a bone repair site to hold the bone portions together is desired to facilitate healing. Such adjustments, whether distraction or reduction/compression, typically follow a prescribed protocol, or treatment plan. After each adjustment, the distraction and reduction/compression device is typically held fixed for a time allowing the new bone to grow and gain strength. After the bone repair site has healed, the external bone fixation device is removed from the bone portions.

SUMMARY

Various embodiments and methods of an external bone fixation device (and the components of the external bone fixation device) used to stabilize bone segments and to facilitate the healing of bones at a bone repair site are disclosed. In one embodiment, the device includes a strut configured to be connected to a pair of external bone fixation members along a strut axis. The strut includes a strut body having a threaded rod and a sleeve. The threaded rod includes a rod body that is elongate along the strut axis. The rod body defines an outer surface that is at least partially threaded, and the sleeve includes a sleeve body and a bore that extends at least into the sleeve body. The bore is configured to receive at least a portion of the threaded rod such that the threaded rod is translatable relative to the sleeve along the strut axis. The strut further includes an actuator supported by the strut body and threadedly attached to the threaded rod, such that rotation of the actuator relative to the rod about the strut axis translates at least one or both of the rod and the sleeve relative to the other of the rod and the sleeve along the strut axis. The strut further includes a locking mechanism supported by the strut body so as to be pivotal relative to the strut body about a pivot axis between a locked configuration whereby the locking mechanism prevents the actuator from rotating relative to the threaded rod, and an unlocked configuration whereby the locking mechanism does not prevent the actuator from rotating relative to the threaded rod, and the pivot axis is angularly offset with respect to the strut axis.

In another embodiment, a strut configured to be connected to a pair of external bone fixation members along a strut axis includes a strut body having a threaded rod and a sleeve, the threaded rod including a rod body that is elongate along the strut axis, and the rod body defining an outer surface that is at least partially threaded. The sleeve has a sleeve body and a bore that extends at least into the sleeve body, the bore configured to receive at least a portion of the threaded rod such that the threaded rod is translatable relative to the sleeve along the strut axis. The strut further includes an actuator supported by the strut body and threadedly attached to the threaded rod, such that rotation of the actuator relative to the rod about the strut axis translates at least one or both of the rod and the sleeve relative to the other of the rod and the sleeve along the strut axis. The actuator includes a gripping member that is configured to receive a torque that rotates the actuator relative to the threaded rod about the strut axis. The gripping member includes a body and a bore that extends through the body, the body having an inner surface that at least partially defines the bore and an outer surface opposite the inner surface. The bore is configured to at least partially receive the strut body, and the gripping member further includes a projection that is fixed to the gripping member body and extends out from the outer surface of the gripping member body in a direction away from the inner surface of the gripping member body.

In another embodiment, a strut configured to be connected to a pair of external bone fixation members along a strut axis includes a strut body having a threaded rod and a sleeve, the threaded rod including a rod body that is elongate along the strut axis, and defines an outer surface that is at least partially threaded. The sleeve includes a sleeve body and a bore that extends at least into the sleeve body, the bore configured to receive at least a portion of the threaded rod such that the threaded rod is translatable relative to the sleeve along the strut axis. The strut further includes an actuator supported by the strut body and threadedly attached to the threaded rod, such that rotation of the actuator relative to the rod about the strut axis translates at least one or both of the rod and the sleeve relative to the other of the rod and the sleeve along the strut axis. The strut further includes a joint configured to attach to one of the external bone fixation members, the joint including a first hinge body supported by the threaded rod, a second hinge body configured to attach to the external bone fixation member, and a cross coupling member configured to couple the first hinge body to the second hinge body such that first hinge body is rotatable relative to second hinge body about both a first axis that is angularly offset with respect to the strut axis, and a second axis that is angularly offset with respect to both the first axis and the strut axis. Wherein the cross coupling member is substantially spherical.

In another embodiment, a strut configured to be connected to a pair of external bone fixation members along a strut axis includes a strut body having a threaded rod and a sleeve, the threaded rod including a rod body that is elongate along the strut axis and defines an outer surface that is at least partially threaded. The sleeve includes a sleeve body and a bore that extends at least into the sleeve body, and the bore is configured to receive at least a portion of the threaded rod such that the threaded rod is translatable relative to the sleeve along the strut axis. The strut further includes an actuator supported by the strut body and threadedly attached to the threaded rod, such that rotation of the actuator relative to the rod about the strut axis translates at least one or both of the rod and the sleeve relative to the other of the rod and the sleeve along the strut axis. The strut further includes a locking mechanism supported by the strut body so as to be pivotal relative to the strut body about a pivot axis between a locked configuration whereby the locking mechanism prevents the actuator from rotating relative to the threaded rod in response to an applied torque, and an unlocked configuration whereby the locking mechanism does not prevent the actuator from rotating relative to the threaded rod in response to the applied torque. Wherein the locking mechanism includes a lever the lever that defines a first surface, and the strut body defines a second surface that interferes with the first surface so as to prevent rotation of the actuator relative to the threaded rod about the strut axis when the locking mechanism is in the locked configuration, the first and second surfaces oriented such that the first and second surfaces do not cam over one another in response to the applied torque.

In another embodiment, a strut configured to be connected to a pair of external bone fixation members along a strut axis includes a threaded rod having a rod body that is elongate along the strut axis, the rod body defining an outer surface that is at least partially threaded. The strut further has a sleeve including a sleeve body, the sleeve body defining an inner surface that defines a bore that extends at least into the sleeve body and is configured to receive a portion of the rod body. The strut further having an actuator threadedly attached to the threaded rod and rotatably supported by the sleeve. Wherein one of the inner surface and the rod body supports a track that is elongate along a direction parallel to the strut axis, and the other of the inner surface and the rod body fixedly supports a follower configured to ride along the track such that the treaded rod translates with respect to the sleeve along the strut axis when the actuator is rotated with respect to the sleeve and the threaded rod.

In another embodiment, a strut configured to be connected to a pair of external bone fixation members along a strut axis includes a threaded rod including a rod body that is elongate along the strut axis, the rod body defining an outer surface that is at least partially threaded, the outer surface defining a cross-sectional shape with respect to a direction parallel to the strut axis, the cross-sectional shape being non-circular, and a sleeve including a sleeve body and a bore that extends at least into the sleeve body, the sleeve body defining an inner surface that defines the bore, the inner surface defining at opening of the bore, the opening defining a cross-sectional shape with respect to the direction, the cross-sectional shape of the opening corresponding to the cross-sectional shape of the outer surface such that the opening is configured to receive a portion of the rod body and prevent the threaded rod from rotating relative to the sleeve. The strut further includes an actuator threadedly attached to the threaded rod and rotatably supported by the sleeve, wherein when the portion of the rod body is inserted into the opening of the threaded rod, actuation of the actuator causes at least one or both of the threaded rod and the sleeve to translate relative to the other of the threaded rod and the sleeve along the strut axis.

In another embodiment, a strut configured to be connected to a pair of external bone fixation members along a strut axis includes a strut body having a threaded rod and a sleeve, the threaded rod including a rod body that is elongate along the strut axis, the rod body defining an outer surface that is at least partially threaded, and the sleeve including a sleeve body and a bore that extends at least into the sleeve body, the bore configured to receive at least a portion of the threaded rod such that the threaded rod is translatable relative to the sleeve along the strut axis. The strut further includes an actuator supported by the sleeve and threadedly attached to the threaded rod, such that rotation of the actuator relative to the threaded rod about the strut axis causes at least one or both of the threaded rod and the sleeve to translate relative to the other of the threaded rod and the sleeve along the strut axis, and a locking mechanism supported by the threaded rod so as to be translatable relative to the actuator along the strut axis between a locked configuration whereby the locking mechanism prevents the actuator from rotating relative to the threaded rod, and an unlocked configuration whereby the locking mechanism does not prevent the actuator from rotating relative to the threaded rod, wherein when the actuator is supported by the sleeve and when the locking mechanism is supported by the threaded rod, the actuator defines a first maximum cross-sectional dimension with respect to a direction parallel to the strut axis, and the locking mechanism defines a second maximum cross-sectional dimension with respect to the direction, the second maximum cross-sectional dimension being greater than the first maximum cross-sectional dimension.

In another embodiment, a method of assembling an external bone fixation device configured to repair a deformity in a bone is disclosed. The external bone fixation device includes first and second external bone fixation members, and a strut that has a first joint configured to be attached to the first external bone fixation member, and a second joint spaced from the first joint along a strut axis, the second joint configured to be attached to the second external bone fixation member. The method comprises the steps of positioning the strut relative to the first external bone fixation member such that a first fastener receiving hole of the first joint is aligned with a second fastener receiving hole of the first external bone fixation member, inserting a first fastener at least into the first fastener receiving hole and the second fastener receiving hole so as to attach the first joint to the first external bone fixation member, rotating the strut relative to the first external bone fixation member about the strut axis to a predetermined orientation, aligning a third fastener receiving hole of a second joint of the strut with a fourth fastener receiving hole of the second external bone fixation member, and inserting a second fastener at least into the third fastener receiving hole and the fourth fastener receiving hole so as to attach the second joint to the second external bone fixation member, such that each of the first and second joints is rotatably fixed with respect to both of the first and second external bone fixation members about the strut axis.

In another embodiment, a method of assembling an external bone fixation device configured to repair a deformity in a bone is disclosed. The device includes a strut having a first joint, a second joint, and a length measured from the first joint to the second joint along a strut axis. The first and second joints define first and second fastener receiving holes respectively, and the strut further includes an actuator configured to adjust the length and a locking mechanism configured to be supported by the actuator. The locking mechanism can be movable between a locked configuration in which the actuator is prevented from adjusting the length, and an unlocked configuration in which the actuator is able to adjust the length. The first and second external bone fixation members each include a top surface and a bottom surface. The first and second external fixation members each further including a fastener receiving hole extending from the top surface to the bottom surface, and the first external fixation member defines a center and a radial outward direction that extends from the center to the fastener receiving hole of the first external bone fixation member.

The method includes the step of positioning the strut relative to the first external bone fixation member such that the fastener receiving hole of the first joint is aligned with the fastener receiving hole of the first external fixation member. The method further includes the step of inserting a first fastener into and at least partially through the fastener receiving hole of the first joint and the fastener receiving hole of the first external bone fixation member. The method further includes the step of rotating the actuator about the strut axis such relative to the fastener receiving hole of the first external bone fixation member such that the locking member is spaced from the strut axis in the radial outward direction. The method further includes the step of positioning the strut relative to the second external bone fixation member such that the fastener receiving hole of the second joint is aligned with the fastener receiving hole of the second external fixation member. The method further includes the step of inserting a second fastener into and at least partially through the fastener receiving hole of the second joint and the fastener receiving hole of the second external bone fixation member, such that after the step of inserting of the second fastener through the fastener receiving holes of the second external fixation member and the second joint, the actuator is not rotatable relative to the fastener receiving hole of the first external bone fixation member about the strut axis when the locking mechanism is in the locked configuration.

BRIEF DESCRIPTION OF THE DRAWINGS

The foregoing summary, as well as the following detailed description of illustrative embodiments of the external bone fixation device of the present application, will be better understood when read in conjunction with the appended drawings. For the purposes of illustrating the external bone fixation device of the present application, there is shown in the drawings illustrative embodiments. It should be understood, however, that the application is not limited to the precise arrangements and instrumentalities shown. In the drawings:

FIG. 1A is a perspective view of an external bone fixation device in a first configuration, positioned proximate a fractured bone, the external bone fixation device including a plurality of bases and a plurality of struts;

FIG. 2A is a perspective view of one of the plurality of bases illustrated in FIG. 1A, according to one embodiment;

FIG. 2B is a top plan view of the base illustrated in FIG. 2A;

FIG. 2C is a top plan view of the one of the plurality of bases illustrated in FIG. 2A, according to another embodiment;

FIG. 3A is a perspective view of one of the plurality of bases illustrated in FIG. 1A, according to another embodiment;

FIG. 3B is a perspective view of the one of the plurality of bases illustrated in FIG. 3A, according to another embodiment;

FIG. 5B is a top plan view of the strut illustrated in FIG. 5A;

FIG. 5C is a cross-sectional side view of the strut illustrated in FIG. 5B along line 5C-5C;

FIG. 6A is an exploded perspective view of the strut illustrated in FIG. 5A;

FIG. 7A is a perspective view of a gripping member of the actuator illustrated in FIG. 5A;

FIG. 7B is a side elevation view of the gripping member illustrated in FIG. 7A;

FIG. 7C is a top plan view of the gripping member illustrated in FIG. 7A;

FIG. 7D is a front elevation view of the gripping member illustrated in FIG. 7A;

FIG. 9A is a perspective view of the actuator illustrated in FIG. 5A;

FIG. 10A is a perspective view of the strut illustrated in FIG. 5A, in a second configuration;

FIG. 10B is a cross-sectional view of the strut illustrated in FIG. 10A along line 10B-10B;

FIG. 11A is a perspective view of one of the plurality of struts illustrated in FIG. 1A, according to another embodiment, the strut including an actuator, a threaded rod, a sleeve, a first joint, a second joint, and a measurement device;

FIG. 11B is a top plan view of the strut illustrated in FIG. 11B;

FIG. 11C is a cross-sectional side view of the strut illustrated in FIG. 11B, along line 11C-11C.

FIG. 12A is an exploded perspective view of the strut illustrated in FIG. 11A;

FIG. 13 is a perspective view of the threaded rod illustrated in FIG. 11A;

FIG. 15A is a perspective view of a gripping member of the actuator illustrated in FIG. 11A;

FIG. 15B is a top plan view of the gripping member illustrated in FIG. 15A;

FIG. 15C is a side elevation view of the gripping member illustrated in FIG. 15A;

FIG. 15D is a side cross-sectional view of the gripping member illustrated in 15A along line 15D-15D;

FIG. 15E is a front elevation view of the gripping member illustrated in FIG. 15A;

FIG. 16A is a perspective view of a portion of the locking mechanism of the actuator illustrated in FIG. 11A;

FIG. 16B is a top plan view of the portion of the locking mechanism illustrated in FIG. 16A;

FIG. 16C is a front elevation view of the portion of the locking mechanism illustrated in FIG. 16A;

FIG. 16D is a side elevation view of the portion of the locking mechanism illustrated in FIG. 16D;

FIG. 17A is a perspective view of a collar the strut illustrated in FIG. 11A, in a closed configuration;

FIG. 17B is a front cross-sectional view of the collar illustrated in FIG. 17A along line 17B-17B, in the closed configuration;

FIG. 17C is a perspective view of the collar illustrated in FIG. 17A, in an open configuration;

FIG. 17D is a front cross-sectional view of the collar illustrated in FIG. 17A along line 17B-17B, in the open configuration;

FIG. 18A is a perspective view of a sensor of the measurement device illustrated in FIG. 11A;

FIG. 18B is a top plan view of the sensor illustrated in FIG. 18A;

FIG. 18C is a bottom plan view of the sensor illustrated in FIG. 18A;

FIG. 18D is a side cross-sectional view of the sensor illustrated in FIG. 18B along line 18C-18C;

FIG. 18E is a front elevation view of the sensor illustrated in FIG. 18A;

FIG. 18F is a perspective view of a marker of the measurement device illustrated in FIG. 11A;

FIG. 19A is a side cross-sectional view of the strut illustrated in FIG. 11B along line 11C-11C, the strut in a locked configuration and having a first length;

FIG. 19B is a side cross-sectional view of the strut illustrated in FIG. 11B along line 11C-11C, the strut in an unlocked configuration and having the first length;

FIG. 19C is a side cross-sectional view of the strut illustrated in FIG. 11B along line 11C-11C, the strut in an unlocked configuration and having a second length;

FIG. 20A is a perspective view of one of the plurality of struts illustrated in FIG. 1A, according to another embodiment, the strut including an actuator, a threaded rod, a sleeve, a first joint, and a second joint;

FIG. 20B is a top plan view of the strut illustrated in FIG. 20A;

FIG. 20C is a cross-sectional view of the strut illustrated in FIG. 20B along line 20C-20C;

FIG. 21A is a perspective view of one of the plurality of struts illustrated in FIG. 1A, according to another embodiment, the strut including an actuator, a threaded rod, a sleeve, a first joint, and a second joint;

FIG. 21B is a top plan view of the strut illustrated in FIG. 21A;

FIG. 21C is a side cross-sectional view of the strut illustrated in FIG. 21B along line 21C-21C;

FIG. 21D is an exploded perspective view of the strut illustrated in FIG. 21A;

FIG. 22A is a perspective view of one of the plurality of struts illustrated in FIG. 1A, according to another embodiment, the strut including an actuator, a threaded rod, a sleeve, a first joint, and a second joint;

FIG. 22B is a top plan view of the strut illustrated in FIG. 22A;

FIG. 22C is a side cross-sectional view of the strut illustrated in FIG. 22B along line 22C-22C;

DETAILED DESCRIPTION OF ILLUSTRATIVE EMBODIMENTS

Figure 1B:
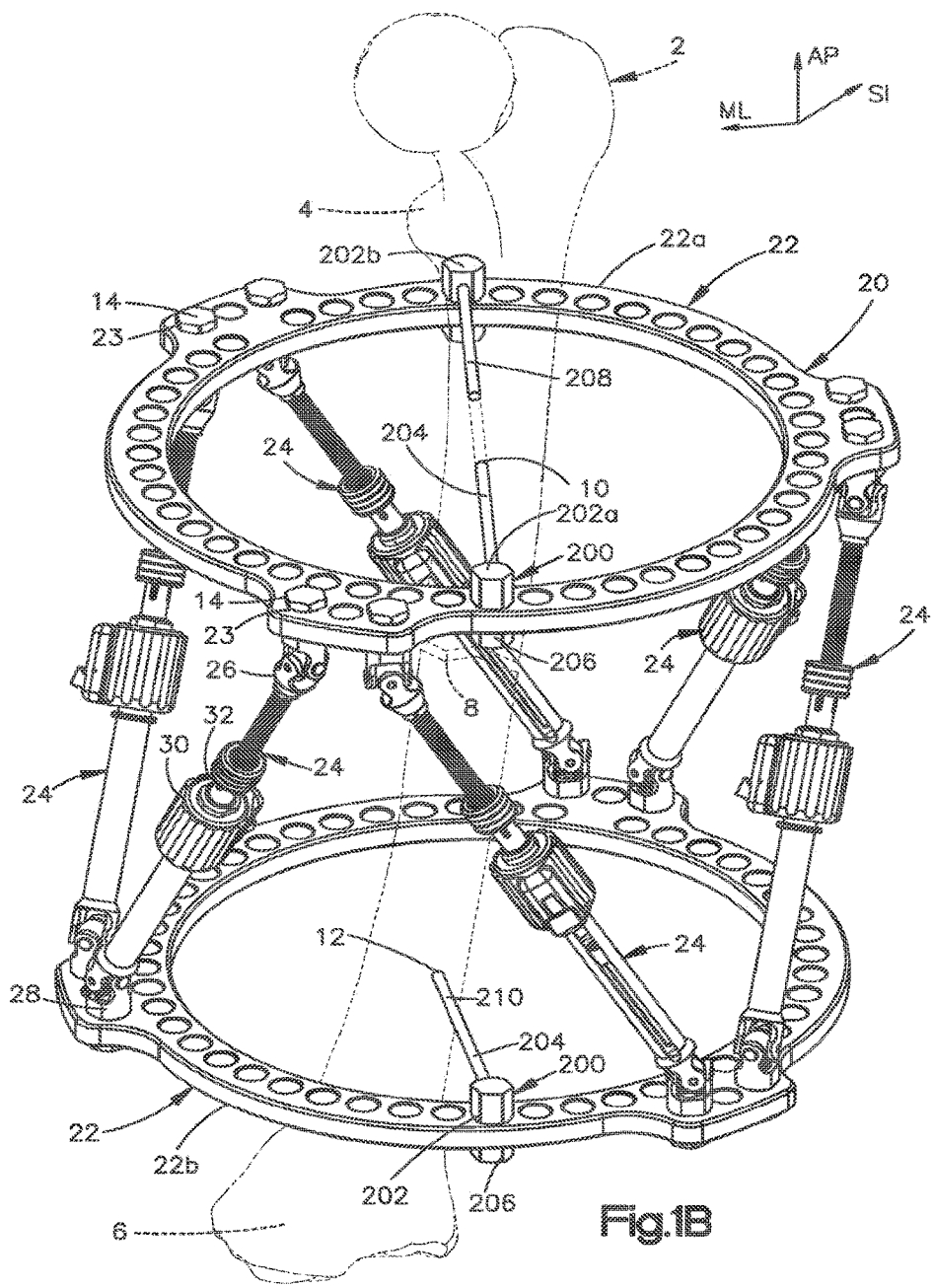
FIG. 1B is a perspective view of the external bone fixation device illustrated in FIG. 1A in a second configuration positioned proximate the fractured bone.

Certain terminology is used in the following description for convenience only and is not limiting. The words "right", "left", "lower", "upper", "bottom", and "top" designate directions in the drawings to which reference is made. The words, "anterior", "posterior", "superior", "inferior", "medial", "lateral" and related words and/or phrases designate preferred positions and orientations in the human body to which reference is made. For example, the words "medially" and "laterally" refer to directions toward and away from, respectively, a midline extending vertically through a body. The words "proximal" and "distal" refer to directions toward or away from where an appendage, such as a leg, is joined to the rest of the body, respectively. The terminology includes the above-listed words, derivatives thereof and words of similar import.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. Further, reference to values stated in ranges includes each and every value within that range. All ranges are inclusive and combinable. Certain features of the invention which are described herein in the context of separate embodiments may also be provided in combination in a single embodiment. Conversely, various features of the invention that are described in the context of a single embodiment may also be provided separately or in any subcombination.

A three dimensional coordinate system is used to describe the positions and orientations of the parts of the external bone fixation device. The coordinate system includes a first direction, such as a longitudinal direction L; a second direction, such as a lateral direction A, and a third direction, such as a transverse direction T, wherein each of the directions is perpendicular to both of the other two directions.

Referring to FIGS. 1A and 1B, an external bone fixation device 20 (also referred to hereinafter as "device 20") is configured to be used to correct bone deformities, which can be anatomical deformities or bone injuries such as fractures. In one embodiment the external bone fixation device 20 can be used to treat a bone 2, for example a fractured long bone such as a femur. The bone 2 can include a first bone portion 4, such as a proximal portion, and a second bone portion 6, such as a distal portion. The first bone portion 4 and the second bone portion 6 can be separated by a defect, such as a fracture 8. The device 20 is configured to attach to the bone 2 at a first location 10 located on the first bone portion 4, and at a second location 12 located on the second bone portion 6. The device 20 is configured to move at least one or both of the first bone portion 4 and the second bone portion 6 relative to the other of the first bone portion 4 or the second bone portion 6, respectively, from a first position, such as a first orientation as shown in FIG. 1A, to a second position that is different from the first position, such as a second orientation different from the first orientation as shown in FIG. 1B, to align the first and second bone portions 4 and 6 so as to assist in correction the bone deformity of the bone 2.

As shown in the illustrated embodiment, the device 20 can include a plurality (e.g., a pair or more) of external bone fixation members, such as bases 22, that are each configured to be secured to respective bone portions, and at least one strut 24, such as a plurality of struts 24, that are configured to attach to at least a pair of the external bone fixation members at attachment locations 23. One or more fasteners 14, for example bolts or screws, can be used to secure the strut 24 relative to the base 22 at the attachment location 23. The external support members can attach to a bone fixation element 204 that is anchored in the respective bone portion. For instance, the external support member can be supported outboard of the epidermis that surrounds the bone portion, and the bone fixation element 204 can extend from the external support member, through the epidermis and soft tissue disposed between the epidermis and bone portion, and into the bone portion.

For example, the bases 22 can include a first base 22a and a second base 22b. The struts 24 can define respective distraction and reduction/compression devices (collectively referred to herein as "strut" or "struts" 24) configured to attach adjacent ones of the plurality of bases 22 such that the adjacent bases 22 are movable relative to one another. For instance, the struts 24 define a length between the attachment locations 23 that can be adjustable so as to cause at least one of the bases 22 to move relative to the other of the bases 22 at the respective attachment locations 23.

Figure 5A:
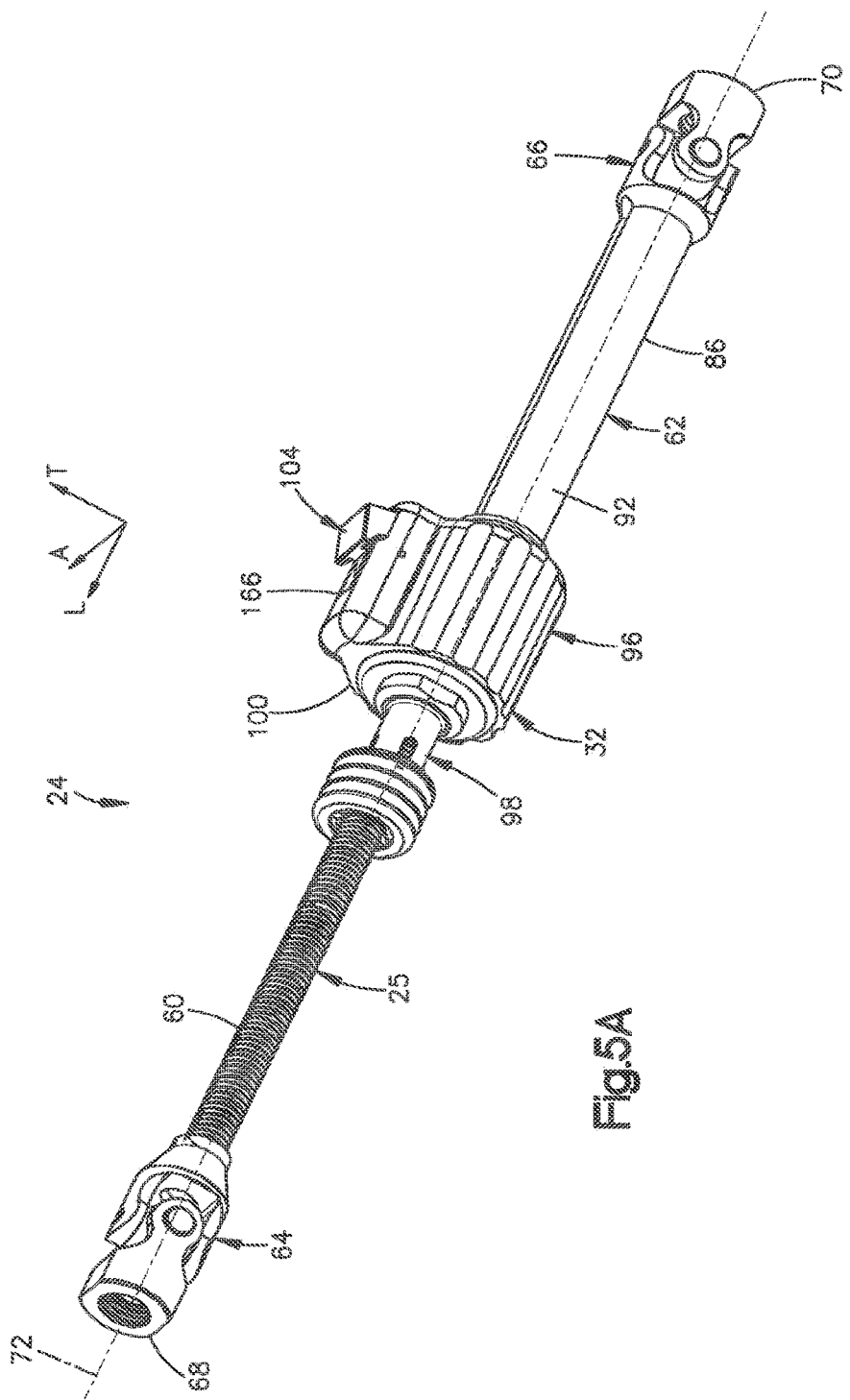
FIG. 5A is a perspective view of one of the plurality of struts illustrated in FIG. 1A, according to one embodiment, the strut including an actuator, a threaded rod, a sleeve, a first joint, and a second joint.

In particular, an increase of the length of the struts 24 can cause one of the attachment locations 23 to move away from the other of the attachment locations, a decrease of the length of the struts 24 can cause one of the attachment locations 23 to move toward the other of the attachment locations 23, and any adjustment of the length (increase or decrease) can cause at least one of the external fixation members to rotate relative to the other of the external fixation members. Each of the struts 24 includes a first end portion 26 configured to be attached to a first of the adjacent bases 22, for example the first base 22a at the attachment location 23, and a second end portion 28 configured to be attached to a second of the adjacent bases 22, for example the second base 22b at the attachment location 23. The struts 24 can further include a strut axis 72 (as shown in FIG. 5A), the strut axis 72 extends from the first end portion 26 to the second end portion 28 such that the strut 24 is elongate along the strut axis 72.

The strut 24 includes an intermediate portion 30 disposed between the first end portion 26 and the second end portion 28. The strut 24 can further include an actuator 32, such that when the actuator 32 is actuated, the first end portion 26 moves relative to the second end portion 28. In one embodiment, the intermediate portion 30 carries or supports the actuator 32, as shown. Actuation, for example rotation, of the actuator 32 of the strut 24 moves the first end portion 26 relative to the second end portion 28. When the first end portion 26 is attached to the first base 22a and the second end portion 28 is attached to the second base 22b, actuation of the actuator 32 moves the first end portion 26 and the attached first base 22a relative to the second end portion 28 and the attached second base 22b.

The device 20 is configured such that in an assembled configuration, wherein the first end portions 26 and the second end portions 28 of the struts 24 are attached to the first base 22a and the second base 22b, the first base 22a is moveable relative to the second base 22b in up to six degrees of freedom. For example, the first base 22a can translate relative to the second base 22b in either the anterior-posterior direction AP, the medial-lateral direction ML, the superior-inferior direction SI, or any combination thereof. In addition, the first base 22a can rotate relative to the second base 22b about an axis defining the anterior-posterior direction AP, the medial-lateral direction ML, the superior-inferior direction SI, or any combination thereof.

The rotational locking of the strut 24 when attached to one of the bases 22 at both the first and second end portions 26 and 28 may be desired in an application where a certain orientation of the struts 24 relative to the bases 22 is desired. For example, the struts 24 can include visual indications regarding the properties of the strut 24, such as the current length of the strut. The rotational locking of the strut 24 as described above allows a user to have the visual indications facing in a direction that are easily readable by a user when the external bone fixation device 20 is attached to the bone 2.

The device 20, in one embodiment, includes a plurality of attachment mechanisms 200 that are configured to attach the first bone portion 4 to the first base 22a and the second bone portion 6 to the second base 22b such that as the first and second bases 22a and 22b move relative to one another, the first and second bone portions 4 and 6 also move relative to one another. In other words the attachment mechanisms 200 are configured to attach a base 22 to a portion of the bone 2 such that the base 22 and the portion of the bone 2 are translationally and rotationally coupled together.

As shown in the illustrated embodiment, the attachment mechanisms 200 can include a bracket 202 that can be attached to the base 22, for example by a fastener 206. The attachment mechanism 200 further includes the bone fixation element 204 that couples the bracket 202 to the bone 2. The bone fixation element 204 includes, for example, a wire 208 and a rod 210. In one embodiment, the wire 208 is a Kirschner wires (or "K-wire"). As shown, the wire 208 is configured to be attached to a first bracket 202a, extend completely through the bone 2, and be attached to a second bracket 202b on the other side of the bone 2. The rod 210 is configured to be attached to a bracket 202, and extend into, or partially through, the bone 2. As shown, the rod 210 is only attached to one bracket 202. The rod 210 can be threaded or have another retention structure on an end of the rod 210 that is inserted into the bone 2 that aids in securing the rod 210 to the bone 2.

Referring to FIGS. 2A and 2B, the base 22 includes a base body 34. As shown in the illustrated embodiment, the base body 34 can be substantially ring shaped. The base body 34 can be formed from a monolithic piece of material, as shown, or the base body 34 can be formed from separate pieces or segments of material that are joined together. The base 22 can include a base axis 36. In one embodiment, the base axis 36 is a central axis such that the base body 34 is substantially centered about the base axis 36. The base body 34 includes a first surface 38 (or upper surface), a second surface 40 (or lower surface) that is opposite the first surface 38, and a thickness T1 measured from the first surface 38 to the second surface 40. In one embodiment the thickness T1 is constant throughout the base body 34. In another embodiment the thickness T1 is not constant throughout the base body 34.

As shown in the illustrated embodiment, the first surface 38 is substantially planar such that the first surface 38 defines a plane P1. In another embodiment, the second surface 40 is substantially planar such that the second surface 40 defines the plane P1. In another embodiment both the first surface 38 and the second surface 40 are substantially planar such that either the first surface 38 or the second surface 40, or both define the plane P1.

Referring to FIGS. 1A to 2B, the device 20 includes more than one base 22. As shown, the device includes the first base 22a and the second device 22b. The first base 22a and the second base 22b are configured to be attached to the first bone portion 4 and second bone portion 6 of a bone 2, respectively. When the first base 22a and the second base 22b are first attached to the first and second bone portions 4 and 6, the first and second bone portions 4 and 6 are in a first orientation relative to one another. When the first and second bases 22a and 22b are attached to the first and second bone portions 4 and 6 in the first orientation, the first and second bone portions 4 and 6 are in an undesired position such that the planes P1 of the first and second bases 22a and 22b are non-parallel to one another, the base axes 36 of the first and second bases 22a and 22b are non-parallel, or both.

After the first and second bases 22a and 22b are secured to the first and second bone portions 4 and 6 in the first configuration, a treatment plan can be performed to move the first and second bases 22a and 22b into a second orientation. In the second orientation, the first and second bone portions 4 and 6 are in a desired position such that the planes P1 of the first and second bases 22a and 22b are substantially parallel to one another, the base axes 36 of the first and second bases 22a and 22b are substantially parallel, or both. As will be described in detail below, the treatment plan can include actuation of the actuators 32 of the struts 24. In one embodiment the treatment plan includes actuation of the actuators 32 of specified struts 24, a specified amount, over a specified amount of time.

Referring to FIGS. 2A and 2B, the base body 34 further includes a first side wall 44, such as an inner side wall, and a second side wall 46, such as an outer side wall, that is opposite the first side wall 44. As shown in the illustrated embodiment, the first side wall 44 defines an inner periphery of the base body 34, and the second side wall 46 defines an outer periphery of the base body 34. The base body 34 defines an inner diameter D1 measured from the first side wall 44 at a first location, through the base axis 36, and to the first side wall 44 at a second location. The base body 34 defines an outer diameter D2 measured from the second side wall 46 at a first location, through the base axis 36, and to the second side wall 46 at a second location.

The base 22 can further include an opening 48. The opening 48 is defined by the base body 34, for example the first side wall 44, and the opening 48 is configured to receive the bone 2. The base body 34 defines a width W1 measured from the second side wall 46 to the first side wall 44 in a direction perpendicular to the base axis 36. In one embodiment the width W1 is constant throughout the base body 34. In another embodiment the width W1 is not constant throughout the base body 34.

In one embodiment, the base body 34 includes at least one tab 56. The tab 56 includes a portion of the base body 34 that extends radially outward from the base axis 36 farther than a surrounding portion of the base body 34. As shown, the tab 56 defines a portion of the base body 34 with a greater width W1" than the width W1' of the base body 34 at a location adjacent the tab 56. The base body 34 can include any number of tabs 56 (including no tabs), spaced about the base body 34 in any desired configuration. For example, the base body 34 can include three tabs 56 spaced apart substantially equally about the outer periphery of the base body 34, such that each of the tabs 56 is spaced about 120 degrees from each of the other two tabs 56.

The base 22 also includes a plurality of holes 50. The plurality of holes 50 extend through the base body 34, for example the holes 50 extend though an entirety of the thickness T1 of the base body 34 from the first surface 38 to the second surface 40. The holes 50 are configured to receive the struts 24 and the attachment mechanisms 200. The holes 50 can be threaded, unthreaded, or a combination of threaded and unthreaded such that the holes 50 are configured to receive both locking and non-locking fasteners. In the illustrated embodiment, the holes 50 include a first series of holes 50a and a second series of holes 50b. The first series of holes 50a are arranged such that they are positioned on the base body 34 along a first circle 52a. The second series of holes 50b are arranged in the illustrated embodiment, such that they are positioned on a second circle 52b. As shown, the first circle 52a has a smaller diameter than the second circle 52b.

In one embodiment, the second series of holes 50b is positioned along the second circle 52b and the second circle 52b passes through at least one, for example three, tabs 56. The first and second series of holes 50a and 50b can be positioned within the base body 34 such that a first ray line R1 extending from the base axis 36 to the second side wall 46 passes through a hole 50 in the first series of holes 50a and a hole 50 in the second series of holes 50b. The first and second series of holes 50a and 50b can further be positioned within the base body 34 such that a second ray line R2 extending from the base axis 36 to the second side wall 46 passes through a hole 50 in the first series of holes 50a but does not pass through a hole 50 in the second series of holes 50b. The first and second series of holes 50a and 50b can still further be positioned within the base body 34 such that a third ray line R3 extending from the base axis 36 to the second side wall 46 passes through a hole 50 in the second series of holes 50b but does not pass through a hole 50 in the first series of holes 50a.

Each of the holes 50 defines a center 54. The holes 50 are arranged such that adjacent holes 50 define a distance between their centers 54. The distance is referred to hereafter as "chord length C1" for the first series of holes 50a and "chord length C2" for the second series of holes 50b. In one embodiment, the first series of holes 50a are arranged throughout the base body 34 such that the chord length C1' of first adjacent holes 50a' is different from the chord length C1" of second adjacent holes 50a".

Referring to FIGS. 2A to 2C, in one embodiment the base 22 can include a base body 1034. The base body 1034 is similar to the base body 34, described in reference to FIGS. 2A and 2B, in many aspects such that the description of the base body 34 herein can be applied to the base body 1034 except where indicated to the contrary. Corresponding structures between the different embodiments of the base 22 are identified by intervals of 1000, for example the base body 34 and the base body 1034.

The base body 1034 can include a plurality of holes 1050 that are positioned within the base body 1034 in a pattern that is different from the plurality of holes 50 within the base body 34. In one embodiment the structure and function of the plurality of holes 1050 are the same as the structure and function of the plurality of holes 50 except for the pattern (or position) of the plurality of holes 1050 within the base body 34.

In one embodiment the plurality of holes 1050 includes a first series of holes 1050*a*, a second series of holes 1050*b*, and a third series of holes 1050*c*. The first series of holes 1050*a* can be arranged such that each of the holes 1050 within the first series of holes 1050*a* are positioned on the base body 1034 along a first circle 1052*a*, the second series of holes 1050*b* can be arranged such that each of the holes 1050 within the second series of holes 1050*b* are positioned on a second circle 1052*b*, and the third series of holes 1050*c* can be arranged such that each of the holes 1050 within the third series of holes 1050*c* are positioned on a third circle 1052*c*. As shown, the first circle 1052*a* has a smaller diameter than the third circle 1052*c* and the third circle 1052*c* has a smaller diameter than the second circle 1052*b*.

In one embodiment, the third series of holes 1050*c* can include a single hole 1050. As shown in the illustrated embodiment, the third series of holes 1050*c* can be positioned within the base body 1034 such that a ray line R3' extending from a base axis 1036 through a second side wall 1046 such that the ray line R3' passes through the single hole 1050 in the third series of holes 1050*c* but does not pass through a hole 1050 in either the first series of holes 1050*a* or the second series of holes 1050*b*.

In another embodiment, the third series of holes 1050*c* can include a plurality of holes 1050. In another embodiment, the third series of holes 1050*c* can be positioned within the base body 1034 such that a ray line R3' extending from the base axis 1036 to the second side wall 1046 passes through one of the holes 1050 in the third series of holes 1050*c* and also passes through a hole 1050 in the first series of holes 1050*a*, a hole 1050 in the second series of holes 1050*b*, or both a hole 1050 in the first series of holes 1050*a* and a hole 1050 in the second series of holes 1050*b*.

Referring to FIG. 3A, in another embodiment the device 20 includes a base 122 that defines a base body 134. The base 122 is similar to the base 22 in many aspects such that the description of the base 22 herein can be applied to the base 122 except where indicated to the contrary. As shown, the base body 134 includes a primary base body 135*a* and a secondary base body 135*b*. The primary and secondary base bodies 135*a* and 135*b* are configured to be connected such that they form a complete ring. In one embodiment the primary base body 135*a* defines a partial ring, for example about a ⅝ (five-eighths) ring, and the secondary base body 135*b* defines another partial ring, for example a ⅜ (three/eighths) ring that complements the partial ring of the primary base body 135*a* such that when the primary and secondary base bodies 135*a* and 135*b* are joined, a complete ring is formed.

The use of a base 122 with segments, for example primary and secondary base bodies 135*a* and 135*b* provides additional flexibility or options when the device 20 is being assembled and attached to a patient. For example, the primary base body 135*a* can be placed in a desired position relative to a bone and the secondary base body 135*b* can be attached to the primary base body 135*a* in the desired position without having to traverse the base 122 all the way from a distal end of the bone (or appendage) to the desired position.

In another embodiment, the device 20 includes a base 122 that only includes the primary base body 135*a* such that the base 122 defines only a partial ring shape and a gap. The use of a partial ring shape, for example the primary base body 135*a*, can allow added flexibility for a patient that the device 20 is attached to. The primary base body 135*a* can be positioned such that the gap is posterior to (or behind) the patient's knee, allowing the patient's knee to flex without interference from the base body 134.

Referring to FIG. 3B, in another embodiment the device 20 includes a base 1122 that defines a base body 1134. The base 1122 is similar to the base 122 illustrated in FIG. 3A in many aspects such that the description of the base 122 herein can be applied to the base 1122 except where indicated to the contrary. As shown, the base body 1134 includes a primary base body 1135*a* and a secondary base body 1135*b*. The primary and secondary base bodies 1135*a* and 1135*b* are configured to be connected such that they form a complete ring. In one embodiment the primary base body 1135*a* defines a partial ring, for example about a ⅝ (five-eighths) ring, and the secondary base body 1135*b* defines another partial ring, for example a ⅜ (three/eighths) ring that complements the partial ring of the primary base body 1135*a* such that when the primary and secondary base bodies 1135*a* and 1135*b* are joined, a complete ring is formed.

As shown in the illustrated embodiment, the base 1122 can include a plurality of holes 1150 that are positioned within the base 1122 differently than those positioned within the base 122. For example, the base 1122 can include a plurality of holes 1150 that are positioned within the base 1122 in a pattern that includes first, second, and third series of holes, similar to the plurality of holes 1150 in the base body 1034 as illustrated in FIG. 2C.

Figure 4A:
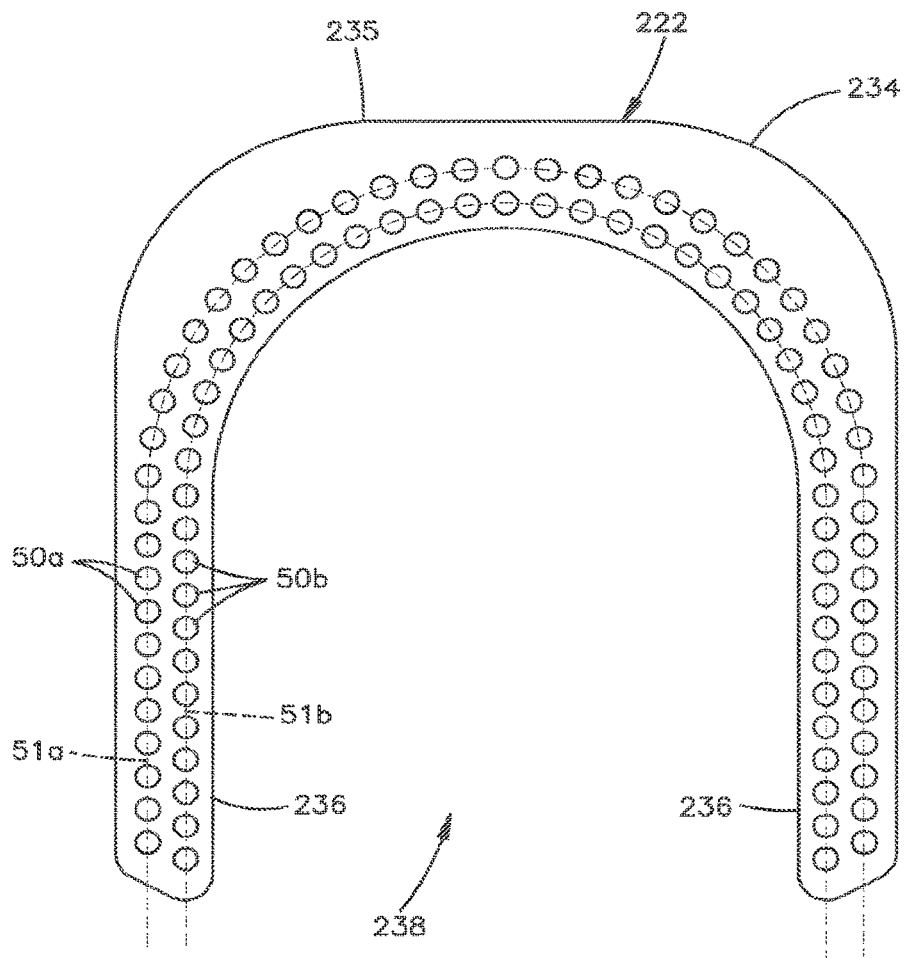
FIG. 4A is a top plan view of one of the plurality of bases illustrated in FIG. 1A, according to another embodiment.

Referring to FIG. 4A, in another embodiment the device 20 includes a base 222 that defines a base body 234. The base 222 is similar to the base 22 in many aspects such that the description of the base 22 herein can be applied to the base 222 except where indicated to the contrary. As shown, the base body 234 includes a primary base body 235 and one or more legs 236 extending out from the primary base body 235. As shown, the base body 234 includes two legs 236 extending out from the primary base body 235 such that the legs 236 are substantially parallel to each other. In another embodiment, the legs 236 extend out from the primary base body 235 such that the legs 236 are substantially non-parallel to each other. The base 222 further defines a gap 238 positioned between the legs 236. The base 222 is configured to be placed around an appendage, such as a foot such that the primary base body 235 is positioned posterior to (or behind) a heel of the foot, and the gap 238 is positioned to receive an anterior portion, such as the toes, of the foot. The use of the base 222 in the device 20 allows a patient to walk after the device 20 is attached to the patient, for example during treatment of a deformity or repair of an injury to the patient's foot.

Figure 4B:
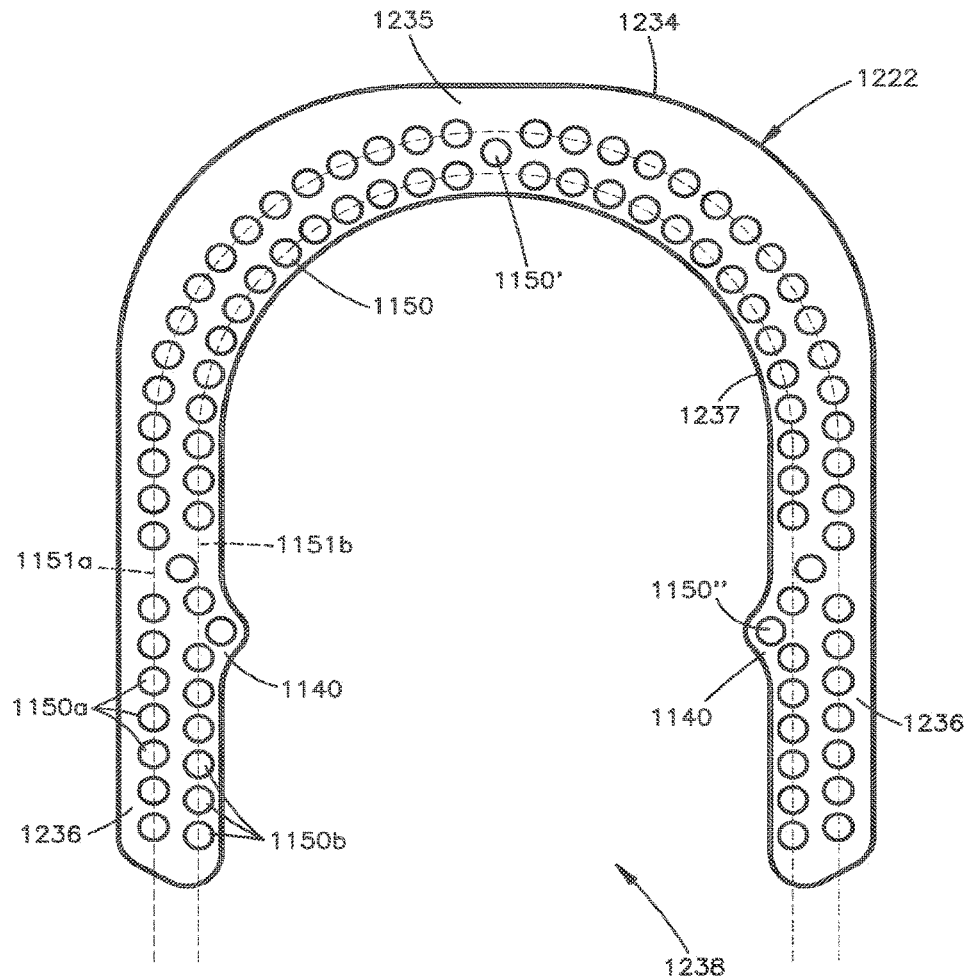
FIG. 4B is a top plan view of the one of the plurality of bases illustrated in FIG. 4A, according to another embodiment.

Referring to FIG. 4B, in another embodiment the device 20 can include a base 1222 that defines a base body 1234. The base 1222 is similar to the base 222 in many aspects such that the description of the base 222 herein can be applied to the base 1222 except where indicated to the contrary. As shown, the base body 1234 includes a primary base body 1235 and one or more legs 1236 extending out from the primary base body 1235. According to one embodiment, the base body 1234 includes two legs 1236 that extend out from the primary base body 1235 such that the legs 1236 are substantially parallel to each other. In another embodiment, the legs 1236 can extend out from the primary base body 1235 such that the legs 1236 are substantially non-parallel to each other. As shown, the one or more legs 1236 can be integral, or monolithic with the primary base body 1235. In another embodiment, the one or more legs 1236 can be releasably coupled to the primary base body 1235.

The base 1222 further defines a gap 1238 positioned between the legs 1236. The base 1222 is configured to be placed around an appendage, such as a foot such that the primary base body 1235 is positioned posterior to (or behind) a heel of the foot, and the gap 1238 is positioned to receive an anterior portion, such as the toes, of the foot. The use of the base 1222 in the device 20 allows a patient to walk after the device 20 is attached to the patient, for example during treatment of a deformity or repair of an injury to the patient's foot. As shown in the illustrated embodiment, the gap 1238 is at least partially defined, for example completely defined, by inner surfaces 1237 of the legs 1236.

The base body 1234 can include one or more projections 1140 that extend from either the legs 1236, the primary base body 1235, in a direction towards the gap 1238. As shown in the illustrated embodiment, the base body 1234 can include a projection 1140 on each of the pair of legs 1236. The projections 1140 are opposite one another such that the gap 1238 between the projections 1140 is smaller than the gap 1238 between the legs 1236 at a location without a projection 1140.

Referring to FIGS. 4A and 4B, the base 222 and the base 1222 each include a plurality of holes 50 and 1150, respectively. The positioning of the holes 1150 can be varied. For example, as shown in FIG. 4A, the plurality of holes 50 can be positioned within the base 222 such that the plurality of holes 50 includes a first series of holes 50a that are aligned along a first U-shaped line 51a, and a second series of holes 50b that are aligned in a second U-shaped line 51b. In one embodiment the second U-shaped line 51b is smaller than and does not overlap with the first U-shaped line 51a. In one embodiment, the base 222 can be devoid of any holes 50 that are not aligned with either the first U-shaped line 51a or the second U-shaped line 51b.

In another embodiment, as shown in FIG. 4B, the plurality of holes 1150 can be positioned within the base 1222 such that the plurality of holes 1150 includes a first series of holes 1150a that are aligned along a first U-shaped line 1151a, and a second series of holes 1150b that are aligned in a second U-shaped line 1151b. In one embodiment the second U-shaped line 1151b is smaller than and does not overlap with the first U-shaped line 1151a. As shown, the base 1222 can include one or more holes 1150 that are not aligned with either a first U-shaped line 1151a or a second U-shaped line 1151b. For example, the base 1222 can include a hole 1150' that 1) is not located on either the first U-shaped line 1151a or the second U-shaped line 1151b, and 2) is located between the first U-shaped line 1151a and the second U-shaped line 1151b. In another embodiment, the base 1222 can include one or more holes 1150" that 1) is not located on either the first U-shaped line 1151a or the second U-shaped line 1151b, and 2) is not located between the first U-shaped line 1151a and the second U-shaped line 1151b. In one embodiment the base 1222 can include one or more holes 1150" that are positioned within a projection 1140. The one or more holes 1150" and the one or more projections 1140 can be positioned within the base 1222 such that the one or more holes 1150" are configured to align with the one or more holes 50 or 1050 of the base 22 so as to receive the strut 24.

Referring to FIGS. 5A to 5C, in one embodiment, strut 24 includes a strut body 25, the strut body 25 includes, in one embodiment, a first member, for example a threaded rod 60, and a second member, for example a sleeve 62. The threaded rod 60 and the sleeve 62 are configured to be connected such that the threaded rod 60 and the sleeve 62 are translatable relative to one another. The strut 24 further includes a first joint 64 configured to be connected to the threaded rod 60, and a second joint 66 configured to be connected to the sleeve 62. One of the first and second joints 64 and 66, for example the first joint 64, can be a rotatable joint and the other of the first and second joints 64 and 66, for example 66, can be a non-rotatable joint, as described in greater detail below. The strut 24 also includes an actuator 32 configured to be coupled to the strut 24, for example supported by the strut body 25 such that actuation of the actuator 32 translates the threaded rod 60 relative to the sleeve 62.

The strut 24 includes a first end, such as a proximal end 68, and a second end, such as a distal end 70. The strut 24 further includes a strut axis 72 extending from the proximal end 68 to the distal end 70. The strut 24, in one embodiment, is elongate along the strut axis 72. As shown in the illustrated embodiment, the strut axis 72 is a central axis, and the strut axis 72 is parallel to the longitudinal direction L. The strut 24 defines a length L1 measured from a first point 73 to a second point 75 along the strut axis 72. In one embodiment the first point 73 is located at or near the proximal end 68, for example in the first joint 64, and the second point 75 is located at or near the distal end 70, for example in the second joint 66. Actuation of the actuator 32 translates the threaded rod 60 relative to the sleeve 62, changing the length L1.

Referring to FIGS. 5A to 6B, the threaded rod 60 includes a first end, for example a rod proximal end 74, a second end, for example a rod distal end 76, and a rod body 78 that extends from the rod proximal end 74 to the rod distal end 76 and is elongate in the longitudinal direction L, or along the strut axis 72. The rod body 78 includes an outer surface 80 that is at least partially threaded. The threaded rod 60 defines an outer dimension D3, for example an outer diameter. One end of the threaded rod 60, for example the rod proximal end 74, is configured to receive the first joint 64. The strut 24 includes a follower 77. In one embodiment, the follower 77 is supported by the rod distal end 76. The follower 77 is configured to prevent the threaded rod 60 from rotating relative to the sleeve 62 as the threaded rod 60 translates relative to the sleeve 62. The follower 77 can be in the form of a set screw 79 that is configured to be secured to a set screw hole 81 of the threaded rod 60. The set screw 79 includes a head portion 83 and a shaft 85 that extends out from the head portion 83. In one embodiment, the set screw hole 81 is positioned within the rod distal end 76.

The rod distal end 76 can include a flat section that is configured to receive the set screw 79 such that the head portion 83 of the set screw 79 abuts the flat section and the shaft 85 of the set screw 79 extends through the set screw hole 81 and protrudes out of the set screw hole 81 and at least partially into a track 89 of the sleeve 62 as described in detail below.

The sleeve 62 includes a first end, for example a sleeve proximal end 82, a second end, for example a sleeve distal end 84, and a sleeve body 86 that extends from the sleeve proximal end 82 to the sleeve distal end 84 and is elongate in the longitudinal direction L. In one embodiment, the sleeve 62 includes a recess, such as a bore 88 that extends into and at least partially through the sleeve body 86 from the sleeve proximal end, in the longitudinal direction towards the sleeve distal end 84. The sleeve body 86, as shown, defines a tube-like structure.

The sleeve body 86 includes a sleeve inner surface 90 that defines the bore 88, and a sleeve outer surface 92 that is opposite the sleeve inner surface 90. The sleeve 62 defines an inner dimension D4, such as an inner diameter measured within the bore 88, and an outer dimension D5, such as an outer diameter. The sleeve outer surface 92 includes an engagement mechanism, for example the sleeve proximal end 82 is at least partially threaded. The sleeve body 86 can be substantially C-shaped such that the sleeve body 86 defines a slot 94. The slot 94 extends in the transverse direction T from the sleeve outer surface 92 to the sleeve inner surface 90, and the slot 94 extends in the longitudinal direction L, or along the strut axis 72, between the sleeve proximal end 82 and the sleeve distal end 84.

The sleeve 62 can further include a track 89 that is configured to receive the follower 77 of the threaded rod 60 such that interference of the follower 77 and the track 89 prevents rotation of the threaded rod 60 relative to the sleeve 62 as the threaded rod 60 translates relative to the sleeve 62. The track 89 extends into the sleeve body 86 from the sleeve inner surface 90 in a direction toward the sleeve outer surface 92. In one embodiment the track 89 does not extend all the way through the sleeve body 86. In another embodiment the track 89 is spaced apart from the slot 94, for example such that if the slot extends through the "top" of the sleeve 62, the track extends towards the "bottom" of the sleeve 62. In another embodiment the track 89 is at least partially aligned with the slot 94.

As shown in the illustrated embodiment, the actuator 32 includes a distraction nut 96, and a drive nut 98. The actuator 32 can further carry at least a portion of a locking mechanism 104 of the strut 24. In one embodiment, the distraction nut 96 and the drive nut 98 are configured to be rotationally and translationally coupled to each other, such that for example, as the distraction nut 96 translates along the longitudinal direction L, the drive nut 98 also translates along the longitudinal direction L, and as the distraction nut 96 rotates about the longitudinal direction L, the drive nut 98 also rotates about the longitudinal direction L.

The distraction nut 96 includes a gripping member 100, such as an actuator housing 102. In one embodiment, the gripping member 100 carries a portion of the locking mechanism 104, which can include a locking mechanism body 105, for example a lever 106 as shown, such that as the gripping member 100 moves (for example translates along the longitudinal direction L or rotates about an axis aligned with the longitudinal direction L) the locking mechanism 104 moves with the gripping member 100. The gripping member 100 is configured to be connected to the sleeve 62 such that the gripping member 100 is rotatable, for example about the longitudinal direction L (or the strut axis 72), relative to the sleeve 62.

At least a portion of the locking mechanism 104 is configured to be connected to, or carried by, the gripping member 100 such that when the locking mechanism 104 is in a first, or locked, configuration the gripping member 100 is rotationally locked with respect to the sleeve 62, preventing the gripping member 100 from rotating relative to the sleeve 62. The locking mechanism is further configured to be connected to or carried by, the gripping member 100 such that when the locking mechanism 104 is in a second, or unlocked configuration the gripping member 100 is rotatable with respect to the sleeve 62.

Referring to FIGS. 5A to 7D, the gripping member 100 includes a proximal end 108, a distal end 110, and a gripping member body 112 extending from the proximal end 108 to the distal end 110. The gripping member body 112 includes an outer surface 114 and an inner surface 116 that is opposite the outer surface 114. The gripping member 100 further includes a bore 118 that is at least partially defined by the inner surface 116. The bore 118 extends into and at least partially through the gripping member body 112 from the proximal end 108 to the distal end 110. As shown in the illustrated embodiment, the bore 118 can include a first portion 160 and a second portion 162.

The gripping member 100 defines a first inner dimension D6 measured within the first portion 160 of the bore 118, and a second inner dimension D7 measured within the second portion 162 of the bore 118. As shown the first and second inner dimensions D6 and D7 can be different, such that the first inner dimension D6 is larger than the second inner dimension D7. The inner surface 116 defining the first portion 160 is partially threaded in one embodiment. In another embodiment, the inner surface defining the first portion 160 is entirely threaded or entirely unthreaded.

The outer surface 114 of the gripping member body 112 is partially cylindrical or a tube-like shape such that the gripping member 100 defines an outer dimension D8, for example an outer diameter, measured from a first point on the outer surface 114, through the strut axis 72, to a second point on the outer surface 114 that is opposite the first point. The gripping member 100 can further include at least one groove 164 that extends into the gripping member body 112 from the outer surface 114 in a direction toward the inner surface 116 such that the groove 164 defines a depth E1. The gripping member 100 can includes multiple grooves 164, as shown, to improve a user's ability to grip and apply a torque to the gripping member 100.

The gripping member 100 can further include a projection 166 that is configured to receive a torque applied to the gripping member 100 to make rotation of the gripping member 100 easier, for example by providing a mechanical advantage. As shown the projection 166 is in the form of a raised portion 168. The raised portion 168 includes at least one projection side wall 170, for example two projection side walls, that extends out from the outer surface 114 of the gripping member body 112 in a direction away from the inner surface 116 of the gripping member body 112. The projection 166 defines a height H1 measured from where the projection side wall 170 extends out from the outer surface 114 and in the direction that the projection side wall extends away from the inner surface 116. In one embodiment, the projection 166 further includes a projection top surface 172 extending between the projection side walls 170.

As shown in the illustrated embodiment, the outer dimension D8 of the gripping member 100 is measured at a location that does not include the projection 166. The gripping member 100 further defines an outer dimension D9 measured from the a first point on the outer surface 114, through the strut axis 72, to a second point located on either the projection side wall 170 or the projection top surface 172. In one embodiment, the projection 166 is configured such that the height H1 of the projection side wall 170 is between about 3 mm and about 9 mm, the outer dimension D8 is between about 15 mm to about 30 mm, and the outer dimension D9 is between about 20 mm and about 35 mm. In another embodiment, the projection 166 is configured such that the height H1 of the projection side wall 170 is about 6 mm, the outer dimension D8 is about 22 mm, and the outer dimension D9 is about 27 mm. In another embodiment, the projection 166 is configured such that the height H1 of the projection side wall 170 is at least 10 percent of the outer dimension D8. In another embodiment, the height H1 of the projection side wall 170 is at least 20 percent of the outer dimension D8. In another embodiment, the height H1 is between about 20 percent and about 30 percent of the outer dimension D8.

In one embodiment, the depth E1 is between about 0.5 mm and about 1 mm. In another embodiment the height H1 is at least 5 times greater than the depth E1. In another embodiment the height H1 is at least 10 times greater than the depth E1. In another embodiment the height H1 is between about 5 and about 10 times greater than E1. For example, in one embodiment, the gripping member 100 can define an outer dimension D8 of about 22 mm, an outer dimension D9 of about 27 mm, a projection height H1 of about 6 mm, and a groove depth E1 of about 0.7 mm.

As shown in the illustrated embodiment, the gripping member 100, specifically the projection 166 carries at least a portion of the locking mechanism 104. The projection 166 includes a projection body 174 and a recess 176 extending into the projection body 174 and terminating at a base surface 177. The recess 176 is configured to at least partially receive the locking mechanism 104. The locking mechanism 104 is configured such that in a first, locked configuration the locking mechanism 104 prevents rotation of the gripping member 100 relative to the sleeve 62. The locking mechanism 104 is further configured such that in a second, unlocked configuration the locking mechanism 104 does not interfere with rotation of the gripping member 100 relative to the sleeve 62.

In one embodiment, the locking mechanism 104 includes a locking mechanism body 105. The locking mechanism body can include the lever 106. The lever 106 is configured to be pivotally attached to the gripping member 100. The lever 106 includes a pivot axis 178 that the lever 106 pivots about from the first, locked configuration to the second, unlocked configuration. As shown, locking mechanism 104 can include a pin 182. The lever 106 and the gripping member 100, specifically the projection 166, each include corresponding through holes 180a and 180b, respectively configured to be aligned and receive the pin 182. When the locking mechanism 104 is pivotally attached to the gripping member 100 as described above, the locking mechanism 104 is pivotable from the first, locked configuration to the second, unlocked configuration about an axis, specifically the pivot axis 178, that is non-parallel to the strut axis 72. In another embodiment, the locking mechanism 104 is pivotable from the first, locked configuration to the second, unlocked configuration about an axis, specifically the pivot axis 178, that is substantially perpendicular to the strut axis 72.

As shown in the illustrated embodiment the locking mechanism 104 includes the locking mechanism body 105 and a biasing member, such as a spring 184. The locking mechanism body 105 can be in the form of the lever 106 that includes a base portion 186, a stop portion 188, and the pivot axis 178. The base portion 186 can be positioned on one side of the pivot axis 178 and the stop portion 188 can be positioned on the other side of the pivot axis 178 as shown. The recess 176 of the projection 166 is further configured such that when the lever 106 is at least partially received within the recess 176 and the lever 106 is pivotally attached to the gripping member 100, the spring 184 is configured to be received within the recess 176.

In one embodiment, the spring 184 is configured to be positioned within the recess 176 such that the spring 184 is between the base surface 177 of the projection 166 and the base portion 186 of the lever 106. The spring 184 can be configured such that when the lever 106 is pivotally attached to the gripping member 100 the spring 184 exerts a biasing force on the base portion 186 of the lever 106 in a direction away from the strut axis 72, for example in a direction substantially perpendicular to the strut axis 72, such that the locking mechanism 104 is biased towards the first, locked configuration. In one embodiment, the spring 184 is configured to bias the lever 106 into the first, locked configuration even when the strut 24 is under a load, for example during actuation of the actuator 32 to change the length L1 of the strut 24, when the strut 24 is attached to a pair of external bone fixation members, such as the bases 22. Application of a greater force to the base portion 186, in the opposite direction of the biasing force pivots the lever 106 about the pivot axis 178 into the second, unlocked configuration.

Referring to FIGS. 5A to 6B, the strut 24 can further include a bearing 190. The bearing 190 is configured to connect the actuator 32 to the sleeve 62 such that the actuator 32 is translationally fixed relative to the sleeve 62, and rotatable about the strut axis 72 relative to the sleeve 62. The bearing includes a proximal end 192, a distal end 194, and a bearing body 196 extending from the proximal end 192 to the distal end 194. The bearing 190 further includes a bearing bore 198 extending into and at least partially through the bearing body 196 from the proximal end 192 to the distal end 194. The bearing, as shown, includes a first portion 260 and a second portion 262.

The bearing 190 defines a first inner dimension D10 measured within the bearing bore 198 at the first portion 260, and a second inner dimension D11 measured within the bearing bore 198 at the second portion 262. As shown the first and second inner dimensions D10 and D11 can be different, such that the first inner dimension D10 is smaller than the second inner dimension D11. The bearing body 196 further includes an inner surface 264 and an outer surface 266 that is opposite the inner surface 264. The inner surface 264 at least partially defines the bearing bore 198. The inner surface 264, for example the second portion 262, is partially threaded in one embodiment. In another embodiment, the inner surface 264 defining the bearing bore 198 within the second portion 262 is entirely threaded or entirely unthreaded.

The bearing 190 further defines a first outer dimension D12 defined by the outer surface 266 measured within the first portion 260, and a second outer dimension D13 defined by the outer surface 266 measured within the second portion 262. As shown the first and second outer dimensions D12 and D13 can be different, for example the first outer dimension D12 can be smaller than the second outer dimension D13.

The locking mechanism 104 of the strut 24 can further include a locking feature 268, for example a recess 270 configured to engage the locking mechanism body 105, for example by receiving the stop portion 188 of the lever 106. In one embodiment the recess 270 is defined by the bearing 190. The recess 270 and the stop portion 188, in one embodiment, have corresponding shapes such that when the locking mechanism 104 is in the first, locked configuration the locking mechanism body 105, for example the stop portion 188, is at least partially received within the locking feature 268, for example, the recess 270 preventing any rotation of the locking mechanism 104 relative to the bearing 190. When the locking mechanism 104 is in the second, unlocked configuration the locking mechanism body 105, for example the stop portion 188, is completely removed from the locking feature 268, for example the recess 270, such that the locking mechanism 104 can rotate relative to the portion of the strut 24 that carries the locking feature 268, for example the bearing 190, about the strut axis 72.

Referring to FIGS. 5A to 6B, 8A and 8B, the actuator 32 can further include a drive nut 98 that is rotationally and translatably locked relative to the distraction nut 96. The drive nut 98 is further configured to engage the threaded rod 60 such that the drive nut 98 is rotatable and translatable relative to the threaded rod 60. As shown in the illustrated embodiment, the drive nut 98 includes an attachment portion 272, a collet portion 274, and an intermediate portion 276 between the attachment portion 272 and the collet portion 274. The attachment portion 272 is configured to be secured to the distraction nut 96. For example, the attachment portion 272 can include an outer surface 278 that is at least partially threaded. The threaded outer surface 278 of the attachment portion 272 is configured to engage the threaded inner surface 116 of the distraction nut 96. When the corresponding threaded inner surface 116 and threaded outer surface 278 are engaged, the distraction nut 96 and the drive nut 98 are secured relative to one another both translationally and rotationally.

The collet portion 274 of the drive nut 98 is configured to releasably engage with the threaded rod 60 both rotationally and translatably. As shown, the collet portion 274 includes a plurality of flexible fingers 280, each flexible finger 280 being separated from an adjacent flexible finger 280 by a gap 282. Each of the flexible fingers 280 includes an inner surface 284 and an outer surface 286 opposite the inner surface 284. The inner surface 284 of the flexible fingers 280 is at least partially threaded such that the threaded inner surface 284 of the collet portion 274 corresponds to the threaded outer surface 80 of the threaded rod 60.

The collet portion 274 includes an open configuration in which the threaded inner surface 284 is capable of translating relative to the threaded rod 60 without rotating the drive nut 98 relative to the threaded rod 60. In the open configuration, a user is able to make quick, relatively large adjustments to the length L1 of the strut 24 by simply translating the threaded rod 60 relative to the sleeve 62 without the need to rotate or actuate the actuator 32. The collet portion 274 further includes a closed configuration in which the threaded inner surface 284 engages the threaded rod 60 such that the drive nut 98 cannot translate relative to the threaded rod 60 without rotating the drive nut 98 relative to the threaded rod 60.

The drive nut 98 can further include a clamp 288, for instance a ring clamp 290 as shown in the illustrated embodiment. The clamp 288 includes a clamp body 292 and a through hole 294 passing through the clamp body 292. The clamp body 292 includes an inner surface 296 that at least partially defines the through hole 294. The clamp body 292 further defines an inner dimension D14, for example an inner diameter, that is configured such that the clamp 288 is configured to be slidably attached to the intermediate portion 276 and the collet portion 274. As shown, the intermediate portion 276 or the collet portion 274 is configured to pass at least partially through the through hole 294.

Figure 8A:
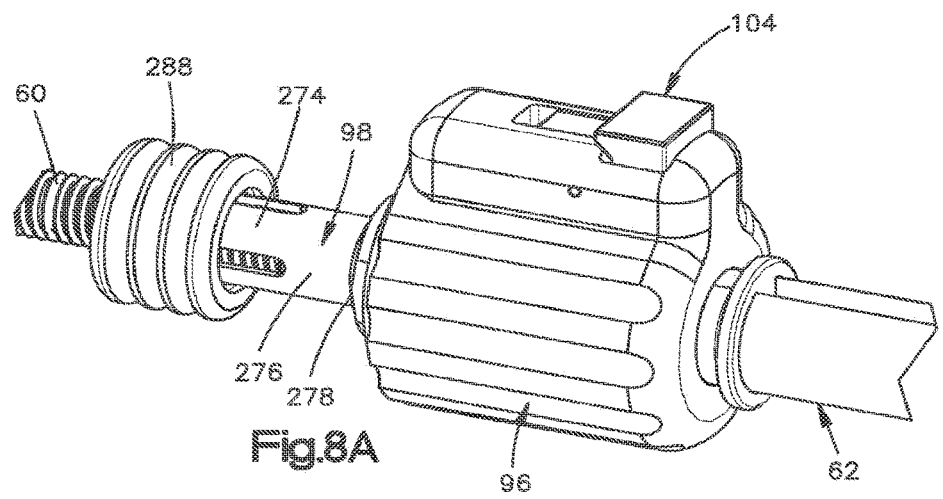
FIG. 8A is a perspective view of the strut illustrated in FIG. 5A, the strut including a distraction nut, a drive nut, and a clamp in a first position.
Figure 8B:
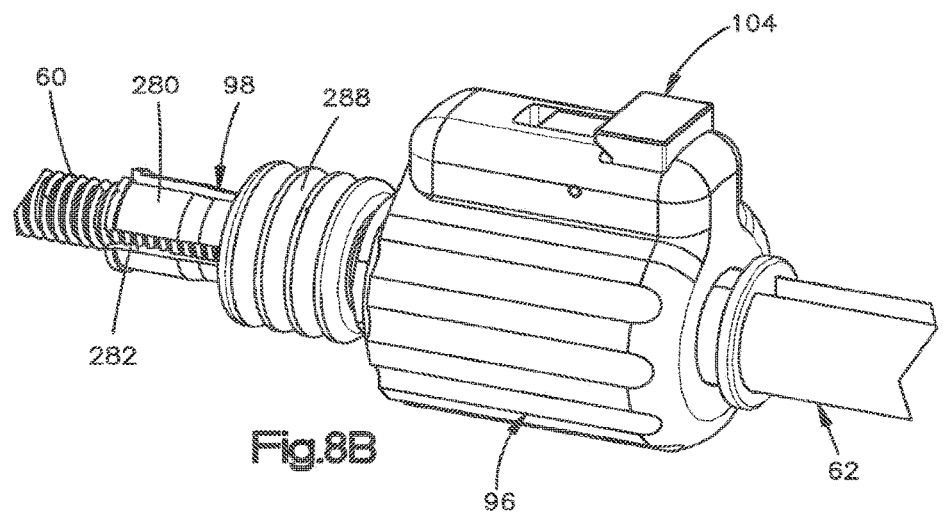
FIG. 8B is a perspective view of the actuator illustrated in FIG. 8A, with the clamp in a second position.

Referring to FIGS. 8A and 8B, the clamp 288 is moveable relative to the drive nut 98 between a first position (as shown in FIG. 8A) and a second position (as shown in FIG. 8B), such that in the first position the collet portion 274 passes at least partially though the through hole 294. In the first position the clamp 288 biases or compresses the flexible fingers 280 of the collet portion 274 into the closed configuration. In the second position the intermediate portion 276 passes at least partially through the through hole 294 such that the clamp 288 does not bias the flexible fingers 280 of the collet portion 274 into the closed configuration. In one embodiment, the flexible fingers 280 of the collet portion 274 are naturally biased into the open configuration, such that if the clamp 288 is in the second position, and thus not biasing the flexible fingers 280 into the closed configuration, the collet portion 274 will be in the open configuration allowing the drive nut 98 to translate freely along the threaded rod 60 without rotating the drive nut 98 relative to the threaded rod 60.

In one embodiment, the actuator 32 can be made of a radiolucent material such as a polymer, for example polyether ether ketone (PEEK). Use of a radiolucent material such as PEEK in one or more portions of the strut 24 provides a clear radiography image of the bone 2 and other parts of the device 20 made from radiopaque materials, which may assist the development a treatment plan for the external bone fixation device 20 to correct a bone defect or repair a bone injury. In another embodiment, any combination of the threaded rod 60, sleeve 62, actuator 32, first joint 64, and second joint 66, either in whole or in part is formed from a radiolucent material such as PEEK. In another embodiment, any one of or any combination of the threaded rod 60, sleeve 62, actuator 32, first joint 64, and second joint 66, either whole or in part, is formed from a polyetherimide (PEI), for example Ultem. In another embodiment, any one of or any combination of the threaded rod 60, sleeve 62, actuator 32, first joint 64, and second joint 66, either whole or in part, is formed from a polyoxymethylene (POM), for example Delrin. In another embodiment, any one of or any combination of the threaded rod 60, sleeve 62, actuator 32, first joint 64, and second joint 66, either whole or in part, is formed from a polyphenylsulfone (PPSF or PPSU), for example Radel. In one embodiment, components of the locking mechanism 104 can be formed, either in whole or in part, from titanium, titanium alloy, aluminum, or aluminum alloy.

Referring to FIGS. 5A to 6B, the strut 24 further includes the first joint 64 and the second joint 66. The first joint 64 is described below as a non-rotatable joint attached to the threaded rod 60 and the second joint 66 is described as a rotatable joint (that includes a shoulder 452) attached to the sleeve 62. It should be understood that in one embodiment, the first (non-rotatable) joint 64 can be attached to the sleeve 62 and the second (rotatable) joint 66 can be attached to the threaded rod 60. In another embodiment, the strut 24 can include two first (non-rotatable) joints 64, one attached to the threaded rod 60 and one attached to the sleeve 62. In another embodiment, the strut 24 can include two second (rotatable) joints 66, one attached to the threaded rod 60 and one attached to the sleeve 62.

The first joint 64 is configured to be located at one of the first end and the second end, for example the proximal end 68, of the strut 24 and the second joint 66 is configured to be located at the other of the first end and the second end, for example the distal end 70, of the strut 24. The first and second joints 64 and 66 are configured to attach the strut 24 to the first and second bases 22a and 22b. The first joint 64 includes a first hinge body 300, a second hinge body 302, and a cross coupling member 304 that is configured to pivotally connect the first and second hinge bodies 300 and 302. In one embodiment, the first joint 64 includes a fastener receiving hole 350 that extends into and at least partially through the second hinge body 302. The fastener receiving hole 350 is configured to receive a fastener 14 (as shown in FIG. 1A) that is inserted through the fastener receiving hole 50 of the base 22 and into the fastener receiving hole 350 of the first joint 64 to attach the strut 24 to the base 22 at the attachment location 23. The term "non-rotatable joint" used herein refers to a joint, for example the first joint 64, that is configured such that when the non-rotatable joint is attached to the base 22, for example by a fastener 14 as described above, the second hinge body 302 does not rotate relative to the base 22.

The first joint 64, in one embodiment, is configured as a universal joint such that the first and second hinge bodies 300 and 302 are rotationally coupled about a first axis, and rotatable relative to one another about a second axis and a third axis. For example, the first and second hinge bodies 300 and 302 are configured to be rotationally coupled about the strut axis 72 and pivotal relative to one another about a first pivot axis 306 and a second pivot axis 308. In the illustrated embodiment, the first and second pivot axes 306 and 308 define a plane that is perpendicular to the strut axis 72. The first and second hinge bodies 300 and 302 are rotatable relative to each other about any axis that lies in the plane.

The first hinge body 300 includes a base portion 310 and a pair of legs 312, extending out from the base portion 310. The legs 312 are spaced apart from one another to define a first gap 314 that is configured to at least partially receive the cross coupling member 304. The second hinge body 302 includes a base portion 316 and a pair of legs 318, extending out from the base portion 316. The base portion 316 includes a base surface 354 configured to face the base 22 when the first joint 64 is attached to the base 22. The second hinge body 302 includes a fastener receiving hole 350 extending into the base portion 316. The second hinge body 302 can include threads 356 such that the fastener receiving hole 350 is threaded. In one embodiment, fastener receiving hole 350 is threaded along its entire length, such that the threads 356 abut the base surface 354 with no gap between the threads 356 in the fastener receiving hole 350 and the base surface 354. The legs 318 are spaced apart from one another to define a second gap 320 that is configured to at least partially receive the cross coupling member 304.

The pair of legs 312 and 318 of both the first and second hinge bodies 300 and 302 can further include an attachment feature configured to secure the cross coupling member 304 within the first and second gaps 314 and 320. As shown, the pair of legs 312 of the first hinge body 300 includes a first pin hole 322 configured to receive a first pin 324, and the pair of legs 318 of the second hinge body 302 includes a second pin hole 326 configured to receive a second pin 328.

The cross coupling member 304 includes a body 330 that is configured to be at least partially received between the first and second gaps 314 and 320. In one embodiment, the body 330 is substantially spherical. In another embodiment the cross coupling member 304 is made from a first material and the first and second hinge bodies 300 and 302 are made from second material that is different from the first material. The first material can be more radiopaque than the second material. For example, the cross coupling member 304 can be made from titanium and the first and second hinge bodies 300 and 302 can be made from aluminum. The shape of the body 330, for example substantially spherical, and the difference in materials between the cross coupling member 304 and the first and second hinge bodies 300 and 302 can improve the use of radiography, such as x-rays, to plan a treatment plan using the external bone fixation device 20 to correct a bone defect or repair a bone injury. For example, if body 330 is substantially spherical in shape, the body 330 will appear as a circle (or substantially as a circle) in an x-ray taken from any angle about the external bone fixation device. Forming the cross coupling member 304 from a more radiopaque material than the first and second hinge bodies 300 and 302 will result in the cross coupling member appearing brighter on the x-ray than the surrounding structure.

The cross coupling member 304 further includes a first pin hole 332, the first pin 324, a second pin hole 334, and the second pin 328. The first pin hole 332 of the cross coupling member 304 is configured to receive the first pin 324 when the first pin hole 332 is aligned with the first pin hole 322 of the first hinge body 300. The second pin hole 334 of the cross coupling member 304 is configured to receive the second pin 328 when the second pin hole 334 is aligned with the second pin hole 326 of the second hinge body 302. As shown the first and second pin holes 332 and 334 of the cross coupling member 304 pass through one another, for example at about a 90 degree angle. One of the first and second pin holes 332 and 334 can be larger than the other of the first and second pin holes 332 and 334, such that the larger of the first and second pin holes 332 and 334 is configured to receive a larger one of the first and second pins 324 and 328. For example, the second pin hole 334 and the second pin 328 can be larger than the first pin hole 332 and the first pin 324. The second pin hole 334 can include a cross hole 336 that is configured to be aligned with the first pin hole 332 and receive the first pin 324.

The first hinge body 300 is configured to be coupled to the threaded rod 60, such that the threaded rod 60 and the first hinge body 300 are translationally and pivotally coupled to each other. In one embodiment, the base portion 310 of the first hinge body 300 includes a recess 338 that is configured to at least partially receive the rod proximal end 74 of the threaded rod 60, and a pin 342. The rod body 78 and the base portion 310 can include matching pin holes 341a and 341b configured to be aligned and then receive the pin 342. Once the pin 342 is inserted through the aligned matching pin holes 341a and 341b, the threaded rod 60 and the first joint 64 are translationally and rotationally coupled with respect to one another. Although the first hinge body 300 and the threaded rod 60 are shown as separate parts that are releasable and coupleable to each other, in another embodiment, the first hinge body 300 and the threaded rod 60 can be formed from a single piece of material, or monolithically formed.

The second joint 66 includes a first hinge body 400, a second hinge body 402, and a cross coupling member 404 that is configured to pivotally connect the first and second hinge bodies 400 and 402. In one embodiment, the second joint 66 includes a fastener receiving hole 450 that extends into and at least partially through the second hinge body 402. The fastener receiving hole 450 is configured to receive a fastener 14 (as shown in FIG. 1A) that is inserted through the fastener receiving hole 50 of the base 22 and into the fastener receiving hole 450 of the second joint 66 to attach the strut 24 to the base 22 at the attachment location 23. The term "rotatable joint" used herein refers to a joint, for example the second joint 66, that is configured such that when the rotatable joint is attached to the base 22, for example by a fastener 14 as described above, the second hinge body 402 is rotatable relative to the base 22.

The second joint 66, as shown in the illustrated embodiment, is configured as a universal joint such that the first and second hinge bodies 400 and 402 are rotationally coupled about a first axis, and rotatable relative to one another about a second axis and a third axis. For example, the first and second hinge bodies 400 and 402 are configured to be rotationally coupled about the strut axis 72 and pivotable relative to one another about a first pivot axis 406 and a second pivot axis 408. In the illustrated embodiment, the first and second pivot axes 406 and 408 define a plane that is perpendicular to the strut axis 72. The first and second hinge bodies 400 and 402 are rotatable relative to each other about any axis that lies in the plane defined by the first and second pivot axes 406 and 408.

The first hinge body 400 includes a base portion 410 and a pair of legs 412, extending out from the base portion 410. The legs 412 are spaced apart from one another to define a first gap 414 that is configured to at least partially receive the cross coupling member 404. The second hinge body 402 includes a base portion 416 and a pair of legs 418, extending out from the base portion 416. The base portion 416 includes a base surface 454 configured to face the base 22 when the second joint 66 is attached to the base 22. The second hinge body 402 includes a fastener receiving hole 450 extending into the base portion 416 from the base surface 454 in a direction toward the pair of legs 418 such that the fastener receiving hole 450 defines a length. The second hinge body 402 can further include threads 456 such that the fastener receiving hole 450 is threaded. In one embodiment, fastener receiving hole 450 is threaded along a portion of its length, such that the threads 456 do not abut the base surface 454. Instead a shoulder 452 (for example in the form of a gap or unthreaded portion) is positioned between the threads 456 in the fastener receiving hole 450 and the base surface 454. The shoulder 452 is configured such that when the second joint 66 is attached to the base 22, the second joint 66 is rotatable relative to the base 22. The legs 418 are spaced apart from one another to define a second gap 420 that is configured to at least partially receive the cross coupling member 404.

The pair of legs 412 and 418 of both the first and second hinge bodies 400 and 402 can further include an attachment feature configured to secure the cross coupling member 404 within the first and second gaps 414 and 420. As shown, the pair of legs 412 of the first hinge body 400 includes a first pin hole 422 configured to receive a first pin 424, and the pair of legs 418 of the second hinge body 402 includes a second pin hole 426 configured to receive a second pin 428.

Similarly to the cross coupling member 304 of the first joint 64 described above, the cross coupling member 404 of the second joint 66, in one embodiment, includes a body 430 that is configured to be at least partially received between the first and second gaps 414 and 420. The body 430, as shown, is substantially spherical and can be made from a first material, for example titanium, and the first and second hinge bodies 400 and 402 can be made from second material, for example aluminum, that is different from the first material. The shape of the body 430, for example substantially spherical, and the choice of materials for the cross coupling member and the first and second hinge bodies 400 and 402 can be selected to improve the use of radiography, such as x-rays, to plan a treatment plan using the external bone fixation device 20 to correct a bone defect or repair a bone injury.

The cross coupling member 404 further includes a first pin hole 432, the first pin 424, a second pin hole 434, and the second pin 428. The first pin hole 432 of the cross coupling member 404 is configured to receive the first pin 424 when the first pin hole 432 is aligned with the first pin hole 422 of the first hinge body 400. The second pin hole 434 of the cross coupling member 404 is configured to receive the second pin 428 when the second pin hole 434 is aligned with the second pin hole 426 of the second hinge body 402. As shown the first and second pin holes 432 and 434 of the cross coupling member 404 pass through one another, for example at about a 90 degree angle. One of the first and second pin holes 432 and 434 can be larger than the other of the first and second pin holes 432 and 434, such that the larger of the pin holes 432 and 434 is configured to receive a larger one of the first and second pins 424 and 428. For example, the second pin hole 434 and the second pin 428 can be larger than the first pin hole 432 and the first pin 424. The second pin hole 434 can include a cross hole 436 that is configured to be aligned with the first pin hole 432 and receive the first pin 424.

The first hinge body 400 is configured to be coupled to the sleeve 62, such that the sleeve 62 and the first hinge body 400 are translationally and pivotally coupled to each other. As shown in the illustrated embodiment, the base portion 410 of the first hinge body 400 is integral with the sleeve 62 such that the first hinge body 400 and the sleeve 62 are monolithic. In another embodiment the base portion 410 includes a recess configured to at least partially receive the sleeve 62. In another embodiment, the base portion 410 includes a post configured to be at least partially received within the bore 88 of the sleeve. In another embodiment, the sleeve 62 and the base portion 410 can include matching pin holes configured to be aligned and then receive a pin as described in detail above in reference to the first joint 64.

Figure 6B:
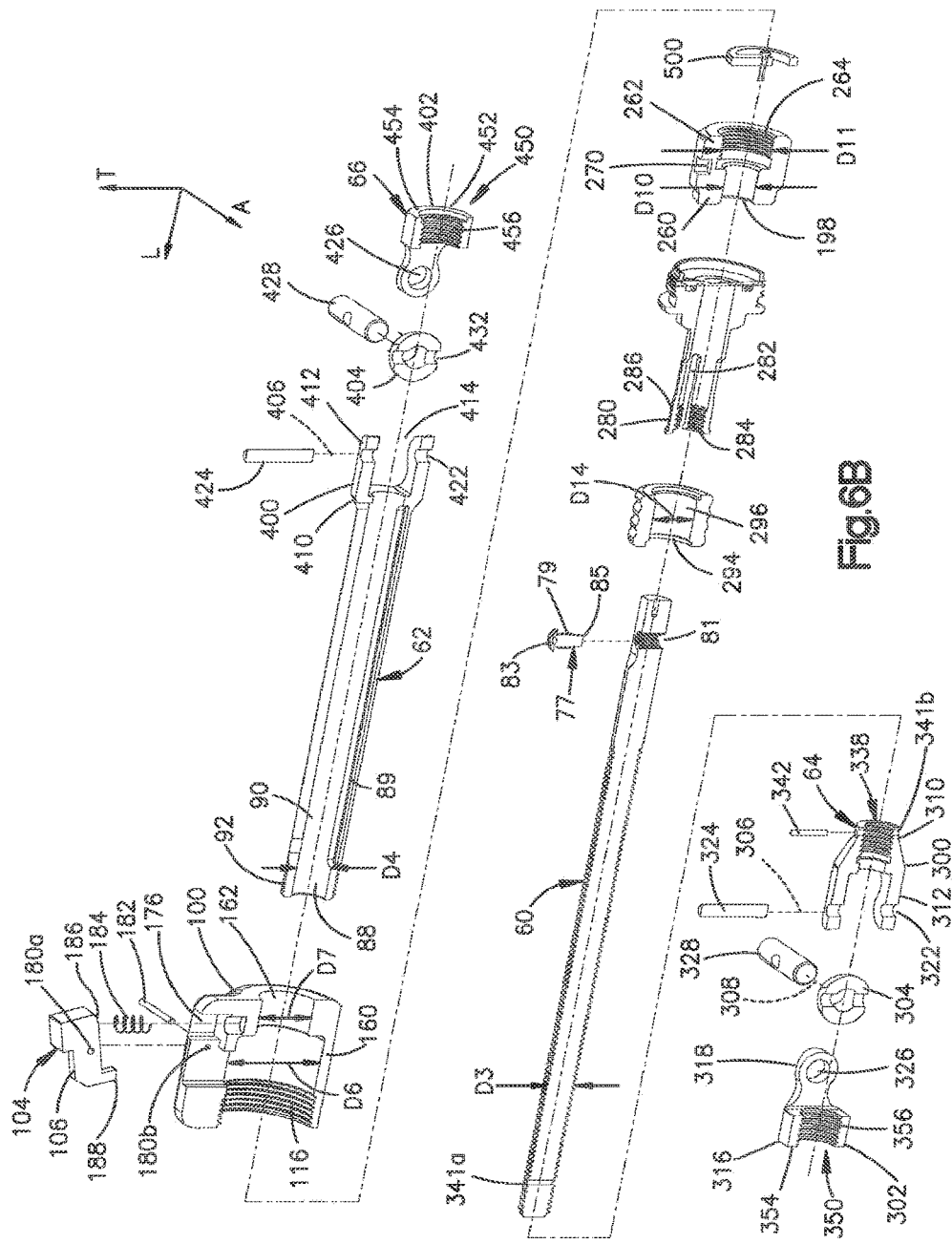
FIG. 6B is an exploded, cross-sectional view of the strut illustrated in FIG. 7A along line 5C-5C.

Referring to FIGS. 6A and 6B, in one embodiment the strut 24 can be assembled as described below. The threaded rod 60 is inserted into the bore 88 of the sleeve 62 such that the follower 77 is at least partially received within the track 89. Once the threaded rod 60 is positioned within the sleeve 62 as described, the threaded rod 60 and the sleeve 62 are translatable relative to each other along the strut axis 72, but they are not rotatable relative to each other about the strut axis 72. The bearing 190 is attached to the sleeve outer surface 92 such that the bearing 190 and the sleeve 62 are rotationally and translationally coupled relative to one another. For example the threaded inner surface 264 of the bearing can be threadedly engaged with the threaded sleeve outer surface 92. The threaded rod 60 passes through the bearing bore 198 such that the threaded rod 60 is translatable relative to the bearing 190.

The actuator 32 is attachable to the strut 24 such that the bearing 190 is at least partially received within the bore 118 of the distraction nut 96 such that the bearing 190 is rotatable relative to the distraction nut 96 about the strut axis 72. The drive nut 98 is attachable to the distraction nut 96 such that the drive nut 98 and the distraction nut are translationally and rotationally coupled to each other. When the drive nut 98 and the distraction nut 96 are attached as described above, the bearing 190 is positioned within the first portion 160 of the bore 118 of the distraction nut 96, such that the bearing is translationally secured relative to the actuator 32 along the strut axis 72 and rotatable about the strut axis 72 relative to the actuator 32.

The drive nut 98 is configured to be placed in the closed configuration by moving the clamp 288 into the first position such that the collet portion 274 is compressed and threaded inner surface 284 of the flexible fingers 280 threadedly engages the threaded outer surface 80 of the threaded rod 60. In the closed configuration rotation of the drive nut 98 relative to the threaded rod 60 about the strut axis 72 translates the drive nut 98 relative to the threaded rod 60 along the strut axis 72. The clamp 288 can be moved into the second position placing the drive nut 98 in the open configuration such that the threaded inner surface 284 of the flexible fingers 280 does not threadedly engage the threaded outer surface 80 of the threaded rod 60. In the open configuration the drive nut 98 is translatable relative to the threaded rod 60 along the strut axis 72 without rotating the drive nut 98 relative to the threaded rod 60 about the strut axis 72.

The first joint 64 is attachable to the rod proximal end 74 such that the first hinge body 300 is both translationally (along the strut axis 72) and rotatably (about the strut axis 72) coupled to the threaded rod 60. The second joint 66 is attachable to the sleeve distal end 84 such that the first hinge body 400 is both translationally (along the strut axis 72) and rotatably (about the strut axis 72) coupled to the sleeve 62.

Figure 9B:
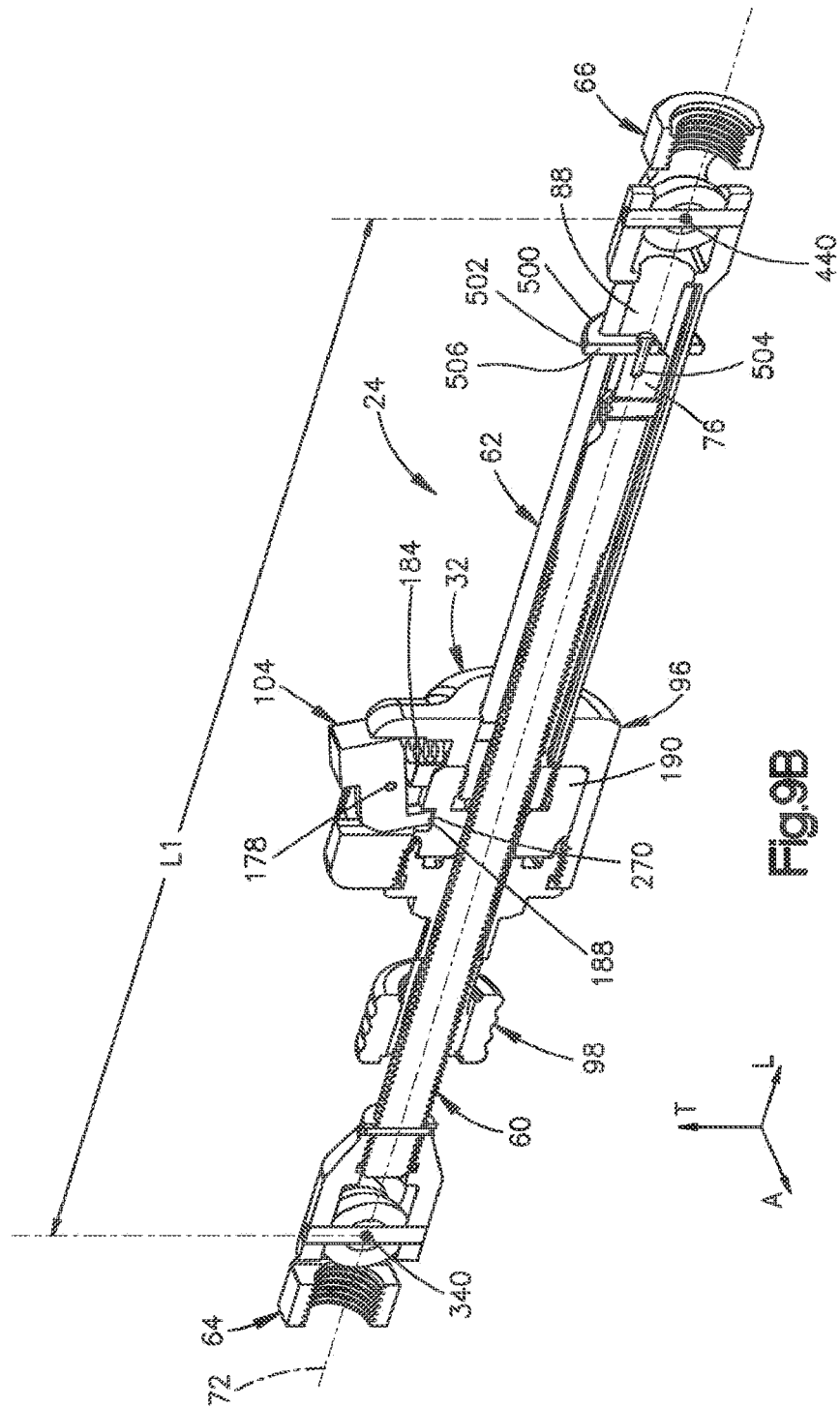
FIG. 9B is a cross-sectional view of the strut illustrated in FIG. 9A along line 9B-9B.

Referring to FIGS. 9A to 10B, the strut 24 defines a length L1 measured from a first point on the strut 24 to a second point on the strut 24. As shown in the illustrated embodiment, the length L1 is measured from the cross coupling member 304 of the first joint 64, specifically a center 340 of the cross coupling member 304, along the strut axis 72, to the cross coupling member 404 of the second joint 66, specifically a center 440 of the cross coupling member 404. The length L1 of the strut 24 is adjustable between a minimum length (as shown in FIGS. 9A and 9B) and a maximum length (as shown in FIGS. 10A and 10B). The length L1 is adjustable by actuation of the actuator 32. The actuation of the actuator 32 can include translation along the strut axis 72, rotation about the strut axis 72, or both relative to the threaded rod 60.

To change the length L1 of the strut 24, the locking mechanism 104 is moved from the first, locked configuration to the second unlocked configuration. For example, an applied force is exerted by a user on the locking mechanism body 105, for example on the base portion 186 of the lever 106. If the applied force is greater than the biasing force applied by the spring 184 on the base portion 186, and the applied force is applied in substantially the opposite direction of the biasing force of the spring 184, then the application of the applied force causes the lever 106 to pivot about the pivot axis 178. As the lever 106 pivots about the pivot axis 178, the stop portion 188 of the lever 106 moves out of engagement with the recess 270 of the bearing 190. When the stop portion 188 is removed from the recess 270, the locking mechanism 104 is in the second, unlocked configuration and the actuator 32 is now rotatable relative to the threaded rod 60 about the strut axis 72.

Once the actuator 32 has been rotated in a first direction, for example counter-clockwise, such that the stop portion 188 of the lever 106 is no longer aligned with the recess 270, the applied force can be removed from the base portion 186. A torque applied to the gripping member 100, for example to the projection 166, in one embodiment specifically to one of the projection side walls 170, rotates the actuator relative to the threaded rod 60. Because the actuator 32 is translationally coupled to the outer surface, rotation of the actuator 32 translates the threaded rod 60 relative to the actuator 32 and the sleeve 62 changing the length L1 as measured between the cross coupling members 304 and 404 of the first and second joints 64 and 66.

Upon the completion of a full rotation (360 degrees) about the strut axis 72, the stop portion 188 of the lever 106 moves into alignment with the recess 270 of the bearing 190. Once the stop portion 188 and recess 270 are aligned, the biasing force of the spring 184 pivots the lever 106 about the pivot axis 178 until the stop portion 188 is at least partially received within the recess 270. When the stop portion 188 is at least partially received within the recess 270 the locking mechanism 104 is once again in the first, locked configuration and further rotation of the actuator 32 relative to the threaded rod 60 about the strut axis 72 is prevented by interference between the stop portion 188 and the locking feature 268. In one embodiment, the locking mechanism body 105, for example the stop portion 188, and the locking feature 268, for example the recess 270, include opposed surfaces, for example first and second surfaces. The opposed surfaces are configured such that no amount of torque applied by hand to the locking mechanism 104 about the strut axis 72 will cause the opposed surfaces to cam over one another.

In one embodiment, the opposed surfaces are planar and substantially parallel to one another. In another embodiment the opposed (first and second) surfaces are substantially perpendicular to the strut axis. As the locking mechanism 104 rotates back into the first, locked configuration an audible indication, for example a "click" is produced to alert a user to the completion of a revolution of the actuator 32 and confirm that the locking mechanism 104 is once again in the first, locked configuration. In another embodiment, as the locking mechanism 104 rotates back into the first, locked configuration a visual indication, a tactile indication, or both are produced, either instead of or in addition to the audible indication, to alert a user to the completion of a revolution of the actuator 32 and confirm that the locking mechanism 104 is once again in the first, locked configuration.

As shown, the locking mechanism 104 is configured such that the biasing force of the spring 184 is applied to the base portion 186 of the lever 106 in a direction that is angularly offset from the direction of elongation of the strut 24, or the strut axis 72 in the illustrated embodiment. The angular offset of the biasing force relative to the strut axis 72, shown in the illustrated embodiment, prevents the application of a torque to the actuator 32 from rotating the actuator 32 relative to the threaded rod 60 when the locking mechanism 104 is in the first, locked configuration. Thus, in the illustrated embodiment, only when the locking mechanism 104 is in the second, unlocked configuration does the application of a torque to the actuator 32 rotate the actuator 32 relative to the threaded rod 60.

The strut 24 is configured such that a single rotation (360 degrees) of the actuator 32 relative to the threaded rod 60, translates the threaded rod 60 a predetermined amount relative to the sleeve 62. Thus a single rotation of the actuator 32 relative to the threaded rod 60, changes the length L1 a predetermined amount. The predetermined amount can be adjusted, for example by selecting a pitch for the corresponding threads of the actuator 32 and the threaded rod 60. In one embodiment, a single rotation of the actuator 32 relative to the threaded rod 60, changes the length L1 of the strut 24 by 1 millimeter (mm).

Referring to FIGS. 6A-6B to 9A-10B, in one embodiment the strut 24 includes a length indicator 500. The length indicator 500 is configured to provide a visual indication of the length L1 of the strut 24. As shown in the illustrated embodiment the length indicator 500 includes a clip 502 that is configured to be coupled to the threaded rod 60 such that clip 502 is translationally secured relative to the threaded rod 60 and rotatable about the strut axis 72 relative to the threaded rod 60. The length indicator 500 can include a pin 504, such that the clip 502 is configured to be attached by the pin 504 to the rod distal end 76. The clip 502 can include a post 506 that extends at least partially through the slot 94 of the sleeve 62 when the clip is attached to the threaded rod 60 and the threaded rod 60 is positioned at least partially within the bore 88 of the sleeve 62. The length indicator 500 can further include markings 508 (as shown in FIG. 9A) on the sleeve outer surface 92. The markings 508 can be configured such that as the threaded rod 60 translates within the bore 88 of the sleeve 62, the clip 502 which is attached to the threaded rod 60, is positioned adjacent a marking that indicates the current length L1 of the strut 24.

Referring to FIGS. 11A to 11C, the device 20 can include a strut 1024 in replacement of, or in combination with, one or more of the struts 24. The structure, function, and method of use of the strut 1024 is similar to structure, function, and method of use of the strut 24 in many aspects such that the description of the strut 24 herein can be applied to the strut 1024 except where indicated to the contrary. In accordance with one embodiment, the strut 1024 includes a strut body 1025, the strut body 1025 can include, a first member, for example a threaded rod 1060, and a second member, for example a sleeve 1062. The threaded rod 1060 and the sleeve 1062 are configured to be connected such that the threaded rod 1060 and the sleeve 1062 are translatable relative to one another. The strut 1024 can further include the first joint 64, described in detail above, configured to be connected to the threaded rod 1060, and the second joint 66, described in detail above, configured to be connected to the sleeve 1062. The strut 1024 also includes an actuator 1032 configured to be coupled to the strut 1024, for example supported by the strut body 1025 such that actuation of the actuator 1032 translates the threaded rod 1060 relative to the sleeve 1062. The strut can further include a locking mechanism 1104, at least a portion of which is carried by the actuator 1032.

According to one embodiment, the locking mechanism 1104 can include a locking mechanism body 1105, a biasing member 1183, and a locking feature 1268. The locking mechanism body 1105 can be in the form of, for example, a push member 1106 as shown in the illustrated embodiment. The locking mechanism body 1105 can be configured to be carried by a gripping member 1100 of the actuator 1032 such that as the gripping member 1100 moves (for example translates along the longitudinal direction L or rotates about an axis aligned with the longitudinal direction L) the locking mechanism 1104 moves with the gripping member 1100.

The strut 1024 includes a first end, such as a proximal end 1068, and a second end, such as a distal end 1070. The strut 1024 further includes a strut axis 1072 extending from the proximal end 1068 to the distal end 1070. The strut 1024, in one embodiment, is elongate along the strut axis 1072. As shown in the illustrated embodiment, the strut axis 1072 can be a central axis, and the strut axis 1072 can be parallel to the longitudinal direction L. The strut 1024 defines a length L1' measured from a first point 1073 to a second point 1075 along the strut axis 1072. In one embodiment the first point 1073 can be located at or near the proximal end 1068, for example in the first joint 64, and the second point 1075 can be located at or near the distal end 1070, for example in the second joint 66. Actuation of the actuator 1032 translates the threaded rod 1060 relative to the sleeve 1062, changing the length L1'.

Referring to FIGS. 11A to 13, the threaded rod 1060 includes a first end, for example a rod proximal end 1074, a second end, for example a rod distal end 1076, and a rod body 1078 that extends from the rod proximal end 1074 to the rod distal end 1076 and is elongate in the longitudinal direction L, or along the strut axis 1072. One end of the threaded rod 1060, for example the rod proximal end 1074, can be configured to receive the first joint 64. The rod body 1078 includes an outer surface 1080 that is at least partially threaded. The threaded rod 1060 defines an outer dimension D3'. As shown the outer dimension D3' can be a cross-sectional dimension that is measured in a direction perpendicular to the strut axis 1072.

In one embodiment at least a portion of the rod body 1078 defines a non-circular shape. As shown, the threaded portion of rod body 1078 can include at least one flat 1077 such that the rod body 1078 defines a D-shaped cross-sectional shape. In another embodiment the rod body 1078 can include more than one flat 1077 such that the rod body 1078 defines a polygonal shape. The flat 1077 can be unthreaded, as shown. The cross-sectional shape of the rod body 1078 is configured to be inserted into a bore 1088 of the sleeve 1062, the bore 1088 defining a cross-sectional shape that corresponds to the cross-sectional shape of the rod body 1078 such that when the threaded rod 1060 is inserted into the sleeve 1062 the corresponding cross-sectional shapes of the rod body 1078 and the bore 1088 prevent the threaded rod 1060 from rotating relative to the sleeve 1062 as the threaded rod 1060 translates relative to the sleeve 1062. In one embodiment, the at least one flat 1077 extends along a plane that is partially defined by a chord of a circular shape, a portion of the circular shape defining a sleeve outer surface 1092. The plane can further be defined by a direction that is parallel to the strut axis 1072.

The rod body 1078, according to one embodiment, includes a pin hole 1341a. The pin hole 1341a is similar to the pin hole 341a as described above in reference to strut 24. The pin hole 1341a is configured to receive a pin, for example the pin 342 as described in reference to strut 24, such that the threaded rod 1060 and the first joint 64 are translationally and rotationally coupled with respect to one another.

Referring to FIGS. 11A to 14C, the sleeve 1062 includes a first end, for example a sleeve proximal end 1082, a second end, for example a sleeve distal end 1084, and a sleeve body 1086 that extends from the sleeve proximal end 1082 to the sleeve distal end 1084 and, in one embodiment, is elongate in the longitudinal direction L. The sleeve body 1086, as shown, can define a tube-like structure. The sleeve 1062 includes a recess, such as a bore 1088 that extends into and at least partially through the sleeve body 1086 from the sleeve proximal end 1082, in the longitudinal direction L towards the sleeve distal end 1084.

The sleeve 1062 can define a first opening 1089 of the bore 1088, for example, positioned at the sleeve proximal end 1082. The first opening 1089 defines a cross-sectional shape such that the bore 1088 of the sleeve 1062 is configured to receive and translate relative to the threaded rod 1060. As shown in the illustrated embodiment, the first opening 1089 defines a cross-sectional shape that matches the cross-sectional shape of the rod body 1078. The first opening 1089 can be partially defined by at least one flat 1091 such that the first opening 1089 defines a D-shaped cross-sectional shape. In another embodiment the first opening can be partially defined by more than one flat 1091 such that the first opening 1089 defines a polygonal shape.

The sleeve body 1086 can include a sleeve inner surface 1090 that defines the bore 1088, and a sleeve outer surface 1092 that is opposite the sleeve inner surface 1090. The sleeve 1062 defines an inner dimension D4', such as an inner diameter measured within the bore 1088, and an outer dimension D5', such as an outer diameter. The inner dimension D4' and the outer dimension D5' can each be measured in a direction perpendicular to the strut axis 1072, or alternatively to an axis of elongate of the sleeve 1062.

The sleeve 1062 can include a shoulder portion 1094. In one embodiment, the shoulder portion 1094 is located on the sleeve outer surface 1092 at the sleeve proximal end 1082. As shown, the shoulder portion 1094 can define a maximum value for the outer dimension D5' of the sleeve 1062. The shoulder portion 1094 can be configured to be captured between the actuator 1032 such that the actuator 1032 and the sleeve 1062 are translationally locked to one another such that the actuator 1032 and the sleeve 1062 are prevented from moving relative to one another alone the strut axis 1072.

In one embodiment, the sleeve 1062 can define the locking feature 1268. The locking feature 1268 can be in the form of a recess 1097 that extends from the sleeve outer surface 1092 toward the sleeve inner surface 1090 and terminates prior to reaching the inner surface 1090. In one embodiment the recess 1097 extends from the sleeve outer surface 1092 through the sleeve inner surface 1090 such that the recess 1097 is open to the bore 1088. The locking feature 1268 can be configured to selectively engage with the locking mechanism body 1105 of locking mechanism 1104 to: 1) prevent the actuator 1032 and sleeve 1062 from rotating relative to one another about the strut axis 1072 when the strut is in a locked configuration, and 2) allow the actuator 1032 and sleeve 1062 to rotate relative to one another about the strut axis 1072 when the strut is in an unlocked configuration. The recess 1097 can be positioned at a location between the sleeve proximal end 1082 and the sleeve distal end 1084, for example at a location that is closer to the sleeve proximal end 1082 than the sleeve distal end 1084, as shown in the illustrated embodiment.

The sleeve 1062 can include an engagement mechanism 1099 configured to engage with a length measurement device 1500 as described in greater detail below. The engagement mechanism 1099 can be in the form of recess 1101 that extends from the sleeve outer surface 1092 toward the sleeve inner surface 1090. In one embodiment, the recess 1101 is a circumferential recess that is positioned around an entirety of the sleeve outer surface 1092 at a location between the sleeve proximal end 1082 and the sleeve distal end 1084, for example at a location that is closer to the sleeve proximal end 1082 than the sleeve distal end 1084.

In use, the threaded rod 1060 and the sleeve 1062 are configured to be oriented with respect to one another such that the cross-sectional shape of the threaded rod 1060 is aligned with the cross-sectional shape of the first opening 1089 of the sleeve 1062, for example such that the flat 1077 of the threaded rod 1060 is aligned with the flat 1091 of the sleeve 1062. When the threaded rod 1060 and the sleeve 1062 are aligned, the threaded rod 1060 can be inserted and translated within the bore 1088 of the sleeve 1062 along the strut axis 1072, but interference between the flats 1077 and 1091 prevents rotation of the threaded rod 1060 relative to the sleeve 1062 about the strut axis 1072.

The strut 1024 can further include, in accordance with one embodiment, the first hinge body 400 as described in detail above in reference to FIGS. 5A to 6B. The first hinge body 400 can include a base portion 410 and a pair of legs 412, that extend out from the base portion 410. The legs 412 are spaced apart from one another to define a first gap 414 that is configured to at least partially receive the cross coupling member 404. The pair of legs 412 can further include the first pin hole 422 which defines the first pivot axis 406 of the second joint 66.

The first hinge body 400 is configured to be coupled to the sleeve 1062, such that the sleeve 1062 and the first hinge body 400 are translationally and pivotally coupled to each other. As shown in the illustrated embodiment, the first hinge body 400 is integral with the sleeve 1062 such that the first hinge body 400 and the sleeve 1062 are monolithic. In another embodiment the first hinge body 400 includes a recess configured to at least partially receive the sleeve 1062. In another embodiment, the first hinge body 400 includes a post configured to be at least partially received within the bore 1088 of the sleeve 1062. In another embodiment, the sleeve 1062 and the first hinge body 400 can include matching pin holes configured to be aligned and then receive a pin as described in detail above in reference to the first joint 64.

Referring to FIGS. 11A to 12B and 15A to 16D, in accordance with one embodiment, the actuator 1032 includes a distraction nut 1096, the drive nut 98, and a locking mechanism 1104. As shown, the distraction nut 1096 and the drive nut 98 are configured to be rotationally and translationally coupled to each other, such that for example, as the distraction nut 1096 translates along the longitudinal direction L, the drive nut 98 also translates along the longitudinal direction L, and as the distraction nut 1096 rotates about the longitudinal direction L, the drive nut 98 also rotates about the longitudinal direction L.

The distraction nut 1096 includes a gripping member 1100, such as an actuator housing 1102. In one embodiment, the gripping member 1100 carries the locking mechanism 1104 such that as the gripping member 1100 moves (for example translates along the longitudinal direction L or rotates about an axis aligned with the longitudinal direction L) the locking mechanism 1104 moves with the gripping member 1100. The gripping member 1100 is configured to be connected to the sleeve 1062 such that the gripping member 1100 is rotatable, for example about the longitudinal direction L (or the strut axis 1072), relative to the sleeve 1062.

The locking mechanism 1104 is configured to be connected to, or carried by, the gripping member 1100 such that when the locking mechanism 1104 is in a first, or locked, configuration the gripping member 1100 is rotationally locked with respect to the sleeve 1062, preventing the gripping member 1100 from rotating relative to the sleeve 1062. The locking mechanism 1104 can further be configured to be connected to, or carried by, the gripping member 1100 such that when the locking mechanism is in a second, or unlocked configuration the gripping member 1100 is rotatable with respect to the sleeve 1062.

The gripping member 1100 include a proximal end 1108, a distal end 1110, and a gripping member body 1112 extending from the proximal end 1108 to the distal end 1110. The gripping member body 1112 includes an outer surface 1114 and an inner surface 1116 that is opposite the outer surface 1114. The gripping member 1100 further includes a bore 1118 that is at least partially defined by the inner surface 1116. The bore 1118 extends through the gripping member body 1112 from the proximal end 1108 to the distal end 1110. As shown in the illustrated embodiment, the bore 1118 can include a first portion 1160 and a second portion 1162.

The gripping member 1100 defines a first inner dimension $D6'$ measured within the first portion 1160 of the bore 1118 in a direction perpendicular to the longitudinal direction L, and a second inner dimension $D7'$ measured within the second portion 1162 of the bore 1118 in the direction perpendicular to the longitudinal direction L. As shown, the first and second inner dimensions $D6'$ and $D7'$ can be different, such that the first inner dimension $D6'$ is larger than the second inner dimension $D7'$. The inner surface 1116 defining the first portion 1160 is partially threaded in one embodiment. In another embodiment, the inner surface defining the first portion 1160 is entirely threaded or entirely unthreaded.

The outer surface 1114 of the gripping member body 112 can be substantially cylindrical such that the gripping member 1100 defines an outer dimension D8', for example an outer diameter, measured from a first point on the outer surface 1114, through the strut axis 1072, or alternatively in the transverse direction T, to a second point on the outer surface 1114 that is opposite the first point. The gripping member 1100 can further include at least one groove 1164 that extends into the gripping member body 1112 from the outer surface 1114 in a direction toward the inner surface 1116 such that the groove 1164 defines a depth E1'. Although the illustrated embodiment of the gripping member 1100 is shown as being substantially circular in shape, in another embodiment the gripping member 1100 can include a projection 166 illustrated in FIGS. 7A to 7D.

Referring to FIGS. 12A to 12B and 15A to 16D, as shown in the illustrated embodiment, the actuator 1032, for example the gripping member 1100, can be configured to carry the locking mechanism 1104. The gripping member 1100 defines a first recess 1176 that extends into the gripping member body 1112 from a location on the outer surface 1114 and terminates at a base surface 1177. The first recess 1176 is configured to receive the locking mechanism 1104. The locking mechanism 1104 is configured such that in a first, locked configuration the locking mechanism 1104 prevents rotation of the gripping member 1100 relative to the sleeve 1062. The locking mechanism 1104 can further be configured such that in a second, unlocked configuration the locking mechanism 1104 does not prevent rotation of the gripping member 1100 relative to the sleeve 1062. The gripping member 1100 can further define a second recess 1179 at least partially defined by the base surface 1177.

The locking mechanism 1104, can be in the form of a spring biased button assembly, as shown in the illustrated embodiment. The locking mechanism 1104 can include the locking mechanism body 1105, which as shown can be in the form of the push member 1106, a biasing member 1183, which as shown can be in the form of a spring 1184, and the locking feature 1268, which as shown can include the recess 1097 of the sleeve 1062. The push member 1106 is configured to be inserted into the first recess 1176 of the gripping member 1100, and the spring 1184 is configured to be inserted into the second recess 1179, such that the spring 1184 is configured to provide a biasing force to the push member 1106. The push member 1106 is configured to translate within the first recess along a direction that, in one embodiment, is substantially perpendicular to the longitudinal direction L. The push member 1106 is translatable to move the locking mechanism 1104 from the first, locked configuration to the second, unlocked configuration.

According to one embodiment, the push member 1106 can include a push member body 1400 and a bore 1402 that extends through the push member body 1400, the bore 1402 is configured to receive the sleeve 1062 such that at least a portion of the sleeve outer surface 1092 is positioned within the bore 1402. The push member body 1400 includes an inner surface 1404 that at least partially defines the bore 1402. The push member 1106 can further include an outer surface 1406 that includes an upper surface 1408 and a lower surface 1410. The upper surface 1408 can be configured to receive a force from a user, the force being sufficient to overcome the biasing force provided by the biasing member 1183 and translate the push member 1106 within the first recess 1176 to the second, unlocked configuration. The lower surface 1410 can be configured to receive the biasing force from the biasing member 1183, the biasing force being sufficient, in the absence of other forces applied by the user, to translate the push member 1106 within the first recess into the first, locked configuration.

The push member 1106, in one embodiment, includes an engagement mechanism 1412 that is configured to selectively engage with locking feature 1268, which as shown can be defined by the sleeve 1062. Engagement of the push member 1106 with the recess 1097 defines a locked configuration of the locking mechanism such that at least one of the actuator 1032 and sleeve 1062 is prevented from rotating relative to the other about the strut axis 1072. Disengagement of the push member 1106 from the recess 1097 defines an unlocked configuration of the locking mechanism such that at least one of the actuator 1032 and sleeve 1062 is prevented from rotating relative to the other about the strut axis 1072. The engagement mechanism 1412 can be in the form of a projection 1416 that extends from the inner surface 1404, for example in a direction toward the upper surface 1408. As shown in the illustrated embodiment the projection 1416 corresponds in shape, for example is at least partially insertable into the recess 1097.

The biasing member 1183 is configured to be inserted into the gripping member 1100, for example into the second recess 1179, such that the biasing member 1183 provides a biasing force on the push member 1106, for example in a direction away from the base surface 1177. The biasing member 1183 can further be configured such that when push member 1106 and the biasing member 1183 are both inserted within the gripping member 1100, the spring 1184 exerts a biasing force on the lower surface 1410 in a direction offset, for example substantially perpendicular to the strut axis 1072, to bias the locking mechanism 1104 towards the first, locked configuration. The biasing force being applied in a direction offset to the strut axis 1072 can allow the biasing member 1183 to bias the push member 1106 into the first, locked configuration even when the strut 1024 is under a load, for example during actuation of the actuator 1032 to change the length L1' of the strut 1024, when the strut 1024 is attached to a pair of external bone fixation members, such as the bases 22.

Referring to FIGS. 8A to 8B, 11A to 12B, and 17A to 17D, the strut 1024 (as well as any other embodiments of the strut disclosed herein) can include a locking collar 1450 that is configured to be attached to the drive nut 98 of the actuator 1032. The locking collar 1450 includes a locking collar body 1452 and a bore 1454 that extends through the locking collar body 1452. The locking collar 1450 can include a joint 1456 that allows the locking collar 1450 to transition, for example hinge, between an open configuration and a closed configuration. In the open configuration the locking collar 1450 is configured to be attached to the drive nut 98, and in the closed configuration the locking collar 1450 is configured to remain secured to the drive nut 98.

As shown in the illustrated embodiment, the bore 1454 is configured to be attached to the intermediate portion 276 of the drive nut 98 when the collet portion 274 of the drive nut 98 is in the closed configuration. When the locking collar 1450 is attached to the drive nut 98 such that at least a portion of the intermediate portion is received within the bore 1454, the locking collar 1450 prevents the clamp 288 from moving from the first position to the second position, and thus preventing the collet portion from transitioning from the closed configuration to the open configuration.

Referring to FIGS. 11A to 12B and 18A to 18F, the strut 1024 can include a length measurement device 1500 that is configured to display to the user a length of the strut 1024, for example the length L1'. Although described in use with the strut 1024 below, the length measurement device 1500 as described below can also be configured to display the length of any embodiments of the strut (24, 2024, 3024), for example the length L1.

In one embodiment, the length measurement device 1500 includes a sensor 1502 and a marker 1504. The marker 1504 is configured to be secured to the strut 1024, for example translationally secured to the distal end 1076 of the threaded rod 1060 such that as the threaded rod 1060 translates relative to the sleeve 1062 along the strut axis 1072, the marker 1504 also translates relative to the sleeve 1062 along the strut axis 1072. In one embodiment the marker 1504 includes threads that mate with corresponding threads on the threaded rod 1060 to secure the marker 1504 relative to the threaded rod 1060. In another embodiment, the marker 1504 is secured to the threaded rod 1060 through other means, such as an adhesive material, a magnetic material, or other fasteners.

The sensor 1502 is configured to be secured to the strut 1024, for example releasably secured to the sleeve outer surface 1092. Once secured to the sleeve 1062, the sensor 1502 is configured to detect the location of the marker 1504 along the strut axis 1072. The sensor 1502 can further be configured to display the current length, for example the length L1' of the strut 1024 that the sensor 1502 is attached to based on the detected location of the marker 1504 along the strut axis 1072. The sensor 1502 includes a first end 1505, a second end 1506, and a sensor body 1508 that extends from the first end 1505 to the second end 1506. In one embodiment the sensor body 1508 includes an inner surface 1510 that is configured to face, or abut, the sleeve outer surface 1092. As shown in the illustrated embodiment, the inner surface 1510 can have a shape, for example a concave curve, such that the inner surface 1510 corresponds in shape to a portion of the sleeve outer surface 1092.

The sensor 1502 can include an engagement mechanism 1512 that is configured to engage with the engagement mechanism 1099 of the sleeve 1062 to secure the sensor 1502 relative to the sleeve 1062. In one embodiment, the engagement mechanism 1512 includes a projection 1514 that is positioned on the inner surface 1510 and extends in a direction away from the inner surface 1510. The projection 1514 can correspond in shape to the recess 1101 such that the projection 1514 is configured to be inserted into the recess 1101. In one embodiment, when the projection 1514 is inserted into the recess 1101, the sensor 1502 is translationally secured relative to the sleeve 1062 such that the sensor 1502 and the sleeve 1062 are prevented from translating relative to one another along the strut axis 1072. In one embodiment, when the projection 1514 is inserted into the recess 1101, the sensor 1502 is rotatable relative to the sleeve 1062 such that the sensor 1502 and the sleeve 1062 can be rotated relative to one another about the strut axis 1072.

In accordance with one embodiment, the sensor 1502 can be configured to be attached to struts 1024 of different sizes. For example the sensor 1502 can be configured to be attached to any combination of lengths of struts 1024, for example extra short, short, medium, and long struts 1024, and display the current length L1' of whichever of the struts 1024 the sensor 1502 is currently attached to.

The sensor 1502 can further include a housing 1516 that encloses additional components 1518 of the sensor 1502. For example, the housing 1516 can enclose a power source, such as a battery, and a set of electronics that are configured to collect data about the location of the marker 1504 along the strut axis 1072 and convert that data into a displayed length L1' of the strut 1024. In one embodiment the sensor 1502 includes a display 1520, for example a digital display, which displays the current length L1' of the strut 1024 to the user. For example if the length L1' of the strut 1024 is currently 115.0 mm, the display 1520 will display "115.0 mm" as shown in the illustrated embodiment. In another embodiment the sensor 1502 is configured to transmit the length L1' of the strut 1024, either through a wired or wireless connection, to a separate display. For example, the sensor 1502 can be configured to transmit the length L1' of the strut 1024 over a Bluetooth connection to the user's smartphone.

Figure 12B:
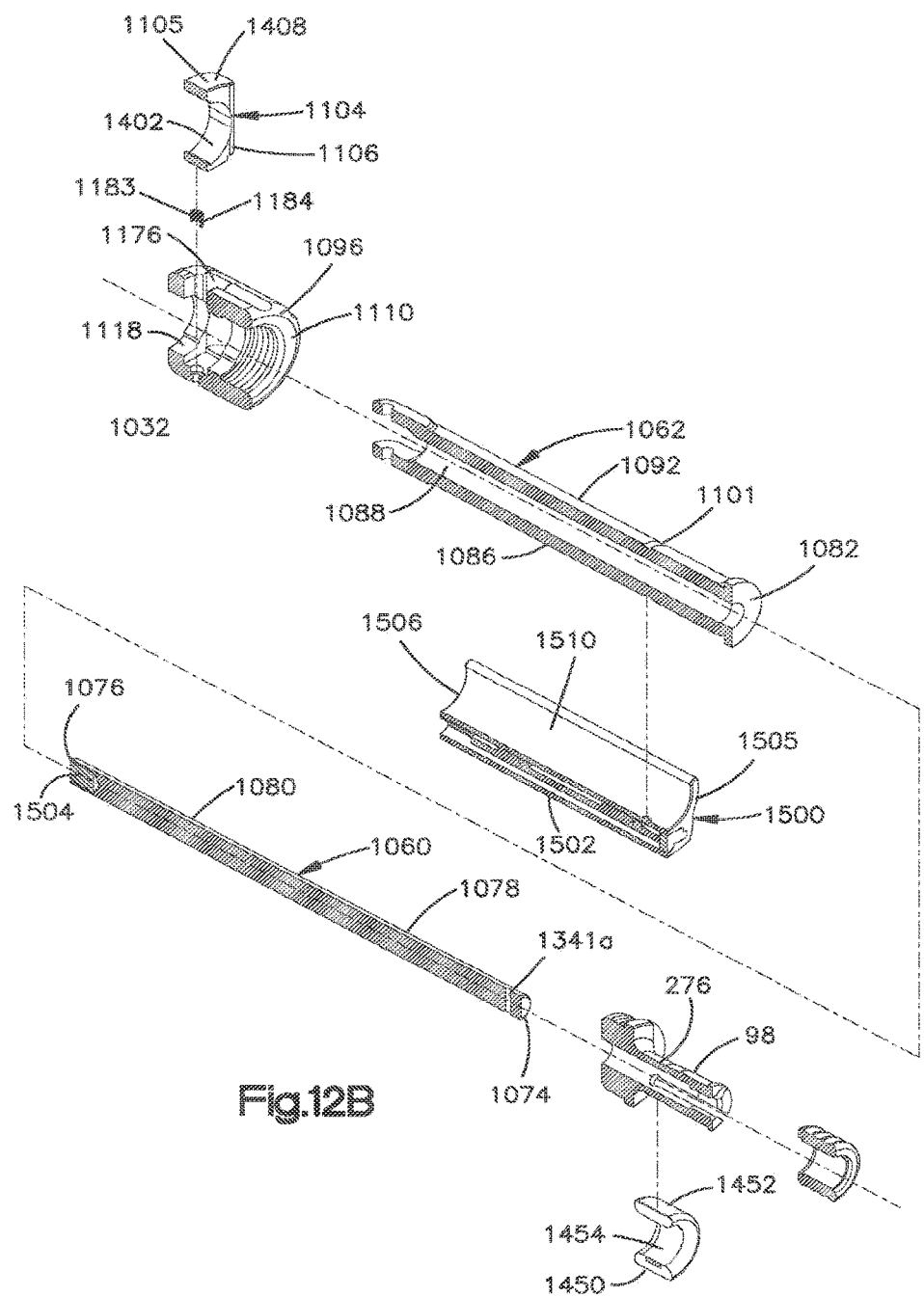
FIG. 12B is an exploded, cross-sectional view of the strut illustrated in FIG. 11A along line 12B-12B.
Figure 14A:
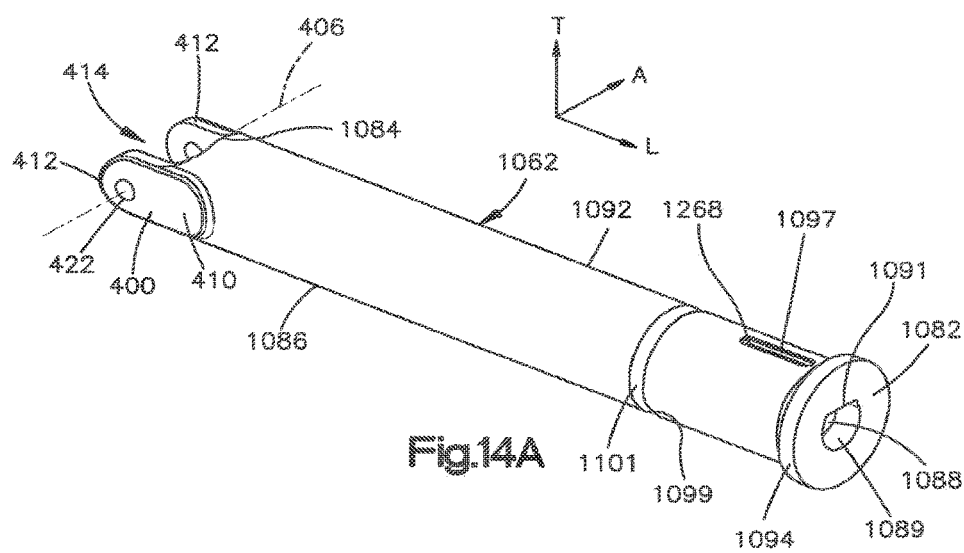
FIG. 14A is a perspective view of the sleeve illustrated in FIG. 11A.
Figure 14B:
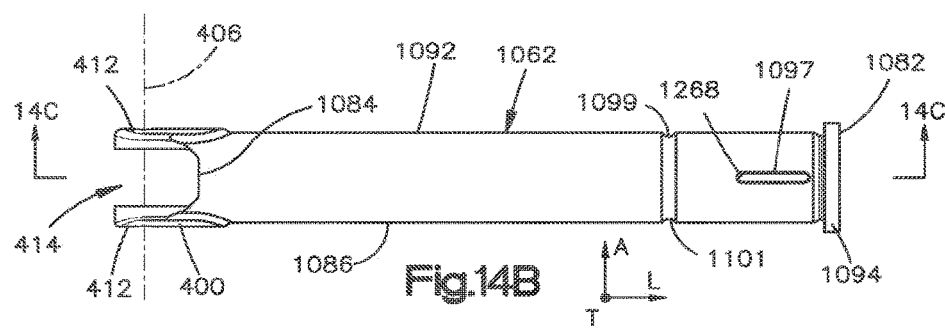
FIG. 14B is a top plan of the sleeve illustrated in FIG. 14A.
Figure 14C:
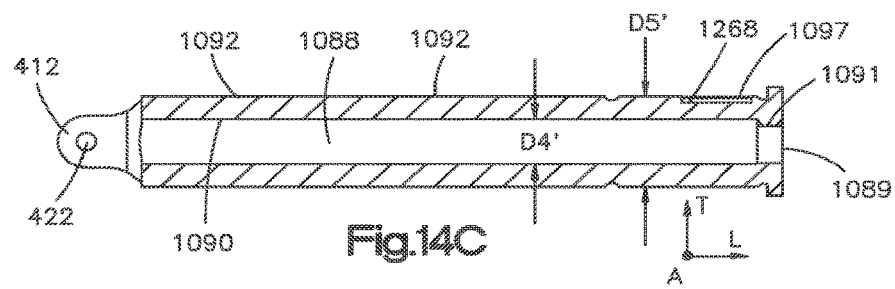
FIG. 14C is a side cross-sectional view of the sleeve illustrated in FIG. 14A along line 14C-14C.
Figure 20D:
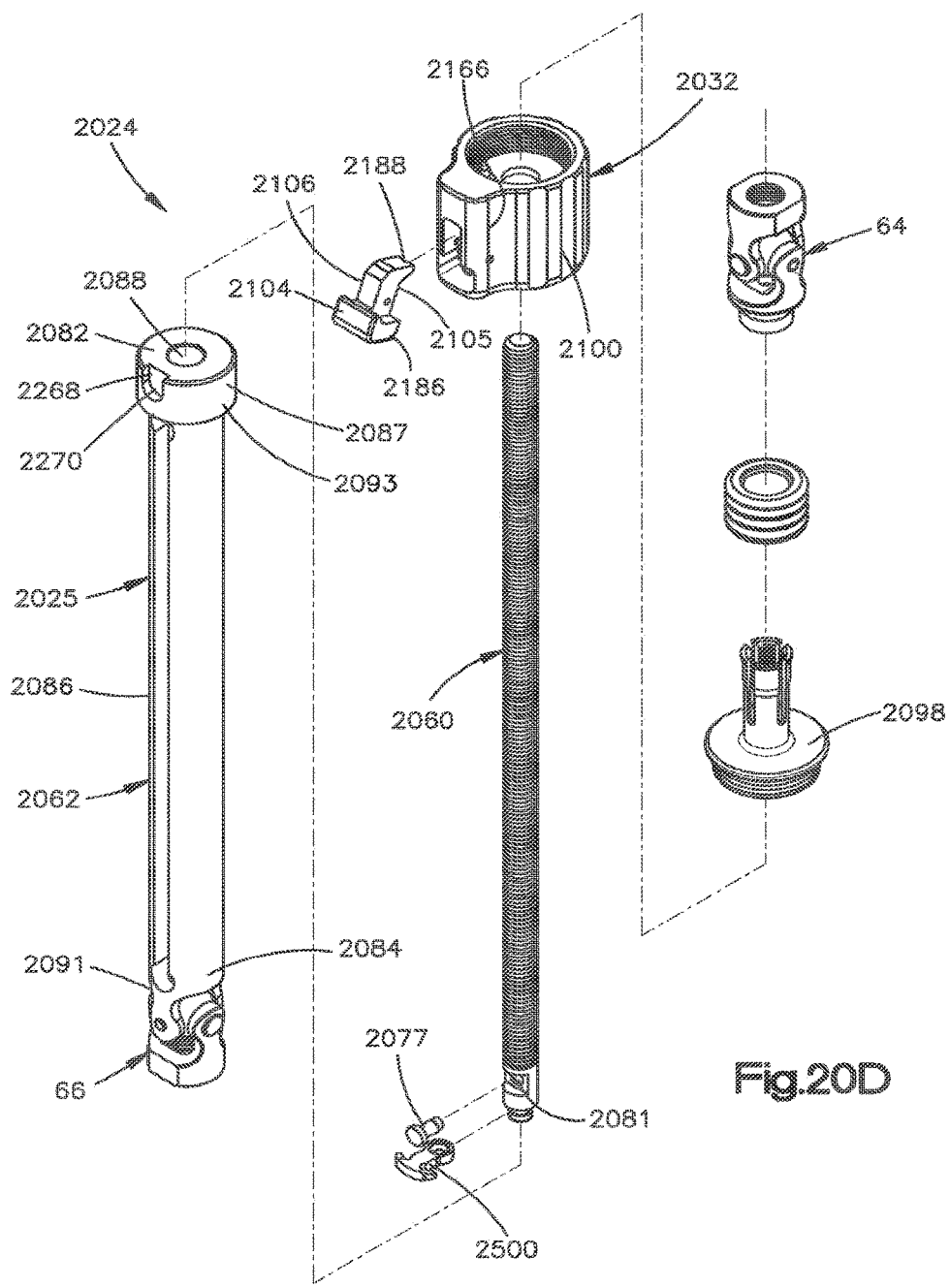
FIG. 20D is an exploded perspective view of the strut illustrated in FIG. 20A.
Figure 22D:
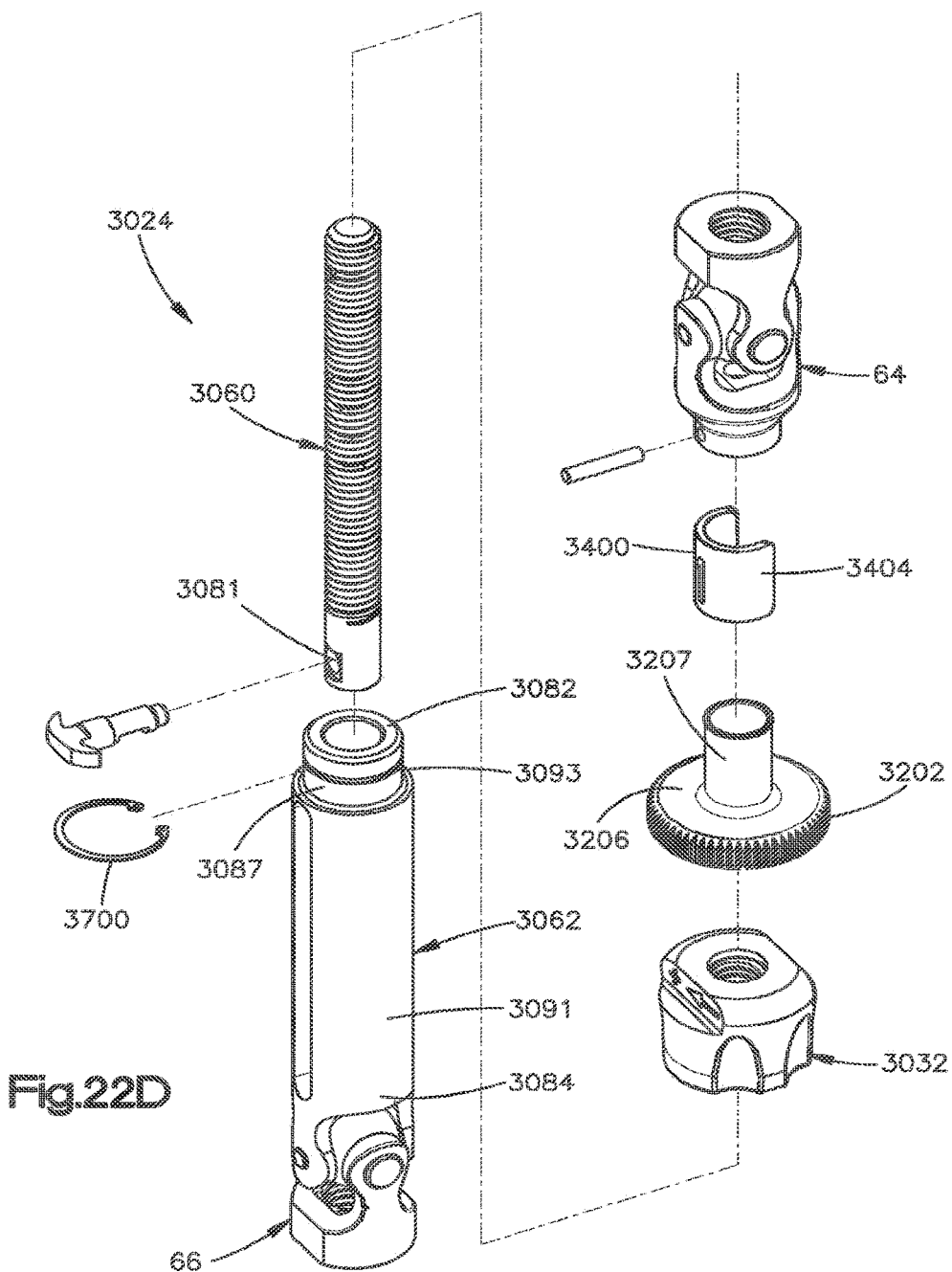
FIG. 22D is an exploded perspective view of the strut illustrated in FIG. 22A.

Referring to FIGS. 12A to 12B and 19A to 19C, in one embodiment the strut 1024 can be actuated to adjust the length L1' as described below. Note that as shown in FIG. 12A to assemble the strut 1024, the sleeve 1062 would be rotated 90 degrees about the strut axis so that first hinge body 400 fits through the bore 1118 of the gripping member 1100, then the sleeve 1062 would be rotated another 90 degrees in the same direction of rotation about the strut axis 1072 so that the recess 1097 faces "downward" and is aligned with the projection 1416 of the push member 1106.

Referring to FIGS. 19A to 19B, the strut 1024 defines a first value for the length L1' and the strut 1024 is in a locked configuration. The length L1' is measured from a first point on the strut 1024 to a second point on the strut 1024. As shown in the illustrated embodiment, the first point can be located within the sleeve, for example the center of the first pin hole 422, and the second point can be located within the threaded rod 1060, for example the center of the pin hole 1341*a*. Thus, in one embodiment, the length L1' is measured from the center of the first pin hole 422 to the center of the pin hole 1341*a* in a straight line along the strut axis 1072. The length L1' of the strut 1024 is adjustable between a first length (as shown in FIGS. 19A and 19B), for example a minimum length and a second length (as shown in FIG. 19C), for example a maximum length. The length L1' is adjustable by actuation of the actuator 1032. The actuation of the actuator 1032 can include translation along the strut axis 1072, rotation about the strut axis 1072, or both relative to the threaded rod 1060.

To change the length L1' of the strut 1024, the locking mechanism 1104 is moved from the first, locked configuration (as shown in FIG. 19A) to the second unlocked configuration (as shown in FIG. 19B). For example, an applied force is exerted by a user on the upper surface 1408 of the push member 1106. Once the applied force is greater than the biasing force applied by the spring 1184 on the lower surface 1410, the push member 1106 translates towards the base surface 1177 and compresses the spring 1184. As described above the direction of translation of the push member 1106 is substantially perpendicular to the strut axis 1072, according to one embodiment.

Referring to FIG. 19B, the push member 1106 can be translated toward the base surface 1177 until the projection 1416 is completely removed from the 1097, as shown. When the projection 1416 is removed from the recess 1097, the locking mechanism 1104 is in the second, unlocked configuration and the actuator 1032 is now rotatable relative to the threaded rod 1060 about the strut axis 1072.

Once the actuator 1032 has been rotated in a first direction, for example counter-clockwise, such that the projection 1416 of the push member 1106 is no longer aligned with the recess 1097, the applied force can be removed from the upper surface 1408. A torque applied to the gripping member 1100, will cause the actuator 1032 to rotate relative to the threaded rod 1060. Because the actuator 1032 is translationally coupled to the sleeve 1062, rotation of the actuator 1032 causes the threaded rod 1060 to translate relative to the actuator 1032 and the sleeve 1062 changing the length L1'. As shown in the illustrated embodiment, the shoulder portion 1094 is captured between the distraction nut 96 and the drive nut 98, such that the actuator 1032 is translationally coupled to the sleeve 1062.

Upon the completion of a full rotation (360 degrees) of the actuator 1032 relative to the sleeve 1062 about the strut axis 1072, the projection 1416 of the of the push member 1106 is once again in alignment with the recess 1097 of the sleeve 1062. Once the projection 1416 and the recess 1097 are aligned, the biasing force of the spring 1184 translates the push member 1106 in a direction, for example substantially perpendicular to the strut axis 1072 until the projection 1416 is at least partially received within the recess 1097. When the projection 1416 is at least partially received within the recess 1097 the locking mechanism 1104 is once again in the first, locked configuration and further rotation of the actuator 1032 relative to the threaded rod 1060 about the strut axis 1072 is prevented by interference between the projection 1416 and the recess 1097. In one embodiment, the locking mechanism body 1105, for example the projection 1416, and the locking feature 1268, for example the recess 1097, include opposed surfaces, for example first and second surfaces. The opposed surfaces are configured such that no amount of torque applied by hand to the locking mechanism 1104 about the strut axis 1072 will cause the opposed surfaces to cam over one another.

In one embodiment, the opposed surfaces are planar and substantially parallel to one another. In another embodiment the opposed (first and second) surfaces are substantially perpendicular to the strut axis 1072. As the locking mechanism 1104 translates back into the first, locked configuration an audible indication, for example a "click" can be produced to alert a user to the completion of a revolution of the actuator 1032 and confirm that the locking mechanism 1104 is once again in the first, locked configuration. In another embodiment, as the locking mechanism 1104 rotates back into the first, locked configuration a visual indication, a tactile indication, or both are produced, either instead of or in addition to the audible indication, to alert the user to the completion of a revolution of the actuator 1032 and confirm that the locking mechanism 1104 is once again in the first, locked configuration.

As shown, the locking mechanism 1104 is configured such that the biasing force of the spring 1184 is applied to the lower surface 1410 of the push member 1106 in a direction that is angularly offset from the direction of elongation of the strut 1024, or the strut axis 1072. As shown in the illustrated embodiment the biasing force can be applied to the lower surface 1410 in a direction that is substantially perpendicular to the direction of elongation of the strut 1024 or the strut axis 1072. The angular offset of the biasing force relative to the strut axis 1072, can prevents the application of a torque to the actuator 1032 from rotating the actuator 1032 relative to the threaded rod 1060 when the locking mechanism 1104 is in the first, locked configuration. Thus, in the illustrated embodiment, only when the locking mechanism 1104 is in the second, unlocked configuration does the application of a torque to the actuator 1032 rotate the actuator 1032 relative to the sleeve 1062.

The strut 1024 can be configured such that a single rotation (360 degrees) of the actuator 1032 relative to the threaded rod 1060, translates the threaded rod 1060 a predetermined amount relative to the sleeve 1062. Thus a single rotation of the actuator 1032 relative to the threaded rod 1060 can change the length L1' a predetermined amount. The predetermined amount can be adjusted, for example by selecting a pitch for the corresponding threads of the actuator 1032 and the threaded rod 1060. In one embodiment, a single rotation of the actuator 1032 relative to the threaded rod 1060, changes the length L1' of the strut 1024 by 1 mm.

Referring to FIG. 19A to 19C, the marker 1504 as shown is secured proximate the distal end 1076 of the threaded rod 1060. Additionally, the sensor 1502 is secured to the sleeve 1062. With the marker 1504 and the sensor 1502 in place as shown, the sensor 1502 will determine the position of the marker 1504 relative to the sensor 1502 with respect to the strut axis 1072 and calculate a value for the length L1' of the strut 1024. The value for the length L1' can then be displayed or transmitted to a device that displays the length L1' to the user. As the length L1' of the strut 1024 is adjusted and the threaded rod 1060 translates relative to the sleeve 1062, the marker 1504 moves from a first position 1600 (as shown in FIGS. 19A and 19B) relative to the sensor 1502 with respect to the strut axis 1072, to a second position 1602 (as shown in FIG. 19C) relative to the sensor 1502 with respect to the strut axis 1072. As the marker 1504 moves from the first position 1600 to the second position 1602 the sensor 1502 continually determines the current length L1' of the strut 1024 and displays or transmits the current length L1'.

Referring to FIGS. 20A to 20D, in one embodiment, the device 20 can include at least one strut 2024. The structure, function, and method of use of the strut 2024 is similar to structure, function, and method of use of the strut 24 in many aspects such that the description of the strut 24 herein can be applied to the strut 2024 except where indicated to the contrary. In accordance with one embodiment, the strut 2024 includes a strut body 2025, the strut body 2025 can include, a first member, for example a threaded rod 2060, and a second member, for example a sleeve 2062. The threaded rod 2060 and the sleeve 2062 are configured to be connected such that the threaded rod 2060 and the sleeve 2062 are translatable relative to one another. The strut 2024 can further include the first joint 64, as described in detail above, connected to the threaded rod 2060, and the second joint 66, as described in detail above, connected to the sleeve 2062. The strut 2024 also includes an actuator 2032 configured to be coupled to the strut 2024, for example supported by the strut body 2025 such that actuation of the actuator 2032 translates the threaded rod 2060 relative to the sleeve 2062.

The strut 2024 includes a first end, such as a proximal end 2068, and a second end, such as a distal end 2070. The strut 2024 further includes a strut axis 2072 that extends from the proximal end 2068 to the distal end 2070. The strut 2024, according to one embodiment, can be elongate along the strut axis 2072 as shown in the illustrated embodiment. The strut axis 2072 can be a central axis, and the strut axis 2072 can further be parallel to the longitudinal direction L. The strut 2024 defines a length L1" measured from a first point 2073 on the strut body 2025 to a second point 2075 on the strut body 2025, the length L1" being measured along the strut axis 2072. In one embodiment the first point 2073 is located at or near the proximal end 2068, for example in the first joint 64, and the second point 2075 is located at or near the distal end 2070, for example in the second joint 66. Actuation of the actuator 2032 causes the threaded rod 2060 to translate relative to the sleeve 2062, changing the length L1".

The threaded rod 2060 is similar to the threaded rod 60 in many aspects such that the description of the threaded rod 60 herein can be applied to the threaded rod 2060 except where indicated to the contrary. The strut 2024 can include a follower 2077. The follower 2077 can be supported by the rod distal end 2076 as shown in the illustrated embodiment. The follower 2077 is configured to prevent the threaded rod 2060 from rotating relative to the sleeve 2062 as the threaded rod 2060 translates relative to the sleeve 2062.

As shown in the illustrated embodiment, the follower 2077 can be configured similarly to the follower 77. The rod distal end 2076 can include a flat section that is configured to receive the follower 2077 such that the follower 2077 is positioned in a hole 2081 in the threaded rod 2060, such that the follower 2077 protrudes at least partially out of the hole 2081 and at least partially into a track 2089 of the sleeve 2062 as described in detail below to prevent the threaded rod 2060 from rotating relative to the sleeve 2062 about the strut axis 2072.

The sleeve 2062 is similar to the sleeve 62 in many aspects such that the description of the sleeve 62 herein can be applied to the sleeve 2062 except where indicated to the contrary. The sleeve 2062 includes a first end, for example a sleeve proximal end 2082, a second end, for example a sleeve distal end 2084, and a sleeve body 2086 that extends from the sleeve proximal end 2082 to the sleeve distal end 2084 and is elongate in the longitudinal direction L. The sleeve body 2086 includes a sleeve proximal portion 2087 that includes the sleeve proximal end 2082, and a sleeve distal portion 2091 that includes the sleeve distal end 2084. The sleeve 2062 can also include a recess such as a bore 2088, as shown, that extends into and at least partially through the sleeve body 2086 from the sleeve proximal end 2082, in the longitudinal direction L towards the sleeve distal end 2084.

In one embodiment, the sleeve 2062 is configured to connect the actuator 2032 such that the actuator 2032 is translationally fixed relative to the sleeve 2062, and rotatable about the strut axis 2072 relative to the sleeve 2062. The actuator 2032 can include a distraction nut 2096, and a drive nut 2098. The actuator 2032 can be configured to carry at least a portion of a locking mechanism 2104 of the strut 2024. In one embodiment, the distraction nut 2096 and the drive nut 2098 are configured to be rotationally and translationally coupled to each other, such that for example, as the distraction nut 2096 translates along the longitudinal direction L, the drive nut 2098 also translates along the longitudinal direction L, and as the distraction nut 2096 rotates about the longitudinal direction L, the drive nut 2098 also rotates about the longitudinal direction L.

The locking mechanism 2104 can include a locking mechanism body 2105, for example a lever 2106 and a locking feature 2268, for example a recess 2270 that is configured to receive a stop portion 2188 of the lever 2106, as described in further detail below. According to one embodiment, the sleeve proximal portion 2087 can define the locking feature 2268. The recess 2270 and the stop portion 2188, in one embodiment, have corresponding shapes such that when the locking mechanism 2104 is in the first, locked configuration the stop portion 2188 is at least partially received within the recess 2270 preventing rotation of the locking mechanism 2104 relative to the sleeve 2062 about the strut axis 2072. When the locking mechanism 2104 is in the second, unlocked configuration, in one embodiment the stop portion 2188 is completely removed from the recess 2270 such that the locking mechanism 2104 can rotate relative to the sleeve 2062, for example about the strut axis 2072.

As shown in the illustrated embodiment, the sleeve 2062 can include a shoulder portion 2093 that defines the locking feature 2268. The shoulder portion 2093 is structurally and functionally similar to the bearing 190 described above in reference to strut 24, except that the shoulder portion 2093 is integral, or monolithic, with the sleeve 2062.

The sleeve 2062 can further include a track 2089 that is configured to receive the follower 2077 of the threaded rod 2060 such that interference of the follower 2077 and the track 2089 prevents rotation of the threaded rod 2060 relative to the sleeve 2062 as the threaded rod 2060 translates relative to the sleeve 2062. The track 2089 is similar to the track 89 in many aspects such that the description of the track 89 herein can be applied to the track 2089.

In one embodiment the strut 2024 can include a length indicator 2500. The length indicator 2500 is similar to the length indicator 500 in many aspects such that the description of the length indicator 500 herein can be applied to the length indicator 2500. In another embodiment, the strut 2024 can include the length measurement device 1500 instead of the length indicator 500.

The strut 2024 further includes the actuator 2032. The actuator 2032 is similar to the actuator 32 in many aspects such that the description of the actuator 32 herein can be applied to the actuator 2032.

In one embodiment the strut 2024 can be assembled and actuated as described below. The actuation of the actuator 2032 can include translation along the strut axis 2072, rotation about the strut axis 2072, or both relative to the threaded rod 2060. The threaded rod 2060 can be inserted into the bore 2088 of the sleeve 2062 such that the follower 2077 is at least partially received within the track 2089. Once the threaded rod 2060 is positioned within the sleeve 2062 as described, the threaded rod 2060 and the sleeve 2062 are translatable relative to each other along the strut axis 2072, but they are not rotatable relative to each other about the strut axis 2072.

The actuator 2032 is attachable to the strut body 2025 such that the shoulder portion 2093 of the sleeve 2062 is captured between a distraction nut 2096 of the actuator 2032 and a drive nut 2098 of the actuator 2032 such that the shoulder portion 2093 is rotatable relative to the actuator 2032 about the strut axis 2072. The drive nut 2098 is attachable to the distraction nut 2096 such that the drive nut 2098 and the distraction nut are translationally and rotationally coupled to each other.

The drive nut 2098 is similar to the drive nut 98 as described herein such that the drive nut 2098 is configured to be placed in a closed configuration and an open configuration as described in detail above in reference to drive nut 98. To change the length L1″ of the strut 2024, the locking mechanism 2104 is moved from the first, locked configuration to the second unlocked configuration. For example, an applied force is exerted by a user on a base portion 2186 of the lever 2106 of the locking mechanism 2104. The applied force is greater than the biasing force applied by a spring 2184 on a base portion 2186 of the lever 2106, and the applied force is applied in substantially the opposite direction of the biasing force of the spring 2184.

Application of the applied force as described above pivots the lever 2106 about a pivot axis 2178. As the lever 2106 pivots about the pivot axis 2178, the stop portion 2188 of the lever 2106 moves out of engagement with the recess 2270 of the sleeve 2062. When the stop portion 2188 is removed from the recess 2270, the locking mechanism 2104 is in the second, unlocked configuration and the actuator 2032 is now rotatable relative to the threaded rod 2060 about the strut axis 2072.

Once the locking mechanism 2104 is in the second, unlocked configuration a torque applied to the gripping member 2100, for example to a projection 2166, rotates the actuator 2032 relative to the threaded rod 2060. Because the actuator 2032 is translationally coupled to the sleeve 2062, rotation of the actuator 2032 causes the threaded rod 2060 to translate relative to the actuator 2032 and the sleeve 2062, causing the length L1" to change.

Upon the completion of a full rotation (360 degrees) about the strut axis 2072, the stop portion 2188 of the lever 2106 will be in alignment with the recess 2270 of the sleeve 2062. Once the stop portion 2188 and recess 2270 are aligned, the biasing force of the spring 2184 pivots the lever 2106 about the pivot axis 2178 until the stop portion 2188 is at least partially received within the recess 2270. When the stop portion 2188 is at least partially received within the recess 2270 the locking mechanism 2104 is once again in the first, locked configuration and further rotation of the actuator 2032 relative to the sleeve 2062 and the threaded rod 2060 about the strut axis 2072 is prevented by interference between the stop portion 2188 and the recess 2270. In one embodiment, the locking mechanism body 2105, for example the stop portion 2188, and the locking feature 2268, for example the recess 2270, include opposed surfaces, for example first and second surfaces. The opposed surfaces are configured such that no amount of torque applied by hand to the locking mechanism 2104 about the strut axis 2072 will cause the opposed surfaces to cam over one another.

In one embodiment, the opposed surfaces are planar and substantially parallel to one another. In another embodiment the opposed (first and second) surfaces are substantially perpendicular to the strut axis 2072. As the locking mechanism 2104 rotates back into the first, locked configuration an audible indication, for example a "click" is produced to alert a user to the completion of a revolution of the actuator 2032 and confirm that the locking mechanism 2104 is once again in the first, locked configuration. In another embodiment, as the locking mechanism 2104 rotates back into the first, locked configuration a visual indication, a tactile indication, or both are produced, either instead of or in addition to the audible indication, to alert a user to the completion of a revolution of the actuator 2032 and confirm that the locking mechanism 2104 is once again in the first, locked configuration.

The locking mechanism 2104 can be configured such that the biasing force of the spring 2184 is applied to the base portion 2186 of the lever 2106 in a direction that is angularly offset from the direction of elongation of the strut 2024, or the strut axis 2072, as shown in the illustrated embodiment. The angular offset of the biasing force relative to the strut axis 2072, shown in the illustrated embodiment, can help prevent the application of a torque to the actuator 2032 from rotating the actuator 2032 relative to the threaded rod 2060 when the locking mechanism 2104 is in the first, locked configuration. Thus, in one embodiment, only when the locking mechanism 2104 is in the second, unlocked configuration does the application of a torque to the actuator 2032 rotate the actuator 2032 relative to the threaded rod 2060.

Referring to FIGS. 21A to 21D, in one embodiment, the device 20 can include at least one strut 3024. The structure, function, and method of use of the strut 3024 is similar to structure, function, and method of use of the strut 24 in many aspects such that the description of the strut 24 herein can be applied to the strut 3024 except where indicated to the contrary. In accordance with one embodiment, the strut 3024 includes a strut body 3025, the strut body 3025 can include, a first member, for example a threaded rod 3060, and a second member, for example a sleeve 3062. The threaded rod 3060 and the sleeve 3062 are configured to be connected such that the threaded rod 3060 and the sleeve 3062 are translatable relative to one another. The strut 3024 can further include the first joint 64, as described in detail above, connected to the threaded rod 3060, and the second joint 66, as described in detail above, connected to the sleeve 3062. The strut 3024 also includes an actuator 3032 configured to be coupled to the strut 3024, for example supported by the strut body 3025 such that actuation of the actuator 3032 translates the threaded rod 3060 relative to the sleeve 3062.

The strut 3024 includes a first end, such as a proximal end 3068, and a second end, such as a distal end 3070. The strut 2024 further includes a strut axis 3072 that extends from the proximal end 3068 to the distal end 3070. The strut 3024, according to one embodiment, can be elongate along the strut axis 3072 as shown in the illustrated embodiment. The strut axis 3072 can be a central axis, and the strut axis 3072 can further be parallel to the longitudinal direction L. The strut 3024 defines a length L1''' measured from a first point 3073 on the strut body 3025 to a second point 3075 on the strut body 3025, the length L1''' being measured along the strut axis 3072. In one embodiment the first point 2073 is located at or near the proximal end 3068, for example in the first joint 64, and the second point 3075 is located at or near the distal end 3070, for example in the second joint 66. Actuation of the actuator 3032 causes the threaded rod 3060 to translate relative to the sleeve 3062, changing the length L1'''.

The threaded rod 3060 is similar to the threaded rod 60 in many aspects such that the description of the threaded rod 60 herein can be applied to the threaded rod 3060 except where indicated to the contrary. The strut 3024 can include a follower 3077. The follower 3077 can be supported by the threaded rod 3060 such that the follower 3077 is both translationally and rotationally secured to the threaded rod 3060. The follower 3077 is configured to prevent the threaded rod 3060 from rotating relative to the sleeve 3062 as the threaded rod 3060 translates relative to the sleeve 3062. As shown in the illustrated embodiment, the threaded rod 3060 can include a hole 3081 that is configured to receive the follower 3077.

The sleeve 3062 is similar to the sleeve 62 in many aspects such that the description of the sleeve 62 herein can be applied to the sleeve 3062 except where indicated to the contrary. The sleeve 3062 includes a first end, for example a sleeve proximal end 3082, a second end, for example a sleeve distal end 3084, and a sleeve body 3086 that extends from the sleeve proximal end 3082 to the sleeve distal end 3084 and is elongate in the longitudinal direction L. The sleeve body 3086 includes a sleeve proximal portion 3087 that includes the sleeve proximal end 3082, and a sleeve distal portion 3091 that includes the sleeve distal end 3084. The sleeve 3062 can also include a circumferential groove 3093 that is configured to secure the sleeve 3062 to the actuator 3032 as described in detail below. As shown in the illustrated embodiment the circumferential groove 3093 is positioned within the sleeve proximal portion 3087 and extends into and at least partially through the sleeve body 3086.

The sleeve 3062 is configured to connect the actuator 3032 such that the actuator 3032 is translationally fixed relative to the sleeve 3062, and rotatable about the strut axis 3072 relative to the sleeve 3062. As shown the in the illustrated embodiment, the strut 3024 includes a member, for example a c-clip 3700, that is configured to be partially received in the circumferential groove 3093 of the sleeve 3062 and partially in a circumferential groove 3033 of the actuator 3032.

The strut 3024 further includes the actuator 3032. The actuator 3032 includes a distraction nut 3096. The distraction nut 3096 includes a first portion 3098 that is configured to receive the sleeve proximal portion 3087, and a second portion 3099 that is configured to receive the threaded rod 3060. As shown the first portion 3098 can include a recess 3102 that is defined by an inner surface 3104 of the first portion 3098. The second portion 3099 can include a through bore 3106 that is defined by an inner surface 3108 of the second portion 3099. In one embodiment, the inner surface 3108 of the second portion 3099 includes threads that are configured to engage with the threaded rod 3060 and the inner surface 3104 of the first portion 3098 is unthreaded. In one embodiment, the inner surface 3108 defines a circumference, and an entirety of the circumference of at least a portion of the inner surface 3108 is threaded. In another embodiment, the entirety of the circumference contacts the threaded rod 3060 both when the actuator is rotated in a first direction of rotation about the strut axis and when the actuator is rotated in a second direction of rotation about the strut axis that is opposite the first direction of rotation.

In one embodiment, the actuator 3032 can define a maximum outer diameter OD1. As shown in the illustrated embodiment, when the actuator 3032 is supported by the sleeve 3062, the actuator 3032 defines a first maximum cross-sectional dimension OD1 with respect to a direction perpendicular to the strut axis 3072. In one embodiment when the actuator 3032 is supported by the sleeve 3062, the strut 3024 is devoid of any mechanism that disengages the threaded attachment of the inner surface 3108 of the actuator 3032 and the threaded rod 3060.

The strut 3024 can further include a locking mechanism 3200. The locking mechanism 3200 can include a cinch nut 3202 that defines a locked configuration and an unlocked configuration. When the locking mechanism 3200 is in the locked configuration the actuator 3032 is prevented from rotating relative to the sleeve 3062 about the strut axis 3072. The locking mechanism 3200 can be configured such that when the locking mechanism 3200 is in the locked configuration the actuator 3032: 1) is prevented from rotating relative to the sleeve 3062 about the strut axis 3072 in one direction, for example a clockwise direction, and 2) is free to rotate relative to the sleeve 3062 about the strut axis 3072 in another direction, for example a counter-clockwise direction. When the locking mechanism 3200 is in the unlocked configuration the actuator 3032 is free to rotate relative to the sleeve 3062 about the strut axis 3072 in either direction.

The cinch nut 3202 can include a first surface 3204, a second surface 3206 that faces opposite the first surface 3204, and a cinch nut body 3208 that extends from the first surface 3204 to the second surface 3206. The cinch nut 3202 can further include a threaded bore hole 3210 that extends through the cinch nut body 3208 from the first surface 3204 to the second surface 3206. When the cinch nut 3202 is attached to the threaded rod 3060 such that the threaded rod 3060 is received within the threaded bore hole 3210, the first surface 3204 faces the actuator 3032. The strut 3024 is configured such that in the locked configuration the first surface 3204 of the cinch nut 3202 abuts the second portion 3099 of the actuator 3032. The strut 3024 can further be configured such that in the unlocked configuration the first surface 3204 of the cinch nut 3202 is spaced from the second portion 3099 of the actuator 3032 along the strut axis 3072. The cinch nut 3202 is configured to be rotated with respect to the threaded rod 3060 about the strut axis 3072 to move from the locked configuration to the unlocked configuration.

The cinch nut 3202 can further define a second maximum cross-sectional dimension. When the locking mechanism is supported by the threaded rod the second maximum cross-sectional dimension OD2 is measured in a direction perpendicular to the strut axis 3072. In one embodiment the second maximum cross-sectional outer dimension OD2 is greater than the first maximum cross-sectional dimension OD1.

The actuation of the actuator 3032 includes, in one embodiment, only rotation about the strut axis 3072, relative to the threaded rod 3060. To increase the length L1''' of the strut 3024, the locking mechanism 3200 can be in either the locked configuration to the unlocked configuration, as the cinch nut 3202 is configured to only prevent rotation of the actuator 3032 relative to the sleeve 3062 and the threaded rod 3060 in a direction that decreases the length L1'''. To decrease the length L1''' of the strut 3024, the locking mechanism 3200 must be in the unlocked configuration. In another embodiment, to adjust the length L1''' of the strut 3024 in either direction, the locking mechanism 3200 must be in the unlocked configuration.

According to one embodiment, to change the length L1''' of the strut 3024, a torque is applied to a gripping member 3100 which causes the actuator 3032 to rotate relative to the threaded rod 3060 and the sleeve 3062 about the strut axis 3072. The rotation of the actuator 3032 relative to the threaded rod 3060 and the sleeve 3062 causes the threaded rod 3060 to translate relative to the actuator 3032 and the sleeve 3062, along the strut axis 3072 causing the length L1''' to change.

Once the desired length L1''' of the strut 3024 has been achieved, the cinch nut 3202 can be rotated with respect to the threaded rod 3060 about the strut axis 3072 which causes the cinch nut 3202 to translate toward the actuator 3032. Once the cinch nut 3202 abuts the actuator 3032 the strut 3024 is in the locked configuration and further adjustment of the length L1''' is restricted (in at least one direction, or alternatively in both directions).

The strut 3024 can be configured as shown such that in the unlocked configuration, rotation of the actuator 3032 with respect to the sleeve 3062 about the strut axis 3072 requires a minimum force that is constant throughout a full (360 degrees) rotation in either direction.

The device 20 can further include one or more, for example a plurality of identification members 3400 that are each configured to be supported by the strut body 3025. Each of the identification members 3400 can include information that identifies or distinguishes each of the struts 3024 that the identification member 3400 is attached to from another of the struts 3024. In one embodiment the identification members 3400 are color coded. The color coded identification members 3400 can facilitate the user completing a treatment plan. For example, a patient's take home instructions could include directions to increase the length of the red strut 3024 by 1 mm on day 1, and to then increase the length of the blue strut 3024 by 3 mm on day 2, and so on. In another embodiment the identification members 3400 are numbered so as to identify the struts 3024 by number (1, 2, etc.). The identification member 3400 can include a label 3402 that is attached, as shown in the illustrated embodiment, to an outer surface 3114 of the distraction nut 3096.

Referring to FIGS. 22A to 22D, according to another embodiment the strut 3024 can include a cinch nut 3202'. The cinch nut 3202' includes a post member 3207 that extends out from the second surface 3206 of the cinch nut 3202' in a direction away from the first surface 3204. The post member 3207 can be configured to receive the identification member 3400 as shown in the illustrated embodiment. The identification member 3400 can include a member 3404 that is configured to be attached, for example snap fit, onto the post member 3207.

Referring to FIGS. 1A-2B and 5A-6B, in one embodiment, the device 20 is configured such that when one of the first and second end portions 26 and 28 of the strut 24 is attached to one of the bases 22 the strut 24 is rotatable about the strut axis 72 relative to the attached base 22, for example a hole 50 of the attached base 22. In another embodiment, the device 20 is configured such that when the first end portion 26 is attached to one of the bases 22, and the second end portion 28 is attached to another of the bases 22, the strut 24 is rotationally locked relative to the bases 22, such that the strut is not rotatable about the strut axis 72 relative to the attached base 22, for example a hole 50 of the attached base 22.

In one embodiment, the device 20 includes the strut 24 having the first joint 64, the second joint 66, and the length L1 measured from the first joint 64 to the second joint 66 along a strut axis 72. The first and second joints 64 and 66 defining first and second fastener receiving holes 350 and 450 respectively, that are each configured to receive a fastener 14 that is configured to secure the strut 24 to a base 22. The strut 24 includes the actuator 32 configured to adjust the length L1, and a locking mechanism 104. The locking mechanism 104 is configured to be supported at least partially by the actuator 32, and the locking mechanism 104 includes a locked configuration in which the actuator 32 is prevented from adjusting the length L1, and an unlocked configuration in which the actuator 32 is able to adjust the length L1.

The device 20 further can include first and second external bone fixation members, such as bases 22a and 22b. Each of the first and second external bone fixation members includes a first side wall 44 (or an inner surface) and a second side wall 46 (or an outer surface) that is opposite the first side wall 44. The first side wall 44 defines a space configured to receive the bone 2. The first and second bases 22 each further include a top (or first) surface 38 and a bottom (or second) surface 40 that each extends between the respective first and second side walls 44 and 46. The bases 22 each further including a hole 50 extending from the first (or upper) surface 38 to the second (or lower) surface 40, the hole 50 configured to receive a fastener 14 to attach the strut 24 to the base 22. The first side wall 44 defines an opening 48 configured to receive the bone 2, and the base 22 defines a center 49 and a radial outward direction that extends from the center 49 to the hole 50 ("fastener receiving hole") that receives a fastener 14 to attach the strut 24 to the base 22.

A method of assembling the external bone fixation device 20 according to any of the embodiments disclosed herein is described below. A method of assembling the external bone fixation device 20 according to any of the embodiments disclosed herein is described below. Any of the embodiments of the strut described herein, for example the strut 24, can be positioned relative to the first external bone fixation member (for example the first base 22a) such that the fastener receiving hole 350 of the first joint 64 is aligned with the fastener receiving hole 50 of the first base 22a. A first fastener 14 is inserted into and at least partially through the fastener receiving hole 350 of the first joint 64 and the fastener receiving hole 50 of the first base 22a, such that at least a portion of the strut 24, is rotatable about the strut axis 72 relative to the fastener receiving hole 50 of the first base 22a. In one embodiment at least the locking feature 268 is rotatable about the strut axis 72 relative to the fastener receiving hole 50 of the first base 22a. In another embodiment at least the length indicator 500 is rotatable about the strut axis 72 relative to the fastener receiving hole 50 of the first base 22a. In one embodiment an entirety of the strut 24 is rotatable about the strut axis 72 relative to the fastener receiving hole 50 of the first base 22a.

The at least a portion of the strut 24 can be rotated about the strut axis 72 relative to the fastener receiving hole 50 of the first base 22a such the at least a portion of the strut 24, for example the locking feature 268 is in a predetermined orientation. The predetermined orientation can be one in which the at least a portion of the strut 24, for example the locking feature 268 is spaced from the strut axis 72 in a radially outward direction (a direction from the center 49 to the fastener receiving hole 50 of the first base 22a). The predetermined orientation can include a range of orientations such that the locking feature 268 is spaced from the strut axis 72 in a direction that includes a vector that is radially outward (a direction from the center 49 to the fastener receiving hole 50 of the first base 22a).

In other words at least a portion of the strut 24, for example the locking feature 268, is rotated such that the locking mechanism 104 faces outward from the opening 48 and the bone 2. The strut 24 is positioned relative to the second external bone fixation member (for example the base 22b) such that the fastener receiving hole 450 of the second joint 66 is aligned with the fastener receiving hole 50 of the second base 22b. A second fastener 14 is inserted into and at least partially through the fastener receiving hole 450 of the second joint 66 and the fastener receiving hole 50 of the second base 22b. Wherein after both of the fasteners 14 have been inserted into the respective fastener receiving holes, the portion of the strut 24, for example the actuator 32, is not rotatable relative to the fastener receiving hole 50 of the first base 22a about the strut axis 72 when the locking mechanism 104 is in the locked configuration.

According to another embodiment, a method of assembling an external bone fixation device configured to repair a deformity in a bone is described below. The external bone fixation device includes first and second external bone fixation members, and a strut that has a first joint configured to be attached to the first external bone fixation member, and a second joint spaced from the first joint along a strut axis, the second joint configured to be attached to the second external bone fixation member. The method comprises the steps of positioning the strut relative to the first external bone fixation member such that a first fastener receiving hole of the first joint is aligned with a second fastener receiving hole of the first external bone fixation member, inserting a first fastener at least into the first fastener receiving hole and the second fastener receiving hole so as to attach the first joint to the first external bone fixation member, rotating the strut relative to the first external bone fixation member about the strut axis to a predetermined orientation (as described above), aligning a third fastener receiving hole of a second joint of the strut with a fourth fastener receiving hole of the second external bone fixation member, and inserting a second fastener at least into the third fastener receiving hole and the fourth fastener receiving hole so as to attach the second joint to the second external bone fixation member, such that each of the first and second joints is rotatably fixed with respect to both of the first and second external bone fixation members about the strut axis.

In another embodiment, the method of assembling the external bone fixation device 20 according to any of the embodiments disclosed herein includes, positioning the strut 24 relative to the second external bone fixation member (for example the second base 22b) such that the fastener receiving hole 350 of the first joint 64 is aligned with the fastener receiving hole 50 of the second base 22b. A first fastener 14 is inserted into and at least partially through the fastener receiving hole 350 of the first joint 64 and the fastener receiving hole 50 of the second base 22b, such that at least a portion of the strut 24, for example the actuator 32, is rotatable about the strut axis 72 relative to the fastener receiving hole 50 of the second base 22b. The actuator 32 can be rotated about the strut axis 72 relative to the fastener receiving hole 50 of the second base 22b such that the locking mechanism 104 is spaced from the strut axis 72 in a radially outward direction (a direction from the center 49 to the fastener receiving hole 50 of the second base 22b). In other words at least a portion of the strut 24, for example the actuator 32, is rotated such that the locking mechanism 104 faces outward from the opening 48 and the bone 2. The strut 24 is positioned relative to the first external bone fixation member (for example the base 22b) such that the fastener receiving hole 450 of the second joint 66 is aligned with the fastener receiving hole 50 of the first base 22a. A second fastener 14 is inserted into and at least partially through the fastener receiving hole 450 of the second joint 66 and the fastener receiving hole 50 of the first base 22a. Wherein after both of the fasteners 14 have been inserted into the respective fastener receiving holes, the portion of the strut 24, for example the actuator 32, is not rotatable relative to the fastener receiving hole 50 of the second base 22b about the strut axis 72 when the locking mechanism 104 is in the locked configuration.

In another embodiment, the method of assembling the external bone fixation device 20 according to any of the embodiments disclosed herein includes, positioning the strut 24 relative to one of the external bone fixation member (for example the first base 22a) such that the fastener receiving hole 450 of the second joint 66 is aligned with the fastener receiving hole 50 of the first base 22a. The actuator 32 can be rotated about the strut axis 72 relative to the fastener receiving hole 50 of the first base 22a such that the locking mechanism 104 is spaced from the strut axis 72 in a radially outward direction (a direction from the center 49 to the fastener receiving hole 50 of the first base 22a). In other words at least a portion of the strut 24, for example the actuator 32, is rotated such that the locking mechanism 104 faces outward from the opening 48 and the bone 2. A first fastener 14 is inserted into and at least partially through the fastener receiving hole 450 of the second joint 66 and the fastener receiving hole 50 of the first base 22a, such that at least a portion of the strut 24, for example the actuator 32, is not rotatable about the strut axis 72 relative to the fastener receiving hole 50 of the first base 22a when the locking mechanism 104 is in the locked configuration. A second fastener 14 is inserted into and at least partially through the fastener receiving hole 350 of the first joint 64 and the fastener receiving hole 50 of the second base 22b.

In another embodiment, the method of assembling the external bone fixation device 20 according to any of the embodiments disclosed herein includes, positioning the strut 24 relative to one of the external bone fixation member (for example the second base 22b) such that the fastener receiving hole 450 of the second joint 66 is aligned with the fastener receiving hole 50 of the second base 22b. The actuator 32 can be rotated about the strut axis 72 relative to the fastener receiving hole 50 of the second base 22b such that the locking mechanism 104 is spaced from the strut axis 72 in a radially outward direction (a direction from the center 49 to the fastener receiving hole 50 of the second base 22b). In other words at least a portion of the strut 24, for example the actuator 32, is rotated such that the locking mechanism 104 faces outward from the opening 48 and the bone 2. A first fastener 14 is inserted into and at least partially through the fastener receiving hole 450 of the second joint 66 and the fastener receiving hole 50 of the second base 22b, such that at least a portion of the strut 24, for example the actuator 32, is not rotatable about the strut axis 72 relative to the fastener receiving hole 50 of the second base 22b when the locking mechanism 104 is in the locked configuration. A second fastener 14 is inserted into and at least partially through the fastener receiving hole 350 of the first joint 64 and the fastener receiving hole 50 of the first base 22a.

In one embodiment the external bone fixation device 20 includes a kit having a plurality of struts 24 and a plurality of bases 22. The kit can further include a plurality of attachment mechanisms 200. In another embodiment, the plurality of struts 24 includes struts with different minimum and maximum lengths L1 (measured, for example, from the center 340 of the cross coupling member 304 of the first joint 64 to the center 440 of the cross coupling member 440 of the second joint 66). The plurality of struts 24 in the kit, in one embodiment, can include any combination of one or more triple extra short struts, one or more double extra short struts, one or more extra short struts, one or more short struts, one or more medium struts, and one or more long struts.

In one embodiment the triple extra short strut can be provided having a minimum length L1 of about 65 mm and a maximum length L1 of about 82 mm for a total travel distance of about 17 mm. In one embodiment the double extra short strut can be provided having a minimum length L1 of about 81 mm and a maximum length L1 of about 99 mm for a total travel distance of about 18 mm. In one embodiment the extra short struts define a minimum length L1 of about 91 mm and a maximum length L1 of about 121 mm for a total travel distance of about 30 mm. In one embodiment the short struts define a minimum length L1 of about 116 mm and a maximum length L1 of about 152 mm for a total travel distance of about 36 mm. In one embodiment the medium struts define a minimum length L1 of about 142 mm and a maximum length L1 of about 205 mm for a total travel distance of about 63 mm. In one embodiment the long struts define a minimum length L1 of about 195 mm and a maximum length L1 of about 311 mm for a total travel distance of about 116 mm.

The plurality of bases 22 in the kit, in one embodiment, can include any combination of one or more bases with an outer diameter of 90 mm, 120 mm, 150 mm, 180 mm, 210 mm, and 240 mm. The plurality of attachment mechanisms 200 in the kit, in one embodiment, can include any combination of one or more brackets 202, fasteners 206, wires 208 and rods 210. The plurality of struts in the kit, in one embodiment, can include any combination of one or more of the struts 24, 1024, 2024, and 3034.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the claims.

What is claimed:

1. An external bone fixation member comprising:
   a base body including a first surface and a second surface opposite the first surface;

a first side wall that extends between the first surface and the second surface, and a second side wall that both is opposite the first side wall and that extends between the first surface and the second surface;

a first hole and a second hole each defined by the base body such that both the first hole and the second hole extend through both the first surface and the second surface, the first and second holes defining respective first and second centers that each lies on a first circle; and a third hole and a fourth hole each defined by the base body such that both of the third hole and the fourth hole extend through both the first surface and the second surface, the third and fourth holes defining respective third and fourth centers that each lies on a second circle that is concentric with the first circle, and defines a larger diameter than the first circle; and a fifth hole defined by the base body such that the fifth hole extends through both the first surface and the second surface, the fifth hole defining a fifth center that lies on the first circle, wherein the fifth hole is positioned such that a straight line that extends through a center of the first circle intersects both the fifth center and the second circle without passing through any holes that lie on the second circle, wherein the first hole, the second hole, the third hole, and the fourth hole are positioned such that a first radial ray that extends from the center of the first circle intersects both the first center and the third center, and a second radial ray that extends from the center of the first circle intersects the fourth center without passing through any holes that lie on the first circle, wherein the base body defines a first width measured from the first side wall to the second side wall along the first radial ray, the base body defines a second width measured from the first side wall to the second side wall along the straight line, and the first width is greater than the second width, and wherein the base body extends along an entirety of the first circle.

2. The external bone fixation member of claim 1, further comprising a sixth hole defined by the base body such that the sixth hole extends through both the first surface and the second surface, the sixth hole defining a sixth center that lies on the second circle, wherein the sixth hole is positioned such that a third radial ray that extends from the center of the first circle intersects both the second center and the sixth center.

3. The external bone fixation member of claim 2, wherein the fourth hole is between the third hole and the sixth hole along the second circle.

4. The external bone fixation member of claim 1, further comprising an opening defined by the first side wall such that the opening extends through both the first surface and the second surface.

5. The external bone fixation member of claim 4, wherein the opening is configured to receive a human limb such that the first side wall at least partially encircles the human limb.

6. The external bone fixation member of claim 4, wherein the opening defines a circular shape that is concentric with the first circle.

7. The external bone fixation member of claim 4, wherein the base body includes a primary base body and a secondary base body, the primary base body defining a first portion of the first side wall, the secondary base body defining a second portion of the first side wall, the secondary base body configured to be attached to the primary base body such that the first portion and the second portion cooperate to define the opening.

8. The external bone fixation member of claim 7, wherein the first portion defines a first partial circle, the second portion defines a second partial circle, and the secondary base body is configured to be attached to the primary base body such that the first partial circle and the second partial circle cooperatively define a complete circle.

9. The external bone fixation member of claim 1, wherein the base body includes a tab that defines the first width, the base body includes a second tab that defines a third width that is equal to the first width, the base body includes a third tab that defines a fourth width that is equal to the first width, and the first tab, the second tab, and the third tab are equidistantly spaced circumferentially about the center of the first circle, and no other tabs are disposed between any of the first, second, and third tabs.

10. An external bone fixation member comprising:
a base body including a first surface, a second surface opposite the first surface;
a first side wall that extends between the first surface and the second surface, and a second side wall that both is opposite the first side wall and that extends between the first surface and the second surface;
a first hole and a second hole each defined by the base body such that both the first hole and the second hole extend through both the first surface and the second surface, the first hole defining a first center that lies on a first circle, the second hole defining a second center that lies on the first circle such that the second hole is adjacent to the first hole, such that no holes whose centers lie on the first circle are disposed between the first and second holes along the base body; and
a third hole, a fourth hole, and a fifth hole each defined by the base body such that each of the third hole, the fourth hole, and the fifth hole extends through both the first surface and the second surface, the third hole defining a third center that lies on a second circle, the fifth hole defining a fifth center that lies on the second circle, the fourth hole defining a fourth center that lies on the second circle between the third hole and the fifth hole, the second circle is concentric with the first circle, and the second circle defines a larger diameter than the first circle,
wherein the first side wall extends along an entirety of a third circle, such that the first circle is disposed between the third circle and the second circle,
wherein the first hole and the third hole are positioned such that a first radial ray that extends from a center of the first circle intersects both the first center and the third center, and the second hole and the fifth hole are positioned such that a second radial ray that extends from the center of the first circle intersects the both second center and the fifth center,
wherein a first chord length measured from the first center to the second center is greater than a second chord length measured from the third center to the fourth center,
wherein the external bone fixation member further comprises a sixth hole defined by the base body such that the sixth hole extends through both the first surface and the second surface, the sixth hole defining a sixth center that lies on the first circle, wherein the sixth hole is positioned such that a third radial ray that extends from the center of the first circle intersects both the sixth center and the second circle without passing through any holes that lie on the second circle, and wherein the base body defines a first width measured from the first side wall to the second side wall along the first radial ray, the base body defines a second width measured from the first side wall to the second side wall along the third radial ray, and the first width is greater than the second width.

11. The external bone fixation member of claim 10, wherein (i) the base body includes a first tab that defines the first width, the base body includes a second tab that defines a third width that is equal to the first width, the base body includes a third tab that defines a fourth width that is equal to the first width, (ii) the first tab, the second tab, and the third tab are equidistantly spaced radially about the center of the first circle, and (iii) the base body includes no additional tabs that include holes whose centers on the second circle other than the first, second, and third tabs.

12. An external bone fixation member comprising:
a base body including a first surface and a second surface opposite the first surface; and
a plurality of holes that are each defined by the base body such that each of the plurality of holes extends through both the first surface and the second surface, each of the plurality of holes defining a center that lies on a first circle, the plurality of holes including every hole defined by the base body with a center that lies on the first circle,
wherein each adjacent pair of the plurality of holes defines a chord length measured from the center of one of the adjacent pair to the center of the other of the adjacent pair, the chord length for every adjacent pair of the plurality of holes is equal to a first distance, except for one adjacent pair of the plurality of holes, which defines a chord length equal to a second distance, and the second distance is twice the first distance.

13. The external bone fixation member of claim 12, wherein the base body defines a first hole, a second hole, and a third hole that each extends through both the first surface and the second surface, the first hole is one of the plurality of holes and defines a first center that lies on the first circle, the second hole defines a second center that lies on a second circle, which is concentric with the first circle and larger than the first circle, the third hole defines a third center that lies on a third circle, which is concentric with the second circle and larger than the second circle, and the first hole and the third hole are radially aligned such that a first radial ray that extends from a center of the first circle intersects both the first center and the third center, and the second hole is radially offset from both the first hole and the second hole such that the first radial ray does not intersect the second center.

14. The external bone fixation member of claim 13, further comprising a fourth hole and a fifth hole each defined by the base body such that both the fourth hole and the fifth hole extend through both the first surface and the second surface, the fourth hole is one of the plurality of holes and defines a fourth center that lies on the first circle such that the first hole and the fourth hole are the one adjacent pair of the plurality of holes, the fifth hole defines a fifth center that lies on the third circle such that the fifth hole is adjacent to the third hole with respect to the third circle, and the fourth hole and the fifth hole are radially aligned such that a third radial ray that extends from the center of the first circle intersects both the fourth center and the fifth center.

* * * * *